(12) United States Patent
Bay et al.

(10) Patent No.: US 6,676,946 B2
(45) Date of Patent: Jan. 13, 2004

(54) MULTIPLE ANTIGEN GLYCOPEPTIDE CARBOHYDRATE VACCINE COMPRISING THE SAME AND USE THEREOF

(75) Inventors: Sylvie Bay, Paris (FR); Daniele Cantacuzene, Paris (FR); Claude Leclerc, Paris (FR); Richard Lo-Man, Paris (FR); Sophie Vicher-Guerre, La Celle Saint Cloud (FR)

(73) Assignee: Institut Pasteur (FR)

( * ) Notice: Subject to any disclaimer, the term of this patent is extended or adjusted under 35 U.S.C. 154(b) by 0 days.

(21) Appl. No.: 09/405,986

(22) Filed: Sep. 27, 1999

(65) Prior Publication Data

US 2003/0157115 A1 Aug. 21, 2003

Related U.S. Application Data

(63) Continuation-in-part of application No. 09/049,847, filed on Mar. 27, 1998.
(60) Provisional application No. 60/041,726, filed on Mar. 27, 1997.

(51) Int. Cl.[7] .......................... A61K 39/385; C07H 1/00
(52) U.S. Cl. ................. 424/196.11; 424/194.1; 424/193.1; 424/186.1; 424/185.1; 424/184.1; 536/1.11; 530/324; 530/350
(58) Field of Search .................. 414/196.11, 194.1, 414/193.1, 186.1, 185.1, 184.1; 536/1.11; 530/324, 350

(56) References Cited

U.S. PATENT DOCUMENTS 5,229,490 A * 7/1993 Tam ........................... 530/324
5,580,563 A * 12/1996 Tam ........................ 424/197.11
5,679,352 A * 10/1997 Chong et al. ............. 424/256.1

OTHER PUBLICATIONS

Zanini et al, Bioconjugate Chemistry, 8 187–192 (1997).*
Fung et al, Cancer Research, 50, 4308–14 (Jul. 15, 1990).*
Bay et al, J. Pept. Res. 49, 620–25 (1997).*
Storkus article, ppg. 54–77, Section 3.2.–.Immune Cells.
Coulie article, ppg. 393–403, Antigens . . . Vaccination.
Van Pel et al article, ppg. 229–250. Genes . . . Lymphocytes.

* cited by examiner

Primary Examiner—T. D. Wessendorf
(74) Attorney, Agent, or Firm—Muserlian, Lucas and Mercanti

(57) ABSTRACT

A carbohydrate peptide conjugate containing:
(i) a carrier containing a dendrimeric poly-lysine enabling multiple epitopes to be covalently attached thereto,
(ii) at least one peptide containing one T epitope or several identical or different T-epitopes,
(iii) at least one carbohydrate moiety which is tumor antigen, or a derivative thereof, containing a B epitope, provided it is not a sialoside, or several identical or different epitopes, wherein said conjugate containing at least 3-lysines and up to 15 lysine covalently linked to one another, and wherein:
(a) to the $NH_2$ and of at least two lysine residues is bound at least one carbohydrate residue being not a sialoside, optionally substituted and containing an epitope and wherein the peptide containing one T epitope is covalently bound to the end of said carbohydrate which induces immune responses.

3 Claims, 18 Drawing Sheets

B=carbohydrate, or carbohydrate and tumor peptidicmarker
T=T, $CD_4^+$ epitope
K=lysine a=B4-T4-M
b=B8-T8-M
c=B2-T2-M
d=B4-T4-M(different organization of T-B epitope)

MAG:Tn-PV

| B | = Tn antigen
*saccharidic*

| T | = PV epitope    KLFAVWKITYKDT (SEQ. ID NO. 4)
*peptidic*

SEQUENCE LISTING

```
<160> NUMBER OF SEQ ID NOS: 25

<210> SEQ ID NO 1
<211> LENGTH: 15
<212> TYPE: PRT
<213> ORGANISM: Clostridium tetani

<400> SEQUENCE: 1

Gln Tyr Ile Lys Ala Asn Ser Lys Phe Ile Gly Ile Thr Glu Leu
1               5                   10                  15

<210> SEQ ID NO 2
<211> LENGTH: 21
<212> TYPE: PRT
<213> ORGANISM: Clostridium tetani

<400> SEQUENCE: 2

Phe Asn Asn Phe Thr Val Ser Phe Trp Leu Arg Val Pro Lys Val Ser
1               5                   10                  15

Ala Ser His Leu Glu
            20

<210> SEQ ID NO 3
<211> LENGTH: 12
<212> TYPE: PRT
<213> ORGANISM: Clostridium tetani

<400> SEQUENCE: 3

Gly Gln Ile Gly Asn Asp Pro Asn Arg Asp Ile Leu
1               5                   10

<210> SEQ ID NO 4
<211> LENGTH: 13
<212> TYPE: PRT
<213> ORGANISM: Poliovirus

<400> SEQUENCE: 4
```

```
Lys Leu Phe Ala Val Trp Lys Ile Thr Tyr Lys Asp Thr
1               5                   10

<210> SEQ ID NO 5
<211> LENGTH: 15
<212> TYPE: PRT
<213> ORGANISM: Escherichia coli

<400> SEQUENCE: 5

Asn Gly Lys Leu Ile Ala Tyr Pro Ile Ala Val Glu Ala Leu Ser
1               5                   10                  15

<210> SEQ ID NO 6
<211> LENGTH: 13
<212> TYPE: PRT
<213> ORGANISM: ARTIFICIAL SEQUENCE
<220> FEATURE:
<223> OTHER INFORMATION: Designed peptidic T-Helper Cell epitope that
      typically binds to a plurality of human and murine Major
      Histocompatibility Complex Class II molecules
<220> FEATURE:
<221> NAME/KEY: MISC_FEATURE
<222> LOCATION: (1)..(1)
<223> OTHER INFORMATION: Xaa=D-Ala
<220> FEATURE:
<221> NAME/KEY: MISC_FEATURE
<222> LOCATION: (3)..(3)
<223> OTHER INFORMATION: Xaa=L-cyclohexyl-Ala
<220> FEATURE:
<221> NAME/KEY: MISC_FEATURE
<222> LOCATION: (13)..(13)
<223> OTHER INFORMATION: Xaa=D-Ala

<400> SEQUENCE: 6

Xaa Lys Xaa Val Ala Ala Trp Thr Leu Lys Ala Ala Xaa
1               5                   10

<210> SEQ ID NO 7
<211> LENGTH: 10
<212> TYPE: PRT
<213> ORGANISM: Human papillomavirus type 16
<220> FEATURE:
<221> NAME/KEY: MISC_FEATURE
<223> OTHER INFORMATION: HPV16 E7 PEPTIDE

<400> SEQUENCE: 7

Thr Asp Leu Tyr Cys Tyr Glu Gln Leu Asn
1               5                   10

<210> SEQ ID NO 8
<211> LENGTH: 10
<212> TYPE: PRT
<213> ORGANISM: Human papillomavirus type 16
<220> FEATURE:
<221> NAME/KEY: MISC_FEATURE
<223> OTHER INFORMATION: HPV16 E7 PEPTIDE

<400> SEQUENCE: 8

Ala Glu Pro Asp Arg Ala His Tyr Asn Ile
1               5                   10

<210> SEQ ID NO 9
<211> LENGTH: 19
<212> TYPE: PRT
<213> ORGANISM: Human papillomavirus type 16
<220> FEATURE:
<221> NAME/KEY: MISC_FEATURE
<223> OTHER INFORMATION: HPV 16 E7 PEPTIDE

<400> SEQUENCE: 9
```

Lys Cys Asp Ser Thr Leu Arg Leu Cys Val Gln Ser Thr His Val Ile
1               5                   10                  15

Arg Thr Leu

<210> SEQ ID NO 10
<211> LENGTH: 10
<212> TYPE: PRT
<213> ORGANISM: Human papillomavirus type 16
<220> FEATURE:
<221> NAME/KEY: MISC_FEATURE
<223> OTHER INFORMATION: HPV16 E7 PEPTIDE

<400> SEQUENCE: 10

Gly Thr Leu Gly Ile Val Cys Pro Ile Cys
1               5                   10

<210> SEQ ID NO 11
<211> LENGTH: 13
<212> TYPE: PRT
<213> ORGANISM: Homo sapiens

<400> SEQUENCE: 11

Lys Leu Val Val Val Gly Ala Arg Gly Val Gly Lys Ser
1               5                   10

<210> SEQ ID NO 12
<211> LENGTH: 15
<212> TYPE: PRT
<213> ORGANISM: Homo sapiens

<400> SEQUENCE: 12

His Leu Asp Met Leu Arg His Leu Tyr Gln Gly Cys Gln Val Val
1               5                   10                  15

<210> SEQ ID NO 13
<211> LENGTH: 15
<212> TYPE: PRT
<213> ORGANISM: Homo sapiens

<400> SEQUENCE: 13

Ser Arg Leu Leu Gly Ile Cys Leu Thr Ser Thr Val Gln Leu Val
1               5                   10                  15

<210> SEQ ID NO 14
<211> LENGTH: 14
<212> TYPE: PRT
<213> ORGANISM: Homo sapiens

<400> SEQUENCE: 14

Leu Leu Lys Tyr Arg Ala Arg Glu Pro Val Thr Lys Ala Glu
1               5                   10

<210> SEQ ID NO 15
<211> LENGTH: 10
<212> TYPE: PRT
<213> ORGANISM: POLIOVIRUS

<400> SEQUENCE: 15

Phe Ala Val Trp Lys Ile Thr Tyr Lys Asp
1               5                   10

<210> SEQ ID NO 16
<211> LENGTH: 14
<212> TYPE: PRT

```
<213> ORGANISM: Clostridium tetani

<400> SEQUENCE: 16

Tyr Ile Lys Ala Asn Ser Lys Phe Ile Gly Ile Thr Glu Leu
 1               5                  10

<210> SEQ ID NO 17
<211> LENGTH: 11
<212> TYPE: PRT
<213> ORGANISM: ARTIFICIAL SEQUENCE
<220> FEATURE:
<223> OTHER INFORMATION: Designed synthetic linear glycopeptide
      containing a saccharidic B-cell epitope and a CD4+ T-cell epitope
      able to induce anti-saccharidic antibodies

<400> SEQUENCE: 17

Ser Thr Thr Gly Gly Gly Gly Gly Gly Lys Gly
 1               5                  10

<210> SEQ ID NO 18
<211> LENGTH: 11
<212> TYPE: PRT
<213> ORGANISM: ARTIFICIAL SEQUENCE
<220> FEATURE:
<223> OTHER INFORMATION: Designed synthetic linear glycopeptide
      containing a saccharidic B-cell epitope and a CD4+ T-cell epitope
      able to induce anti-saccharidic antibodies
<220> FEATURE:
<221> NAME/KEY: MISC_FEATURE
<222> LOCATION: (1)..(1)
<223> OTHER INFORMATION: alpha-N-acetylgalactosamine (GalNAc)-Serine
<220> FEATURE:
<221> NAME/KEY: MISC_FEATURE
<222> LOCATION: (2)..(3)
<223> OTHER INFORMATION: alpha-N-acetylgalactosamine (GalNAc)-Threonine

<400> SEQUENCE: 18

Ser Thr Thr Gly Gly Gly Gly Gly Gly Lys Gly
 1               5                  10

<210> SEQ ID NO 19
<211> LENGTH: 11
<212> TYPE: PRT
<213> ORGANISM: ARTIFICIAL SEQUENCE
<220> FEATURE:
<223> OTHER INFORMATION: Designed synthetic linear glycopeptide
      containing a saccharidic B-cell epitope and a CD4+ T-cell epitope
      able to induce anti-saccharidic antibodies
<220> FEATURE:
<221> NAME/KEY: MISC_FEATURE
<222> LOCATION: (1)..(1)
<223> OTHER INFORMATION: alpha-N-acetylgalactosamine (GalNAc)-Serine
<220> FEATURE:
<221> NAME/KEY: MISC_FEATURE
<222> LOCATION: (2)..(3)
<223> OTHER INFORMATION: alpha-N-acetylgalactosamine (GalNAc)-Threonine
<220> FEATURE:
<221> NAME/KEY: MISC_FEATURE
<222> LOCATION: (10)..(10)
<223> OTHER INFORMATION: Biotinylated

<400> SEQUENCE: 19

Ser Thr Thr Gly Gly Gly Gly Gly Gly Lys Gly
 1               5                  10
```

```
<210> SEQ ID NO 20
<211> LENGTH: 11
<212> TYPE: PRT
<213> ORGANISM: ARTIFICIAL SEQUENCE
<220> FEATURE:
<223> OTHER INFORMATION: Designed synthetic linear glycopeptide
      containing a saccharidic
      B-cell epitope and a CD4+ T-cell epitope able to induce anti-
      saccharidic antibodies
<220> FEATURE:
<221> NAME/KEY: MISC_FEATURE
<222> LOCATION: (7)..(8)
<223> OTHER INFORMATION: alpha-N-acetylgalactosamine (GalNAc)-Threonine

<400> SEQUENCE: 20

Lys Gly Gly Gly Gly Ser Thr Thr Gly Gly Gly
1               5                   10

<210> SEQ ID NO 21
<211> LENGTH: 14
<212> TYPE: PRT
<213> ORGANISM: ARTIFICIAL SEQUENCE
<220> FEATURE:
<223> OTHER INFORMATION: Designed synthetic linear glycopeptide
      containing a saccharidic B-cell epitope and a CD4+ T-cell epitope
      able to induce anti-saccharidic antibodies
<220> FEATURE:
<221> NAME/KEY: MISC_FEATURE
<222> LOCATION: (1)..(1)
<223> OTHER INFORMATION: alpha-N-acetylgalactosamine (GalNAc)-Serine

<400> SEQUENCE: 21

Ser Lys Leu Phe Ala Val Trp Lys Ile Thr Tyr Lys Asp Thr
1               5                   10

<210> SEQ ID NO 22
<211> LENGTH: 16
<212> TYPE: PRT
<213> ORGANISM: ARTIFICIAL SEQUENCE
<220> FEATURE:
<223> OTHER INFORMATION: Designed synthetic linear glycopeptide
      containing a saccharidic B-cell epitope and a CD4+ T-cell epitope
      able to induce anti-saccharidic antibodies
<220> FEATURE:
<221> NAME/KEY: MISC_FEATURE
<222> LOCATION: (1)..(1)
<223> OTHER INFORMATION: alpha-N-acetylgalactosamine (GalNAc)-Serine
<220> FEATURE:
<221> NAME/KEY: MISC_FEATURE
<222> LOCATION: (2)..(3)
<223> OTHER INFORMATION: alpha-N-acetylgalactosamine (GalNAc)-Threonine

<400> SEQUENCE: 22

Ser Thr Thr Lys Leu Phe Ala Val Trp Lys Ile Thr Tyr Lys Asp Thr
1               5                   10                  15

<210> SEQ ID NO 23
<211> LENGTH: 16
<212> TYPE: PRT
<213> ORGANISM: ARTIFICIAL SEQUENCE
<220> FEATURE:
<223> OTHER INFORMATION: Designed synthetic linear glycopeptide
      containing a saccharidic B-cell epitope and a CD4+ T-cell epitope
      able to induce anti-saccharidic antibodies
<220> FEATURE:
<221> NAME/KEY: MISC_FEATURE
```

```
<222> LOCATION: (1)..(3)
<223> OTHER INFORMATION: alpha-N-acetylgalactosamine (GalNAc)-D-Serine

<400> SEQUENCE: 23

Ser Ser Ser Lys Leu Phe Ala Val Trp Lys Ile Thr Tyr Lys Asp Thr
1               5                   10                  15

<210> SEQ ID NO 24
<211> LENGTH: 22
<212> TYPE: PRT
<213> ORGANISM: ARTIFICIAL SEQUENCE
<220> FEATURE:
<223> OTHER INFORMATION: Designed synthetic linear glycopeptide
      containing a saccharidic B-cell epitope and a CD4+ T-cell epitope
      able to induce anti-saccharidic antibodies
<220> FEATURE:
<221> NAME/KEY: MISC_FEATURE
<222> LOCATION: (1)..(1)
<223> OTHER INFORMATION: alpha-N-acetylgalactosamine (GalNAc)-Serine
<220> FEATURE:
<221> NAME/KEY: MISC_FEATURE
<222> LOCATION: (2)..(3)
<223> OTHER INFORMATION: alpha-N-acetylgalactosamine (GalNAc)-Threonine
<220> FEATURE:
<221> NAME/KEY: MISC_FEATURE
<222> LOCATION: (4)..(4)
<223> OTHER INFORMATION: alpha-N-acetylgalactosamine (GalNAc)-Glycine
<220> FEATURE:
<221> NAME/KEY: MISC_FEATURE
<222> LOCATION: (5)..(5)
<223> OTHER INFORMATION: alpha-N-acetylgalactosamine (GalNAc)-Serine
<220> FEATURE:
<221> NAME/KEY: MISC_FEATURE
<222> LOCATION: (6)..(7)
<223> OTHER INFORMATION: alpha-N-acetylgalactosamine (GalNAc)-Threonine
<220> FEATURE:
<221> NAME/KEY: MISC_FEATURE
<222> LOCATION: (8)..(8)
<223> OTHER INFORMATION: alpha-N-acetylgalactosamine (GalNAc)-Glycine

<400> SEQUENCE: 24

Ser Thr Thr Gly Ser Thr Thr Gly Lys Leu Phe Ala Val Trp Lys Phe
1               5                   10                  15

Ile Thr Tyr Lys Asp Thr
            20

<210> SEQ ID NO 25
<211> LENGTH: 17
<212> TYPE: PRT
<213> ORGANISM: ARTIFICIAL SEQUENCE
<220> FEATURE:
<223> OTHER INFORMATION: Designed synthetic linear glycopeptide
      containing a saccharidic B-cell epitope and a CD4+ T-cell epitope
      able to induce anti-saccharidic antibodies
<220> FEATURE:
<221> NAME/KEY: MISC_FEATURE
<222> LOCATION: (1)..(1)
<223> OTHER INFORMATION: alpha-N-acetylgalactosamine (GalNAc)-Serine
<220> FEATURE:
<221> NAME/KEY: MISC_FEATURE
<222> LOCATION: (2)..(3)
<223> OTHER INFORMATION: alpha-N-acetylgalactosamine (GalNAc)-Threonine

<400> SEQUENCE: 25

Ser Thr Thr Gln Tyr Ile Lys Ala Asn Ser Lys Ile Gly Ile Thr Glu
1               5                   10                  15

Leu
```

MULTIPLE ANTIGEN GLYCOPEPTIDE CARBOHYDRATE VACCINE COMPRISING THE SAME AND USE THEREOF

PRIOR APPLICATIONS

This application is a continuation-in-part of U.S. patent application Ser. No. 09/049,847 filed Mar. 27, 1998 which is based on provisional patent application Ser. No. 60/041,726 filed Mar. 27, 1997.

TECHNICAL BACKGROUND

1. Field of the Invention

The present invention is directed to the field of immunotherapy and more particularly to a glycoconjugate, a composition and vaccine comprising the same and to the use thereof for enhancing the immune response and notably in cancer therapy and in therapeutic of infection caused by pathogenic agent against whom a humoral or a cellular immune response is necessary. The invention relates also to a diagnosis kit and a method for diagnosis of cancer.

2. Prior Art/Relevant Literature

As a result of aberrant glycosylation, cancer-associated carbohydrate antigens are exposed at the surface of tumor cells whereas they are hidden in normal cells (Bhavananda, et al. (1991)). Recent advances in immunology and in the identification of tumor specific antigens have renewed the interest for the development of cancer vaccines, and these exposed glycosidic B-cell epitopes have been considered as attractive targets for immunotherapy named "Active Specific Immunotherapy" (ASI) by Longenecker (MacLean et al; (1994)). This approach involves immunization with a defined antigen to elicit a specific immune response to that antigen and could represent an alternative to the conventional cancer therapies.

Among the large number of known tumor markers, the Tn ($\alpha$-GalNAc-Ser/Thr), the T* ($\beta$-Cal-(1→3)-$\alpha$-GalNAc Ser/Thr) and the sialosyl-Tn ($\alpha$-NeuAc-(2→6)-$\alpha$-GalNAc-Ser/Thr) antigens have been extensively studied since they are expressed on mucin-type glycoproteins by the majority of adenocarcinomas (Springer et al. (1984). Indeed, several studies have shown some protection against tumors after immunization with these glycosidic antigens, in experimental or clinical studies. These tumour associated carbohydrates are relevant markers for cancer diagnostic and prognosis (Itzkowitz et al. (1990)). Using desialylated red blood cells, which are rich in T and Tn determinants, Springer observed a long-term effective protection against recurrence of human breast carcinoma (Springer et al. (1995), Springer et al. (1994). An other group investigated the potential of ASI with desialylated ovine submaxillary mucin (d-OSM), which contains high density of the Tn epitope; their studies showed that this antigen provided a good protection and a long-term survival in mice with mammary carcinoma (Singhal et al. (1991)). Partially d-OSM also gave efficient protection against human colon carcinoma (O'Boyle et al. (1992)). Ratcliffe et al. were the first to use a synthetic tumor-associated antigen, a T antigen-protein conjugate, to stimulate an efficient immune response in rabbits (Ratcliff et al. (1981)). Thereafter Longenecker extensively studied similar synthetic carbohydrate hapten conjugates and found that they induce an increased survival of mice grafted with mammary carcinoma cells (Fung et al. (1990)), and of patients with ovarian cancers (MacLean et al. (1992)). Similar studies of the same group have further shown an increased protection of patients suffering from breast cancer (Longenecker et al. 1993)) or melanoma (Helling et al. (1995)) after respective administration of sialosyl Tn or the GM2 ganglioside-protein conjugates. On the other hand, Toyokuni et al. generated an anti-tumor antibody response in mice after immunization with a Tn antigen coupled either to OSA (Ovine Serum Albumin) or to a synthetic lipopeptide (Toyokuni et al. (1994)). This last result was interesting since it was the first example of a small synthetic carbohydrate antigen that generates an Immune response against a tumor associated carbohydrate antigen, without the use of a macromolecular carrier or adjuvants.

These studies suggested that carbohydrate antigens are appropriate candidates for anti-tumor vaccine development. However, carbohydrate antigens do not possess T-cell epitope and therefore induce only weak T cell-independent antibody response. Several approaches have been explored to increase the immunogenicity of such carbohydrates. The use of biological material which expresses clusters of antigens on a protein backbone (like desialylated red blood cells or OSM) is a possibility. But the most widely used approach is to conjugate the carbohydrate to a carrier protein, such as Bovine serum albumin (BSA) or Keyhole limpet hemocyanin (KLH).

Although these immunogens have shown some promise, protein carriers display major disadvantages. The grafted epitope represents only a small part of the total conjugate and it is distributed at random on the carrier surface. Therefore, immune responses to the carrier molecule may result in a low level of the desired antibodies as compared to the total amount of antibodies produced. Moreover, these conjugates present ambiguity in both composition and structure and they do not always induce reproducible immune response. Recent advances in the total synthesis of oligosaccharides expressed by tumour cells (Deshpande et al. (1997), Sames et al. (1997)) open new possibilities for such achievement. However, haptenic molecules such as carbohydrates require their association in more complex structures to stimulate immune responses. The use of traditional protein conjugates raises the problem of hapten-specific suppression (Herzenberg et al. (1980), Schutze et al. (1985)), and their poorly defined chemical composition and structure may limit their efficacy.

Until now, as for chemically refined structures dendrimeric poly-lysine backbones, which will be described in more detail later in the present specification, have been widely used for presenting peptides (Tam et al., 1994). However, to our knowledge, there is only one preliminary attempt of their utilisation for presenting carbohydrates to the immune system (Roy et al., 1994). This latter reference teaches the synthesis of three sialylated multiple antigen peptides having tetanus toxin T-cell epitopes. A similar strategy was also recently published (Lett, et al. (1995), CHONG et al.,1997) where the authors couple mixtures of natural or synthetic polysaccharides to a Multiple Antigenic Peptidic system.

Thus, there still exist a need for a new conjugate circumventing the drawbacks mentioned above of the prior art constructions which has a chemically defined structure, is capable of stimulating both the antibody response and the T response when administered in a human or animal body, while avoiding undesired immune responses.

SUMMARY OF THE INVENTION/PREFERRED EMBODIMENTS

Accordingly, the present invention is generally directed to a carbohydrate peptide conjugate comprising:

a carrier comprising a dendrimeric poly-Lysine enabling multiple epitopes to be covalently attached thereto, at least one peptide comprising one T epitope or several identical or different T epitopes at least one carbohydrate moiety containing B epitope, provided it is not a sialoside, or several identical or different B epitopes.

The peptide comprising the T epitope(s) can be bound to a lysine of said carrier, as the carbohydrate moiety containing B epitope(s).

This approach for presenting epitopes is herein referred to as the Multiple Antigen Glycopeptide (MAG). The conjugate of the present invention is notably useful for enhancing the antibody response in a human or animal body to which it has been administered and in particular as a vaccine.

Moreover, since a multiple antigenic O-linked glycopeptide (MAG), according to the present invention, carrying for example the carbohydrate Tn antigen associated with a $CD4^+$ T cell epitope was shown able to induce anti-Tn IgG antibodies which recognize human tumour cell lines, accordingly the present invention also concerns an composition capable of increasing the survival of a tumour-bearing human or animal. A therapeutic immunisation protocol performed with this fully synthetic immunogen increased the survival of tumour bearing mice.

More particularly the present invention is directed to a carbohydrate peptide conjugate comprising:

at least 3 lysine residues covalently bound to each other, at least one peptide comprising a T epitope bound to a lysine residue, and at least one carbohydrate moiety containing epitope B, optionally substituted, covalently linked to the end of said peptide opposite to lysine, and with the proviso that said carbohydrate moiety is not a sialoside radical.

According to another embodiment of the invention, the conjugate comprises:

at least one peptide comprising one T epitope, or several identical or different T epitopes, and at least one carbohydrate moiety, or a derivative thereof, containing B epitope, provided it is not sialoside, or several identical of different epitopes.

In a further embodiment of the invention, the carbohydrate peptide conjugate is linear.

Another object of the present invention is a pharmaceutical composition comprising the conjugate of the present invention.

A further object of the present invention is a vaccine comprising the conjugate according to the present invention.

A still further object of the present invention is a method of enhancing the immune response of a human or animal body, in particular B and/or T-cell responses, wherein the conjugate according to the present invention is administered to said human or animal body.

Another object of the present invention is a method of inducing B-cell responses against saccharidic epitopes in a human or animal body, wherein the conjugate according to the invention is administered to said human or animal body.

A still further object of the present invention is a method of vaccination of a human or animal body wherein the conjugate according to the present invention is administered to said human or animal body.

Another object of the present invention is a diagnosis kit comprising antigen specific antibodies elicited by immunization of a human or animal body with a composition according to the present invention.

A further object of the present invention is a method of diagnosis of cancer wherein a biological sample is brought into contact with at least one of these antibodies and wherein one determines the formation of complexes between this antibody and molecules comprised in the said sample.

A still further object is an immunogenic composition as described hereabove, capable to elicit an immune response against a viral infection caused by a pathogen such as hepatitis virus, HIV or CMV.

The present invention will now be described in details in the following description with reference to the drawings below.

DETAILED DESCRIPTION

Definitions and Abbreviations

Figure 1:
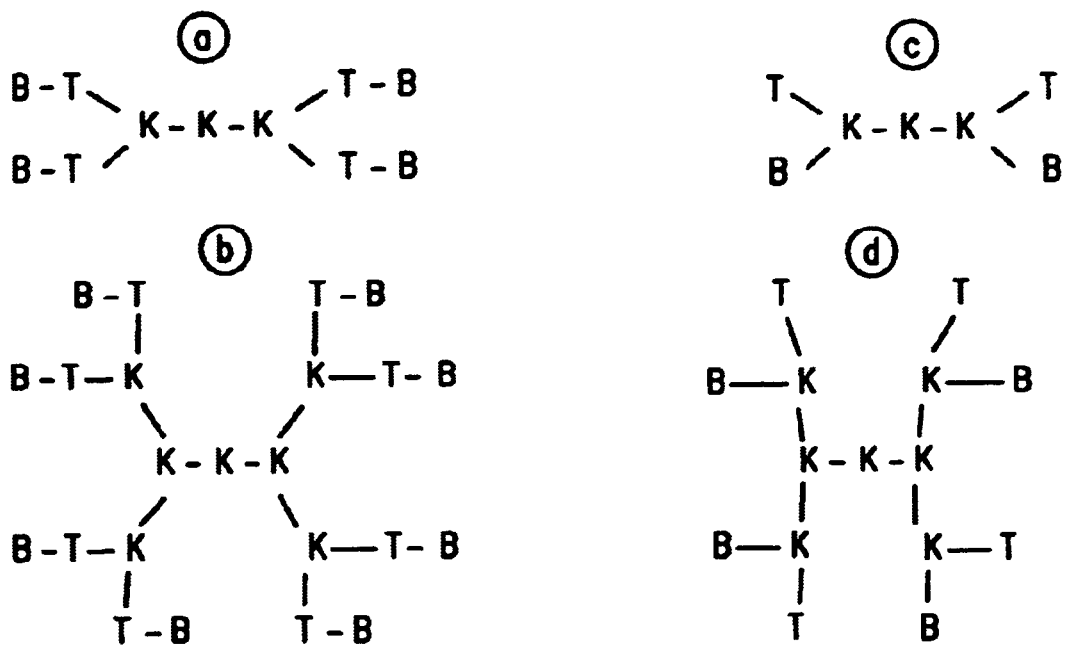
FIG. 1 is a schematic representation of a MAG compounds (B4-T4-M, B8-T8-M, B2-I2-M and B4-T4-M (with different organization of T and B epitopes) (a to d), tri-Tn(e) and hexa-Tn(f) according to the present invention.
Figure 1:
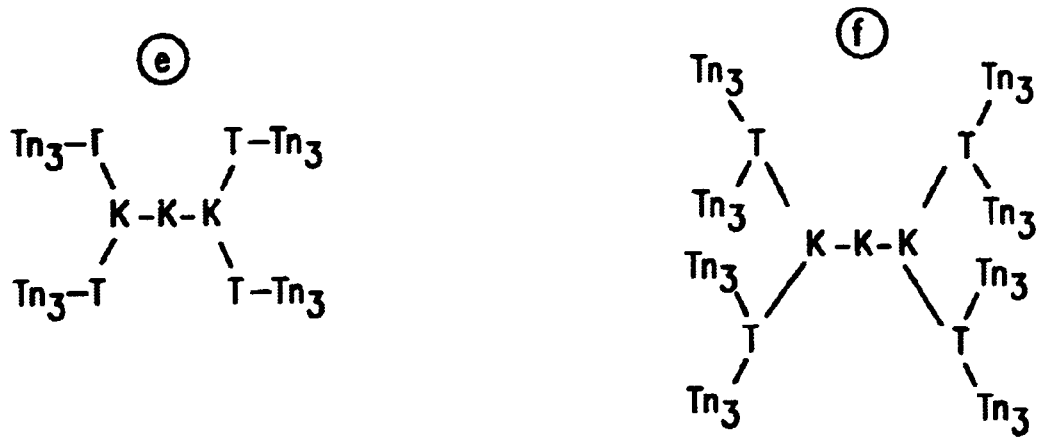
Figure 2A:
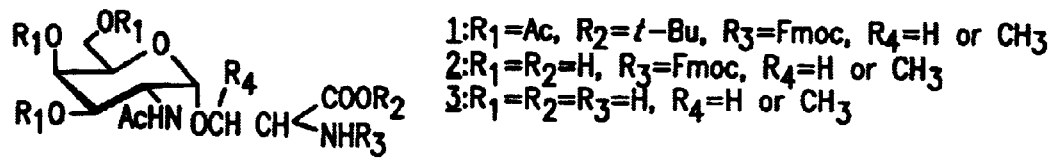
FIG. 2 depicts the Tn antigen and its derivatives.
Figure 2B:
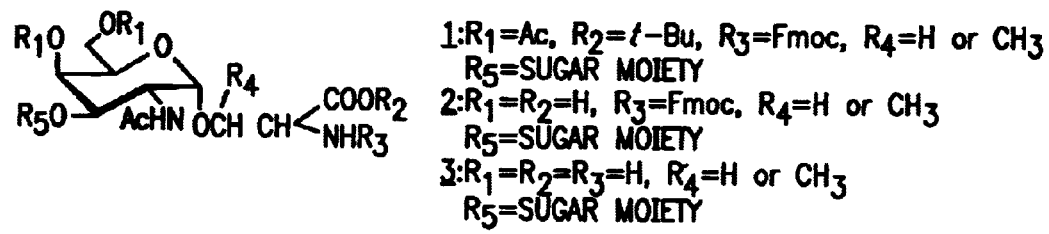

Antigens:

The expressions carbohydrate B antigen, B epitope, B-cell antigen. B-cell epitope are used herein to designate in general glycosidic antigens capable of eliciting a B-cell response, the antigens consisting of sialosides being excluded.

By T antigen or T epitope, T-cell antigen, T-cell epitope is meant an antigen generally of a peptidic nature capable of eliciting a T cell response.

Synthetic compounds B-1, M, B4-M, I4-M and B4-T4-M were also used as antigens (see Table 2 hereafter).

A T antigen is named T in Tables 1 and 2 and may be a PV antigen of Tables 3 and 4.

A B antigen is named B in Tables 1 and 2 and may be a Tn antigen of Tables 3 and 4.

The B-T structure of Tables 1 and 2 may be the GP:Tn-PV of Tables 3 and 4.

<<B4-M>> or <<B4-MAP>> of Tables 1 and 2 may be the MAG:Tn of Tables 3 and 4.

<<T4M>> or <<T4-MAP>> of Tables 1 and 2 may be the MAP:PV of Tables 3 and 4.

<<B4-T4-M>> or <<B4-T4-MAP>> of Tables 1 and 2 may be the MAG:Tn-PV of Tables 3 and 4.

The abbreviation M as used herein is an example of MAP (Multiple antigen peptide and designates the following structure:

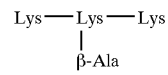

Where appropriate, the universal one letter code for aminoacids was used herein (K for lysine. etc.).

Other Abbreviations Also Used in the Present Invention:

BSA, bovine serum albumin; OSA, ovine serum albumine; Ova, ovalbumin; OSM, ovine submaxillary mucin; d-OSM, desialylated ovine submaxillary mucin; ES MS, electrospray mass spectrometry; Fmoc, Fluoren-9-yl-methoxycarbonyl, PBS, phosphate buffered saline; AgOTf, trimethylsilyl trifluoromethne sulfonate: $Ag_2CO_3$, silver carbonate; $AgClO_4$, silver perchlorate; a OSM, asialo ovine submaxillary mucin; CFA, Complete Freund Adjuvant; DIEA, diisopropylethylamine; ESMS, electrospray mass spectroscopy; FCS, Fetal Calf Serum; FITC, Fluorescein Isothiocynate; Fmoc, 9-fluorenylmethoxycarbonyl; HOBT, 1 hydroxybenzotriazole; IFA, Incomplete Freund Adjuvant; PE, phycoerythrin; PFA, paraformaldehyde; pfp, pentafluorophenyl: PV, Poliovirus; TBTU, 2-(1H-benzotriazole-1-yl)-1,1,3,3-tetramethyluronium tetrafluoroborate; TFA, trifluoroacetic acid; TT, Tetanus toxin; Fmoc, N-(9-fluorenyl) methoxycarbonyl: KLH, beyhole limpet hemocyanin.

The expression <<antibody response>>, <<B or B-cell response>> are used indistinctively herein. The same applies to <<cellular response>>, <<T or T-cell response>>.

The present invention is directed in its primary aspect to a carbohydrate peptide conjugate comprising:

an appropriate carrier based on a dendrimeric poly-Lysine enabling multiple epitopes to be covalently attached thereto, at least one peptide comprising one T epitope or several identical or different T epitopes, at least one carbohydrate moiety containing B epitope, provided it is not a sialoside or several identical or different B epitopes.

Several identical T or B epitopes means between two to eight of the same epitope.

Several different T epitopes means between two to eight of T epitopes from different origin.

Several different B-epitopes means between two to eight of B-epitopes from different origins.

The poly-Lysine core of the present conjugate is called a dendrimer because it may be represented (FIG. 1) as a star with multiple branches all substantially identical.

As stated earlier, multiple antigen peptide system have been described in 1988 by Tam et al. (1988) that are based also on certain dendrimeric structure in which peptidic antigen are covalently conjugated to the branches of the latter.

Examples of suitable carriers comprise those having a structure based on a poly-Lysine core forming a multiple branches star, such as, for example a 8 or 4 branches star.

Thus the present invention in one of its preferred embodiment is directed to a conjugate comprising a dendrimeric structure based on a poly-Lysine core forming a 4 branches star, with an epitope T covalently bound to each of the branches and associated to a carbohydrate moiety (provided it is not a sialoside radical) containing an epitope B.

According to a further preferred embodiment of the present invention the multiple antigen glycopeptide (MAG) forming the conjugate according to the present invention comprises at least 3 lysines and up to 15 lysines residues covalently linked to one another. Most preferably the present conjugate comprises 3 lysines.

In a preferred embodiment, to the NH2 end of each lysine residue is bound at least one peptide comprising one epitope T bound to a lysine and at least a carbohydrate residue, being not a sialoside, optionally substituted, covalently bound to the end of said peptide opposite to the lysine and forming a B epitope.

In another preferred embodiment, to the $NH_2$ end of each lysine residue is bound at least one carbohydrate residue, being not a sialoside, optionally substituted and forming a B-epitope bound to a lysine and at least a peptide comprising one T-epitope covalently bound to the end of said carbohydrate opposite to the lysine.

The MAG structure referred to herein will be better understood by reference to FIG. 1.

In FIG. 1 are schematically represented examples of a 4 to 8 branches star comprising from 3 to 7 lysines bearing 4 to 8 aminogroups bound to desired epitopes (epitopes B, optionally substituted with a peptide and epitopes T). This structure provides a high density of the antigens at the surface of the lysine core.

Moreover this structure offers several advantages. First, the carbohydrate content is much higher in the MAG system (usually over 90%) than in the traditional protein conjugates. This structure of high density glycopeptide antigens induce higher antibody responses confirming the previous observation comparing an MAP system to the same antigens covalently linked to a carrier protein (J. P. TAM et al (1988) and J. P. TAM (1994)).

A further advantage of the MAG is that the core matrix representing a minor fraction of the total construct has a low immunogenicity, thus avoiding undesired immune responses (Posnett et al. (1988)). Another advantage of the present construct is that the resulting synthetic immunogen has a well defined chemical structure.

The presence of both carbohydrate B epitopes and T epitopes on the glycoconjugate of the present invention renders the latter an efficient immunogen as will be demonstrated later in the experimental section.

The carbohydrate moiety, containing the epitope B of the conjugate according to the present invention, may originate, for example, from tumor (cancer) glycosidic antigens of:

the glycolipid class, including acidic glycolipid such as, for example, gangliosides GD2, GD3 and GM3 (melanoma) and neutral glycolipids such as, for example, the Lewis$^y$ (Le$^y$) (breast, prostate, ovary) and the Globo H (breast, prostate, ovary) antigens. The sialylated derivatives belonging to this class are excluded.

the O-glycosyl peptides (or aminoacid) class such as, for example, the Tn antigen ($\alpha$GalNAc-Ser or $\alpha$Gal NAc-Thr). T* antigen ($\beta$-Gal-(1–3)-$\alpha$-GalNac-Ser or $\beta$Gal (1–3)$\alpha$Cal-NAc-Thr), two tumor markers frequently present in carcinomas but not usually in normal tissues [Springer G. F. Science 224, 1198–1206 (1984)] (ovary, breast, lung), or di-Tri ($\alpha$ GalNAc-Ser/Thr)$_2$, tri-Tn($\alpha$ GalNac-Ser/Thr)$_3$ or hexa-Tn($\alpha$GalNAc-Ser/Thr)$_6$.

The epitope B of the conjugate according to the present invention may also originate from capsular bacterial polysaccharides of, for example, *Neisseria meningitis, Haemophilus influenzae, Streptococcus pneumoniae,* and of the Streptococcus group, with the exception of the sialylated polysaccharides.

The polysaccharides are carbohydrate residues obtained by synthetic process.

The epitope B of the present conjugate may be also of fungal origin, such as for example, one isolated from the yeast Saccharomyces.

The B epitope of the conjugate according to the present invention are preferentially tumor markers, such as, for example, Tn and T* antigens.

The preferred carbohydrate moiety forming the B epitope of the conjugate according to the present invention may be comprised of a galactosyl residue, or a derivative thereof, being not sialylated.

It can be selected from the group comprising Tn, di-Tn, tri-Tn, hexa-Tn, or T* antigens.

Thus in one of its preferred embodiment the invention relates to a carbohydrate peptide conjugate comprising:

at least 3 lysine residues covalently bound to each other.

at least one peptide comprising a T epitope bound to a lysine residue, and at least one glycosidic residue, optionally substituted, covalently linked to the said peptide and forming epitope B with the proviso that said carbohydrate moiety is not a sialoside radical.

In a related aspect of this embodiment the galactosyl residue is substituted by another glycosyl residue.

In a related aspect, the conjugate of the present invention comprises 3 lysine residues, at least 4 epitopes of the T type, which may be the same or different linked to the $NH_2$ ends of 2 of the lysine residues, and 4 $\alpha$-galactosyl-Nacetyl-Serine residues.

The carbohydrate moiety of the conjugate of the present invention may further be grafted on the dendrimeric structure in combination with one or more tumor peptidic CD8$^+$ T cell epitopes recognized by tumor-specific cytotoxic T cells. These peptidic CD8+ T cell epitopes recognized as tumoral markers may be selected in the group consisting of:

MUC-1 peptides (pancreas, breast)

MAGE 1 and 3 (melanoma, lung) (T. Boon et al. (1996), Immunology Today, vol. 16 n°7, pp 334–336)

pme117/gp 100 (melanoma)

Tyrosinase (melanoma)

BAGE (melanoma)

GAGE (melanoma)

LB-33-B (melanoma)

CDK4 p185$^{HER}$ (breast, ovary)

CEA

MART1/Melan-A (melanoma)

or selected in the group consisting of tumor antigens described in A. Van Pel et al. (1995) Immunological. Reviews n° 145, pp 229–250 or in P. G. Coulie (1995), Stem Cells. 13. pp 393–403.

As mentioned earlier, in the conjugate of the present invention a CD4+ T epitope is conjugated to a carbohydrate B epitope described above to elicit an efficient immune response.

Such an epitope can comprise between almost 5 and 50 aminoacids.

One such preferred T epitope is the CD4+, I epitope which is the synthetic peptide that corresponds to the 103–115 sequence of VP1 protein from poliovirus type 1 or alternatively it may be a peptide comprising the CD4+, T epitope selected from the group comprising:

fragments of the Tetanus toxin such as, for example:
830–844 sequence of the tetanus toxin (QYIKANSKFIGITEL), (SEQ ID No: 1)
947–967 sequence of the tetanus toxin (FNNFTVSFWLRVPKVSASHLE), (SEQ ID No: 2)
1273 sequence of the tetanus toxin (GQIGNDPNRDIL), (SEQ ID No: 3)

These peptidic T epitopes typically bind to a plurality of MHC (Major Histocompatibility Complex) human and murine molecules of class II avoiding in consequence the restriction problems encountered with the CD4+, T cellular response, associated with the polymorphism of the MHC molecules existing between individuals. Moreover the use of tetanus toxin peptides should increase the immunogenicity of antigens present on the conjugate of the present invention, as a result of the vaccination of numerous individuals with the tetanus toxoid.

According to another embodiment of the invention, the conjugate comprises:

at least one peptide comprising one T epitope, or several identical or different T epitopes, and at least one carbohydrate moiety, or a derivative thereof, containing B epitope, provided it is not sialoside, or several identical of different epitopes.

Said conjugate can be Tn3-T or Tn6-T where T is any CD4+ T epitope, such as the PV peptide, the tetanus toxin peptide or PRADE peptides epitopes.

They can be obtained by peptidic synthesis; wherein a peptidic bound is created between the glycosylated serine, or threonine, and the peptide T.

Inventors have carried out the synthesis of linear glycopeptides that are described in table 3 of example 9. The synthesis of these linear glycopeptides was performed with Tn motifs associated to the CD4+ T
cell epitope to the poliovirus (PV:KLFAVWKITYKDT), (SEQ ID No: 4).

The Tn antigen was introduced in 1, 3 or six copies and was located either in the middle or at the end of the peptides sequence. The antigenicity and the immunogenicity of the resulting glycopeptides have been investigated and the results are presented in example 10. Since D-aminoacids are known to confer proteolytic stability, D-(Tn$_3$-PV glycopeptide has been synthetized in order to evaluate the effect of a D-aminoacid on the antigenicity and immunogenicity of this peptide (D-(Tn$_3$) represents three consecutive D-serine α-linked to a galNac residue). The threonine was replaced in tho 3-D-(Tn3) motif by D-serine, since its β-chiral center might confer additional structural problems.

As detected by the results presented in example 10, the inventors have now shown that linear glycopeptides comprising both at least one T-cell epitope and a Tn antigen, a T* antigen or a Tn antigen derivative, in one or multiple copies, are able to induce antibodies raised against the carbohydrate moiety.

Consequently, the invention also concerns a linear carbohydrate peptide conjuguate comprising:

at least one peptide comprising one T epitope or several identical or different T epitopes, and at least one carbohydrate moiety, or derivative thereof, containing a B-epitope provided it is not a sialoside.

In a first embodiment of the linear carbohydrate peptide conjuguate described above, the peptide and the carbohydrate moiety are directly covalently bound within the molecule.

In a second embodiment of the linear carbohydrate peptide conjugate of the invention, the peptide and the carbohydrate moiety are linked via a spacer.

In a first aspect, the spacer consists of an aminoacid chain. This aminoacid chain may have an aminoacid lenght of 1 to 5 aminoacids.

In a second aspect, the spacer consists of a carbohydrate residue or of a chain of multiple carbohydrate residues.

The spacer can be also an aliphatic chain (1 to 10 carbon atoms).

Most preferably, the carbohydrate moiety comprised in the carbohydrate peptide conjugate described above is selected from the group consisting of 1 to 6 residues of a Tn antigen, or a Tn antigen derivative.

These linear carbohydrate peptide conjuguates according to the invention have been successfully used to induce a high level of antibodies specific to the carbohydrate moiety, and particularly to the Tn carbohydrate moiety which mimic a tumoral cell antigen.

Thus these linear carbohydrate peptide conjuguates can be used in immunotherapy methods against cancer.

As stated earlier the invention is also directed to a pharmaceutical composition comprising a conjugate according to the present invention. Such composition comprises an effective amount of the present conjugate for example in a pharmaceutically acceptable vehicle and may be of liquid or emulsion form, in the presence or not of an adjuvant (including aluminium hydroxyde and cytokines). The route of administration of the said composition may be any of usually used route (including intra-tumoral administration such as injection). The said immunogenic composition, comprising at least one carbohydrate peptide conjugate, wherein said conjugate comprises various carbohydrate antigens can be used to induce a more efficient anti-tumour immunity against cancers.

The amount of conjugate can be comprised between 10 ng and 1 ng.

The present invention is also directed to a vaccine comprising a conjugate according to the present invention.

A further object of the present invention is a method of enhancing the immune response of a human or animal body, notably the T- and/or B-cell mediated response, in particular against bacteria, wherein the conjugate of the present invention is administered to said human or animal body.

A still further object of the present invention relates to a method of inducing a B-cell response in a human or animal body wherein at least one conjugate according to the invention is administered.

The invention also relates to a method of inducing a B-cell response in a host characterized in that in said host is administered at least one carbohydrate peptide conjugate comprising:

at least 3 lysine residues covalently linked to one another,
at least one peptide comprising a T epitope linked to a lysine residue, and
at least one carbohydrate moiety optionally substituted, being not a sialoside.

Another object of the present invention concerns a method of vaccination of a human or animal body wherein a conjugate according to the present invention is administered to said human or animal body.

A still further object of the present invention is a diagnosis kit comprising antigen specific antibodies elicited by immunization of a human or animal body with a composition according to the present invention.

Such antibodies are also considered as subjects of the present invention. They can be used in a method of diagnosis of cancer comprising bringing into contact at least one of these antibodies with a biological sample and determining the formation of complexes between this antibody and molecules comprised in this sample.

The inventors have now also demonstrated that the saccharidic moiety of the glycopeptides according to the invention is endowed with an adjuvant biological activity. This surprising property permits both an enhancement of the immunological response towards the antigen(s) included within the structure of the glycopeptide and a targeting of said glycopeptide to the suitable antigen presenting cells (APC), and more particularly to the macrophages, the dendritic cells as well as the B cells. A limited number of cells, such as dendritic cells (DC), monocytes/macrophages (MP) or B lymphocytes, express MHC class II molecules and are able to act as professional antigen presenting cells (APC) to stimulate CD4$^+$ T cell response. This process needs that APC internalize antigenic molecules, such as protein or polypeptides, which after mild proteolytic degradation leads to the expression of MHC class II molecules carrying peptides resulting from the enzymatic degradation of the antigen. When APC are fed with glycopeptides or dendrimeric multiple antigenic glycopeptides containing the N-acetyl D-Galactosamine (GalNac) saccharidic moiety, we observed an enhancement of the T cell response specific for the peptide, as measured by the stimulation of a specific T cell hybridoma. The consequence of this increase in the T cell response is that the amount of antigenic molecules used to feed APC in order to stimulate T cells is decreased by 10-to 10000 fold (depending on the number of the GalNAc saccharidic moieties) compared to the same antigenic structure devoid of GalNac. This phenomenon was observed with different professional APC, such as in vitro differentiated DC, activated MP or activated B cells, but not with non-professional APC, such as a fibroblast L cell line transfected with the appropriate MHC class II molecules. This indicates that there exists a cell type selectivity of the observed increased of T cell stimulation associated with the GalNac moiety. One hypothesis would he that professional APC endocytose GalNAc-antigens much more efficiently because they express a receptor for GalNAc or galactosyl derivatives. Effectively, a 100 fold increase of T cell stimulation was already reported when APC are pulsed with mannosylated antigen due to mannose receptor mediated endocytosis of antigen.

The results of example 11 with the <<Tn-CD4$^+$ T-cell epitope>> conjuguates have established that Tn antigen consists of a targeting device for improving CD4$^+$ immune responses.

Thus, the conjugation of Tn epitope (a) to peptide or protein antigen can cause a selective targeting and a subsequent enhanced presentation by the antigen presenting cells (APC) which is strongly expected to result in better antigen specific immune response.

Thus, the invention also concerns a method for enhancing a T-CD4$^+$ immune response against an antigen within a human or animal body, wherein anyone of the conjuguate according to the invention disclosed above is administered to said human or animal body.

Figure 16:
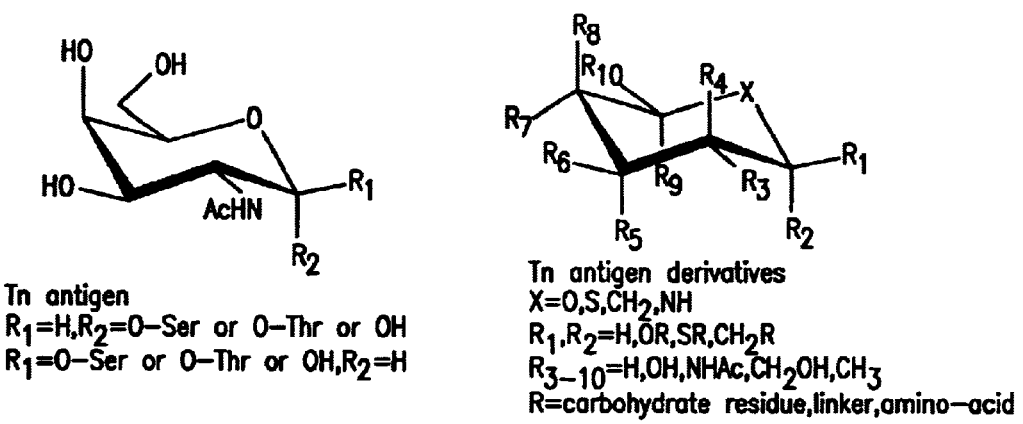
FIG. 16 Schematic representation of Tn and derivatives

In this specific embodiment of the invention, the Tn antigen is selected in the group consisting of α-GalNAc, α-GalNAc-Ser, α-GalNAc-Thr, β-GalNAc, β-GalNAc-Ser and β-GalNAc-Thr as well as the Tn derivatives, as represented in FIG. 16.

Figure 17A:
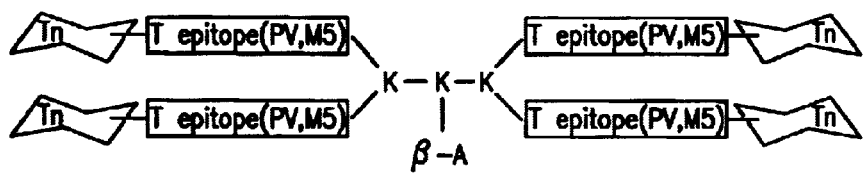
FIG. 17 Schematic representation of MAG constructs

In a typical embodiment, the carbohydrate peptide conjuguate used in the above method for enhancing a T-CD4$^+$ immune response against the antigen is a MAG construct as represented in table 4 and in FIG. 17a.

Figure 17B:
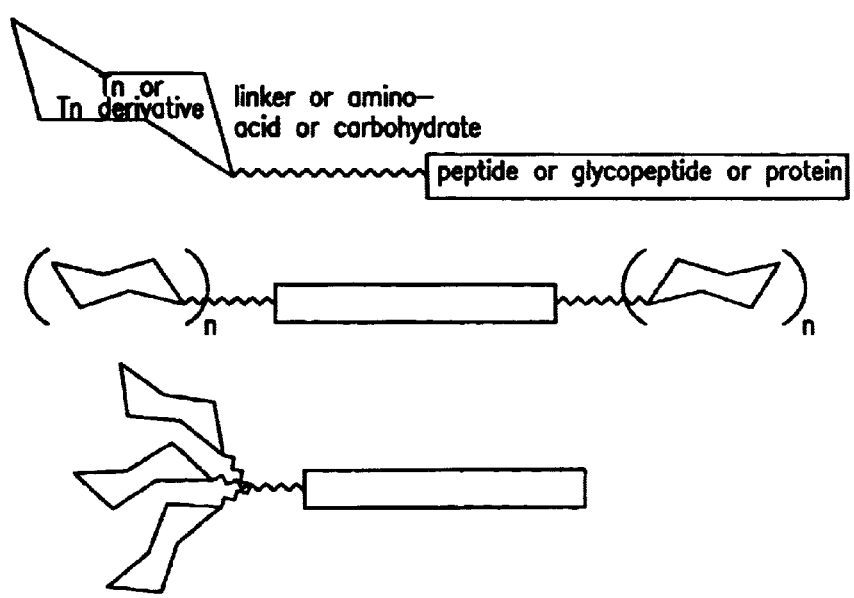

In another typical embodiment, the carbohydrate peptide conjuguate can also be a linear construct or other type of multimers as represented in FIG. 17b.

In a still further embodiment, the adjuvant properties of the carbohydrate moiety of a conjugate according to the invention allows the use of said conjugate to prime efficiently a cytotoxic T cell response because they provide an efficient T cell help.

For the same reasons, a conjugate according to the invention may also be used to pulse dendritic cells in vitro to prime antigen-specific CD4$^+$ and CD8$^+$ T cells in vivo and to induce protective immunity.

In the specific embodiment described above, a carbohydrate peptide conjugate according to the invention is administered in combination with at least one peptide comprising a cytotoxic T cell (CTL) epitope.

Alternatively, one or several peptides comprising at least one cytotoxic T cell (CTL) epitope are included within the structure of the conjugate.

Consequently, the invention also concerns an immunogenic composition comprising a carbohydrate peptide conjugate, such as defined therein, in combination with a peptide comprising at least one CTL epitope.

A further object of the invention consists of a carbohydrate peptide conjugate comprising:

at least one peptide comprising one T epitope or several identical or different T epitopes, wherein at least one T epitope consists of a cytotoxic T cell (CTL) epitope.

The invention also concerns a method for priming a cytotoxic T cell response in a human or animal body, wherein such a conjugate comprising at least one CTL epitope is administered to said human or animal body.

The invention further deals with a method for priming a cytotoxic T cell response in a human or animal body, wherein an immunogenic composition containing a carbohydrate peptide conjugate of the invention in combination with a peptide comprising at least one CTL epitope is administered to said human or animal body.

The CD4+T cell epitopes used might be selected from the peptides described hereunder:

Peptides a. CD4+ T cell epitope used in MAG

PV (poliovirus) sequence 103–115: KLFAVWKITYKDT (SEQ ID NO. 4)

-M5: NGKLIAYPIAVEALS (SEQ ID NO:5)

b. Example of "Universal" $CD4^+$ cell epitopes

-TT (tetanus toxin) derived T cell epitope such as sequence 830–844:

QYIKANSKFIGITEL (SEQ ID NO: 1) (Panina Bordignon, et al., 1989, Reece, et al., 1993)

PADRE (Pan DR T Helper epitope): a KXVAAWTL-KAAa (a=D-Ala,

X=L-cyclohexyl-Ala) (SEQ ID NO: 6) (Alexander, et al., 1994)

E7 P 20–29: TDLYCYEQLN (SEQ ID No: 7), E7 p 45–54: AEPDRAHYNI (SEQ ID No: 8), E7 p 60–79

:KCDSTLRLCVQSTHVIRTL, E7 p 85–94: GTL-GIVCPIC (SEQ ID No: 9), (Cornerford, et al, 1991) (SEQ ID No: 10), ras p 5–17: KLVVVGARGVGKS (SEQ ID No: 11), (Peace, et al)

neu p 42–56: HLDMLRHLYQGCQVV, (SEQ ID No: 12), neu p 783–797: (SEQ ID No: 13),

SRLLGICLTSTVQLV (Disis, et al, 1994),

MAGE-2121-134: LLKYRAREPVTAE (Chaux, et al, 199), (SEQ ID No: 14),

The present invention will now be illustrated in more details by the following examples and should not be intended to be limited thereto.

EXAMPLES

Example 1

Synthesis of the Glycoconjugate According to the Invention

The strategy for the construction of the MAG conjugate first involved the synthesis of the Tn antigen which represents the B cell epitope. This glycosidic tumor marker was then conjugated to a poly-lysine core (M) in association with the peptidic $CD4^+$, T cell epitope, giving the full construction B4-T4-M. In addition, the reference compounds which are necessary for the immunological tests were synthetized (B, T, B T, B4 M, T4 M, M).

The synthesis of the Tri antigen 2 (FIG. 2) was performed by classical methods (Ref. 19, Ref. 20) starting from tri-O-acetyl-D-galactal (Shafizadeh et al. (1989)). N (Fluorenylmethoxycarbonyl)-L-serine tert-butyl ester (Vowinkel et al. (1967), Schultz et al. (1993)) was used for the Koenigs-Knorr reaction with 3,4,6-tri-O-acetyl-2-azido-2-deoxy-b-D-galactopyranosyl chloride (Lemieux et al. (1979), Ferrari et al. (1980)), giving the protected derivative 1. The final deprotection of acetyl and of the t-butyl ester afforded Tn antigen 2 appropriately protected for the peptide synthesis.

B4-T4-M 4 was assembled by the conventional solid-phase peptide methodology (Bay et al. (1997)) using the Fmoc chemistry which is compatible with the glycopeptide synthesis. After attachment of the β-alanyl spacer on the Wang resin, the lysine core was constructed by coupling successively two levels of FmocLys(Fmoc)OH, providing four amino groups (Tam et al. (1988)). The lysine core was further elongated by the appropriately protected amino acids of the poliovirus (KLFAVWKITYKDT), (SEQ ID No: 4), T epitope sequence, four copies of the same amino acid being sequentially added. Ultimately 2 was incorporated to the dendrimeric peptide as a building block.

Of interest was the incorporation of the Tn antigen derivative 2 which could be achieved with the fully deprotected sugar. This is very advantageous since it avoids the eventual side reactions (racemization and/or β-elimination) associated with the final deacetylation of the sugar residue. A few examples of the use of unprotected glycosidic units have already been reported (Filira (1990)) (Reimer et al. (1993)). After completion of the synthesis, the MAG 4 was released from the resin with aqueous trifluoroacetic acid (95%) and the peptide side-chains were simultaneously deprotected. No glycosidic cleavage is usually observed over a reaction time of 1.5 hours (Paulsen et al. (1988), Jansson et al. (1990), Peters et al. (1992)). A similar procedure was followed for the reference compounds. All the peptides and glycopeptides were characterized by amino acid analysis and electrospray mass spectrometry.

General Methods:

For the synthesis of 2, reagents were purchased from Aldrich or Sigma. All the solvents were high grade and dry. $CH_2Cl_2$ was distilled over $P_2O_5$ and toluene over sodium with benzophenone, before use. For the peptide synthesis, Fmoc-protected amino acid derivatives and Wang resin were obtained from Bachem or Novabiochem. The side chain of the aminoacids were protected by a t-butyl group except for tryptophan and the lysine residues of the T-epitope which were protected by a t-butyloxycarbonyl (Boc) group. DMF and acetonitrile for HPLC were purchased from Merck. The final compounds were purified by reverse phase high performance chromatography (HPLC) using a Perkin-Elmer pump system with a UV detector (230 or 280 nm). A column (250×10 mm) of Nucleosil $C_{18}$ (5 mm, 300 Å) was used and the products were eluted with a gradient of MeCN/0.1% trifluoroacetic acid buffer during 20 min (flow rate 6 ml/min). $^1H$ NMR spectra (300,134 MHz, 3-(trimethylsilyl) propionic acid sodium salt as standard for spectra in $D_2O$) were recorded on a Bruker instrument. Mass spectra were measured by fast atom bombardment or by electrospray. Amino acid analyses were obtained using a Bookman 6300 analyser after hydrolysis of the peptides with 6 N HCl (0.2% phenol was added when the peptide contains a tyrosine residue) at 110° in sealed glass tubes for 20 h.

Solid Phase Synthesis, General Procedure:

The solid phase peptide and glycopeptide syntheses were performed manually using the standard Fmoc chemistry protocol (Bay et al. (1997)) on a polystyrene resin functionalized with p-benzyloxybenzyl alcohol (Wang resin). With the exception of the C-terminal β-alanine residue, the Nα-Fmoc amino acids (carrying standard side-chain protective groups) and the glycosylated building block 2 (3 equiv.) were incorporated to the peptide chain using TBTU as an activating agent and DMF as solvent. All the couplings were monitored by the Kaiser test (Kaiser et al. (1980)) and usually completed within 1 h. All Fmoc cleavages were carried out by treatment of the resin with 20% piperidine in DMF. Following each deprotection, the resin was successively washed with DMF, $CH_2Cl_2$, DMF. At the end of the synthesis, the resin was extensively washed with DMF and $CH_2Cl_2$, dried, and treated with an aqueous II-A solution for 2 h. After filtration of the resin, the solution was concentrated and the crude product precipitated with diethyl ether. The precipitate was filtered, dissolved in water and lyophilized. Peptides were purified on reverse phase HPLC (the elution conditions are indicated below, for each compound) and characterized by amino acid analyses and electrospray mass spectrometry.

Nα-(Fluoren-9-ylmethoxycarbonyl)-3-O-(2-acetamido-2-deoxy-α-D-galactopyranosyl)-L-serine 2:

Nα-(Fluoren-9-ylmethoxycarbonyl)-3-O-(2-acetamido-3,4,6-tri-O-acetyl-2-deoxy-α-D-galactopyranosyl)-L-serine tert-butyl ester 1 was prepared as previously described (Lemieux et al (1979), Ferrari et al. (1980)) by glycosylation of Nα-(Fluoren-9-ylmethoxycarbonyl)-L-serine tert-butyl ester (Vowimkel et al. (1967) Schultz et al. (1993)) with 3,4,6-tri-O-acetyl-2-azido-2-deoxy-p-D-galactopyranosyl chloride (obtained from tri-O-acetyl-D-galactal) (Shafizadseh et al. (1963)) using AgOTf as catalysts, followed by the reduction and acetylation of the 2-position (Paulsen et al. (1982)). The t-butyl ester of 1 (2 g, 2.8 mmol) was then deprotected in formic acid (76 ml) (Paulsen et al. (1989)). The solution was stirred for 10 h and evaporated. The residue was dissolved in MeOH (200 ml) and the acetyl groups of the sugar moiety were removed by adding, dropwise, a solution of 1% MeONa (pH 11) (Meinjohanns et al. (1995)). After 15 h, the medium was neutralized by a Dowex 50WX8 (H$^+$) resin and the final product 2 purified on a reverse phase column (C$_{18}$) using a gradient of water/MeCN 1.27 g (yield 79%).

Reference Compounds:

M: The MAG syntheses require a low substitution of the resin. The preformed symetrical anhydride of Nα-Fmoc βAla-OH (0.25 mmol) (Walker et al. (1994)) was reacted with the Wang resin (1 g, 0.96 mmol/g) for 1 h, yielding a functionalization of approximatively 0.12 mmol/g as estimated by UV analysis of a resin sample (Meienhofer et al. (1979)). After acetylation of the residual hydroxyl groups by AC$_2$O in DMF, the lysine core was assembled by sequential couplings of 0.48 and 0.96 mmol of Nα-Fmoc-Lys-(Fmoc)-OH. The cleavage of the peptide from the resin was carried out by TFA/water (95/5, 16 ml). The purification of the crude product by HPLC (gradient from 0% to 25%, 7.2 min retention time) gave M (94 mg). $^1$H-NMR (D$_2$O), d, 4.24, 4.03, 3.93 (3 CH a Lys), 3.54, 3.42 (CH$_2$—NH b-Ala), 3.22, 3 (CH$_2$ e Lys), 2.62 (CH$_2$—COOH b-Ala), 1.97–1.85 (2 CH$_2$ b Lys), 1.78–165 (2 CH$_2$ d, CH$_2$ b Lys), 1.58–1.3 (3 CH$_2$ g, CH$_2$ d Lys); ESMS: 473.2 (Calcd. 473.33).

The synthesis of the T epitope has been performed on 0.21 g of resin (0.15 mmol) by the general procedure. Cleavage of the resin-bound peptide (TFA/water/ethanedithiol: 95/2.5/2.5, 45 ml) and purification by HPLC (gradient from 0% to 65%, 12.6 min retention time) afforded T (31 mg). FABMS: [M+H]$^+$ 1613 (Calcd. 1611.9). Amino acid analysis: Ala 1.16 (1), Asp 1.03 (1), Ile 0.96 (1), Leu 1.01 (1), Lys 2.92 (3), Phe 1 (1), Thr 1.84 (2), Tyr 0.99 (1), Val 0.94 (1).

B-T: Further elongation of the T peptide chain (0.22 g resin, 0.14 mmol, synthesized as above) was achieved with 2 as a building block. The glycopeptide was released from the resin (TFA/water/ethanedithiol: 95/2.5/2.5, 50 ml) and the crude product purified by HPLC (gradient from 10% to 60%, 11.2 min retention time) yielding B-T (63 mg). ESMS: 1903 (Calcd. 1903.22). Amino acid analysis: Ala 1 (1), Asp 1.05 (1), Ile 1.0 (1), Leu 1.05 (1), Lys 3.12 (3), Phe 1.05 (1), Ser 0.94 (1), Thr 1.97 (2), Tyr 1.06 (1), Val 1.0 (1).

B4-M: 2 was conjugated to the poly lysine core (M) synthesized as described above (0.83 g resin, 0.1 mmol). After cleavage of the glycopeptide from the resin (TFA/water: 95/5, 25 ml), and purification by HPLC (gradient from 0% to 10%, 10.2 min retention time), B4-M was obtained (36 mg). ESMS: 1633.9 (Calcd. 1633.78). Amino acid analysis: Lys 3 (3), Ser 4.06 (4).

I4-M: The lysine core M (0.25 g resin, 0.03 mmol, synthesized as above) was further elongated by the T epitope sequence. The cleavage of the peptide from the resin (TFA/water/ethanedithiol: 95/2.5/2.5, 25 ml) and its purification by HPLC (gradient from 12% to 45%, 16.5 min retention time) gave I4-M (67 mg). ESMS: 6852.08 (Calcd. 6853.35). Amino acid analysis: Ala 4 (4), Asp 4.4 (4), Ile 4 (4), Leu 4.1 (4) Lys 15.8 (15), Phe 4 (4), Thr 8.2 (8), Tyr 4.3 (4), Val 3.8 (4).

Multiple Antigen Glycopeptide B4-T4-M:

The synthesis of B4-T4-M was achieved by ultimately coupling 2 to T4 M (0.25 g resin, 0.03 mmol) which was obtained as described above. Cleavage of the glycopeptide was accomplished with TFA/water/ethanedithiol (95/2.5/2.5, 30 ml). After purification by HPLC (gradient from 10% to 65%, 11.9 min retention time), the target glycopeptide was obtained (25 mg). ES MS: 8014.09 (Calcd. 8014.45). Amino acid analysis: Ala 4 (4), Asp 4.78 (4), Ile 4.09 (4), Leu 4.15 (4), Lys 16.31 (15), Phe 4 (4), Ser 3.81 (4), Thr 8.58 (8), Tyr 4.5 (4), Val 3.63 (4).

Example 2

Immunological Results: Antigenicity and Immunogenicity of T, CD4$^+$ Epitope and of Tn Antigen within the Glycoconjugate MAG According to the Invention Materials and Methods:

Mice

Six to eight week-old female inbred mice were used in all experiments. BALB/c mice were from Iffa Credo (L'Abresle, France).

Antigen Presentation Assay:

For the dose response assays, 10$^5$ T cell hybridomas 45G10 (specific for 103–115 poliovirus peptide) per well were cultured with 10$^5$ A20 cells (ATCC, TIB-208 Rockville, Md.) with different antigen doses for 24 h in RPMI 1640 medium supplemented with 10% Fetal calf serum, antibiotics 2 mM L-glutamine, 5×10$^{-5}$ M 2-mercaptoethanol. After 24 h, supernatants were frozen for at least 2 h at −70° C. 10$^4$ cells/well of the IL-2 dependent CTL cell line was cultured with 100 µl aliquot supernatant in 0.2 ml final volume. Two days later, [$^3$H] thymidine (0.3 µCi/well: AS=1 Ci/mmol) was added and the cells were harvested 18 h later with an automated cell harvester. Incorporated thymidine was detected by scintillation counting.

T-cell Proliferation Assay:

Mice were immunized subcutaneously with 10 µg of T, B-T, T4-MAP, B4-MAP or B4-T4-MAP compounds emulsified in complete Freund's adjuvant. Ten days later, lymph node (LN) cells were removed and single cell suspensions were prepared and cultured in HL-1 medium (Hycor) supplemented with 2 mM L-glutamine. 10$^6$ LN cells/well were plated onto 96 wells microtiter plates (TPP, Trasadingen, Switzerland) with 10 µg/ml of the indicated antigen or medium alone. After 3 days at 37° C., cells were pulsed for 18 h with $^3$H-TdR (NEN, Boston, Mass.) and then harvested onto fiber glass filters (Wallac Oy, Turku, Finland) with an automated cell harvester. Incorporated radioactivity was measured by scintillation counting. Results were expressed as mean of cpm from duplicate or triplicate culture wells. Standard deviations were less than 15% of the mean.

ELISA Tests:

Desialylated OSM was prepared as described in a previous publication (Tettamanti et al. (1968), Osinaga et al. (1996)) and was kindely given by Dr A. Babino.

α-GalNAc-Ser (referred to as 3 below in the synthesis section) was covalently linked to ovalbumin (Sigma, St. Louis, Mo.) using glutaraldehyde (Sigma) according to a known procedure (Leclerc et al. (1995)).

96-well microtiter plates (Nunc. Roskilde, Denmark) were coated with 10 μg per ml of the different antigens in 50 mM carbonate buffer pH 9.0 and incubated overnight at 4° C. for d-OSM, ovalbumin and Ova-Tn glycoconjugate, or at 37° C. for peptides and MAC constructs. After washing with PBS containing 0.1% tween 20, the 83D1 (IgM) or the MLS128 (IgG) anti-Tn mAbs were diluted in buffer (PBS plus 0.1% Tween 20, 1% BSA) and plated respectively at 2.5 μg/ml and 40 μg/ml for 1 hour at 37° C. Following three washes, wells were treated for 1 hour at 37° C. with goal anti-mouse IgM or anti-IgG peroxydase conjugate (Sigma, St. Louis, Mo.) and O-phenylenediamine/$H_2O_2$ was then added as substrate. Plates were read photometrically at 492 nm in an ELISA auto-reader (Dynatech, Marnes la Coquette, France).

Analysis of Antibody Response:

BALB/c mice (5 per group) were immunized intraperitoneally with 20 μg of T, B-T, T4-MAP, B4-MAP or B4-T4-MAP compound in aluminium hydroxyde (alum) on days 0, 20, 42 and 63. Mice were bled 10 days after each immunization and collected sera were individually tested for anti-Tn antibodies by ELISA as described above using d-OSM coated plates. Sera were serially diluted and tested for anti-Tn IgM and IgG content. The negative control consists of naive mouse sera diluted 100-fold. ELISA antibody titers were determined by linear regression analysis plotting dilution versus absorbance at 492 nm. The titers were calculated to be the Log10 highest dilution which gave twice the absorbance of normal sera diluted 1/100. Titers were given as the arithmetic mean±S.D. of the Log10 titers. Statistical analysis was performed by Student's t test. P values less than 0.05 were considered significant.

1) In Vitro Antigenicity of B4-T4-M

Figure 4A:
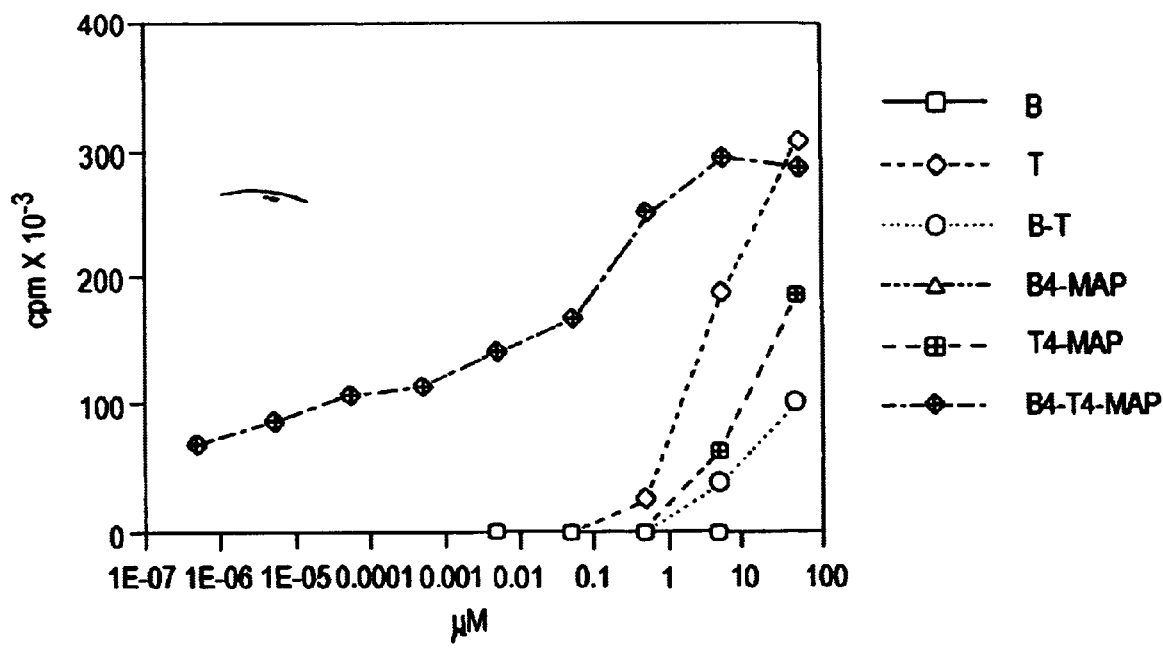
FIG. 4a depicts the T antigenicity of B4-T4-M or Tn MAG in vitro.

In vitro recognition of the B4-T4-M by a T hybridoma specific for the poliovirus 103–115 epitope T was assayed in the presence of lymphoma B, A20, as antigen presenting cell FIG. 4a illustrates the stimulation of a T hybridoma specific for the poliovirus peptide 103–115 T with different compounds containing this peptide:

$10^5$ lymphoma B, A20 (H-$2^d$) cells incubated at 37° C., in the presence of different concentrations of B, T, B-T, B4-MAP, T4-MAP and B4-T4-MAP were used for stimulating $10^5$ cells of T, 45G10 hybridoma (R. Lo-Man et al. (1994), 152: 5660–5669) specific for poliovirus 103–115 peptide and restricted by I-$A^d$ molecules. After 24 h, the culture supernatants were sampled then IL-2 was assayed by the measure of the proliferation of IL-2 dependent CTL line. After three days of culture, the proliferation of CTL cells was measured by tritiated thymidine incorporation. The results are expressed in cpm.

As can be seen on FIG. 4a, the B4-T4-MAP compound highly stimulates the IL-2 production by the I hybridoma specific for the I epitope. Compared to the other compounds T, B-T, TA4-MAP also containing epitope T, the antigenicity of the conjugate of the present invention compound B4-T4-MAP, is 100 to 1000 times higher. The B and B4-MAP compounds which are free of poliovirus epitope T do not stimulate the T hybridoma.

Then the in vivo T immunogenicity of the epitope T of the present invention conjugate, B4-T4-MAP, was assayed in BALB/c mice. After the immunization of mice with the B4-T4-MAP, or with a control compound (T, B-T, B4-MAP, T4-MAP), the proliferation of lymph node cells was measured in vitro after restimulation with compounds containing T epitope alone or in combination with B epitope (T and B-T compounds).

Figure 4B:
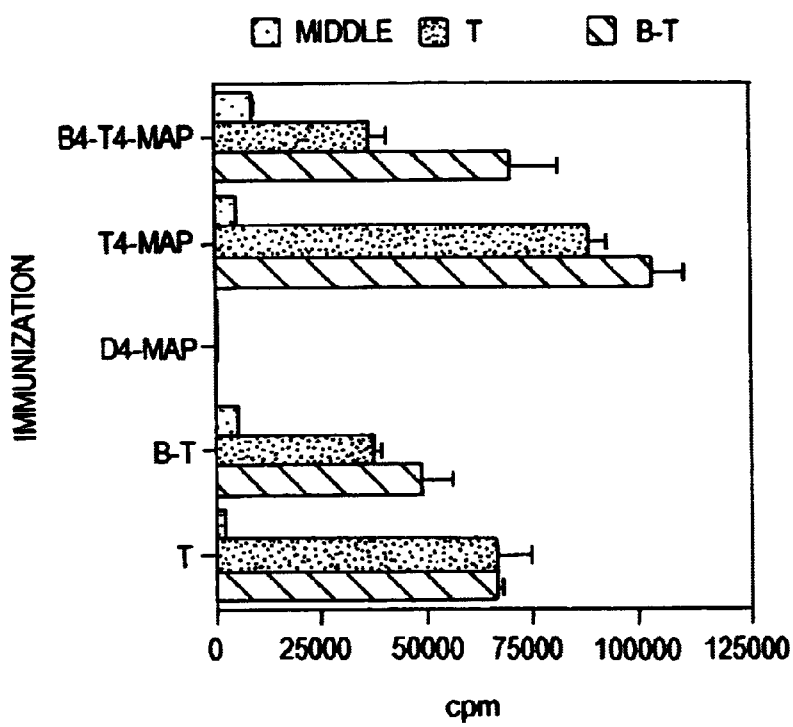
FIG. 4b illustrates the in vivo anti-T response of B4-T4-M.

The FIG. 4b illustrates the induction of a proliferative response specific for 103–115 peptide (T compound) after immunization of BALB/c mice with the B4-T4-MAP compound according to the present invention. BALB/c (H-$2^d$) mice were immunized subcutaneously with 10 μg of T, B-T, B4-MAP, T4-MAP and B4-T4-MAP in the presence of complete Freund adjuvant. Ten days later, draining lymph node cells were cultured in the presence of the medium alone or were restimulated in vitro with 10 μg/ml of a compound containing the 103–115 epitope (compound T- or B-T). Four days later, the proliferation of LN cells was measured by incorporation of tritiated thymidine. The results were expressed in cpm.

As can be seen on FIG. 4b, the MAPs, B4-T4-MAP and T4-MAP compounds, as well as the T and B-T compounds containing the T epitope, induce in vivo a proliferative T response specific for this T epitope. The specificity of the T response observed is demonstrated by the absence of proliferation of T cells originating from mice immunized with B4-MAP compound which is free of T epitope, after restimulating with T- or B-T compounds.

Thus it was possible to show through the analysis of the T immunogenicity of the conjugate according to the present invention (the B4-T4 MAP compound) that the poliovirus T epitope present in this compound is able to stimulate both in vitro and in vivo T-cells specific for this T epitope. Moreover a large increase in antigenicity of the T epitope is observed when the latter is combined to the carbohydrate epitope within the B4-T4-MAP structure.

Figure 3:
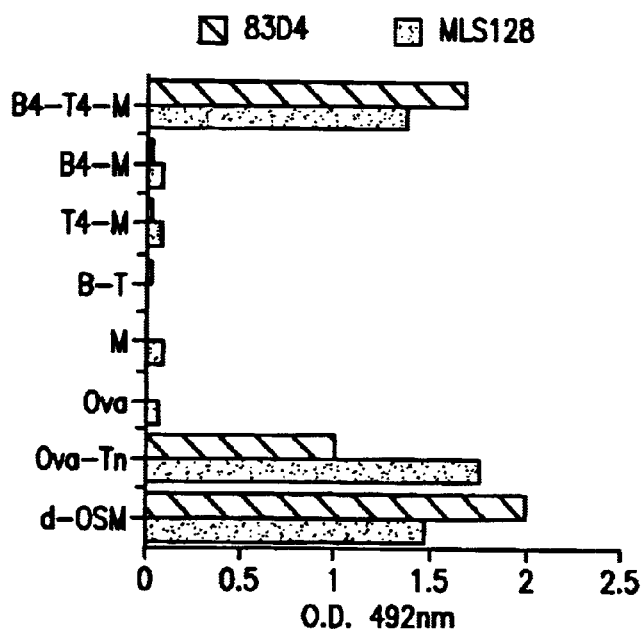
FIG. 3 shows the recognition of B4-T4-M by two anti Tn monoclonal antibodies.

2) Antigenicity of the MAG Structure 2.1 To assess the antigenicity of the Tn antigen in the glycoconjugate MAG system according to the invention, we have used two different well-characterized monoclonal antibodies (mAbs) which recognize the Tn antigen. FIG. 3 shows the binding ability of the anti-Tn 83 D4 (IgM) (Pancino et al. (1990)) and MLS 128 (IgG) (Numata et al. (1990)) monoclonal antibodies to the different MAG constructs using an ELISA assay. This binding is compared to the binding obtained with the Tn antigen 3 conjugated to a protein carrier (ovalbumin).

Fully synthetic multiple antigenic glycopeptides allow to a certain degree the rejection of an implanted tumour bearing aberrant glycosylations. However, to induce more efficient anti-tumour immunity against cancers, the development of such immunogens should not focus on a single carbohydrate antigen but must combine various carbohydrate targets for antibodies. The use of a given Tn cell epitope in conjunction with carbohydrates is a prerequisite for eliciting strong antibody responses, but it may limit its efficacy considering the MHC polymorphism observed in the human population. To avoid this drawback, MAG structures have to include several T cell epitopes with a particular focus an promiscuous MHC binding sequences, such as those described for tetanus toxin (Panina-Bordignon et al. (1989), Reece et al (1993)) for which human individuals are already primed (Etlinger et al. (1990)). Integration of CTL epitopes into MAG structures, such as MUC-1 derived peptides (Goydos et al. (1996)) for epithelial cancers, can also be easily achieved to widen the spectrum of the anti-tumour immune response. Here, we have privileged the use of a mild adjuvant, alum, which is authorised in healthy human populations, showing that strong adjuvants are not required to induce anti-carbohydrate specific immune responses by the MAG strategy. This latter point may be of major importance in extending the use of this strategy to bacterial oligosaccharides (Chong et al. (1997)) for vaccinating a healthy population.

It can be seen that the B4-T4-M system of the Invention as well as the desialylated OSM or the ovalbumin-Tn (Ova-Tn) conjugate were efficiently recognized by both of the mAbs, 83 D4 and MLS 128, whereas M, B4-M, T4-M, B-T (in the last case, only one mAb was tested) and ovalbumin itself were not. The d-OSM fragment recognized by MLS 128 monoclonal antibody was shown to contain three consecutive a-GalNAc-Ser/Thr residues (Nakach et al. (1991)) which might indicate that B4-T4-M but not B4-M is able to mimic the repeated glycosylated serine unit.

These results demonstrate that the D4-T4-M construct according to the invention can correctly present the Tn antigen.

2.2 Another study of the immunogenicity in mice of Tn-MAG conjugates of the invention was first carried on BALB/c mice which were immunized several times with said Tn-MAG conjugates or with the control compounds B-T, B4-MAP or T4-MAP, in the presence of aluminium hydroxyde (alum). Detection of IgM (FIG. 5aA) and IgG (FIG. 5aB) antibodies specific for Tn antigen was carried out by ELISA, measuring the recognition of the d-OSM.

Figure 5A:
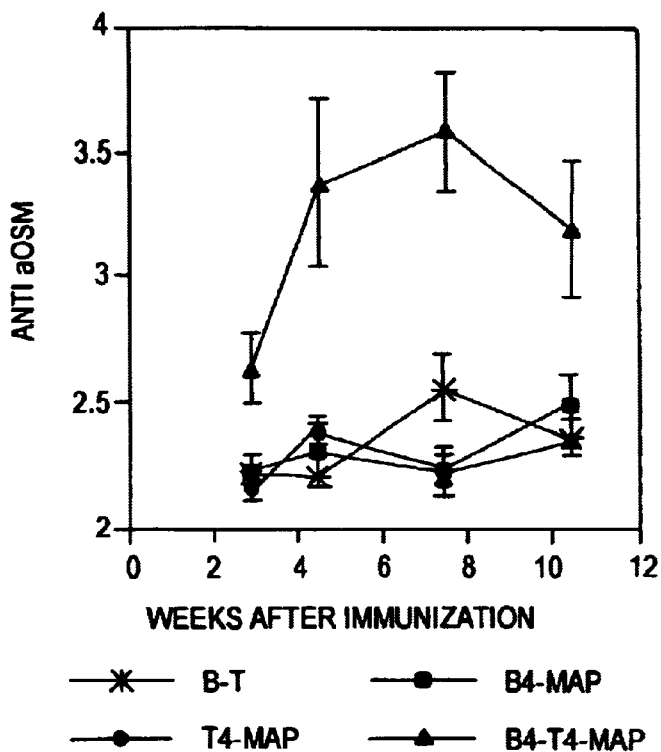
FIGS. 5a, 5b and 5c show the induction in BALB/c, SJL/J and DBA/1 mice, respectively, of anti-Tn antibody by the Tn-MAG compound.
Figure 5B:
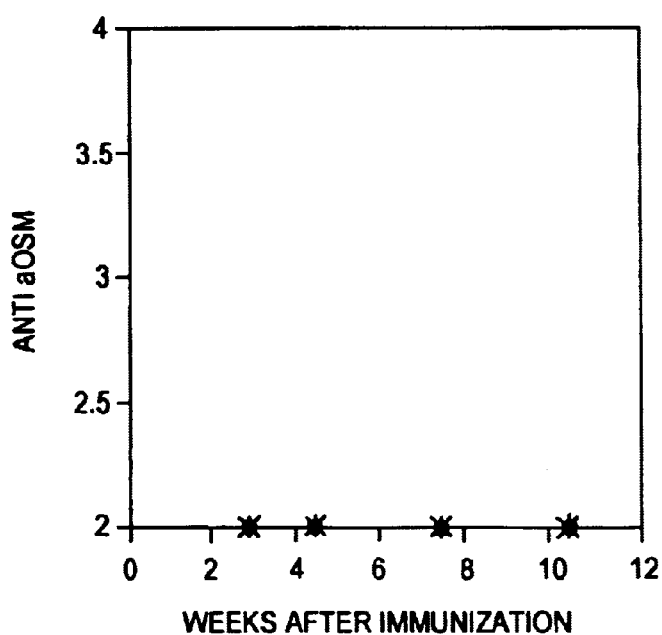

As can be seen on FIGS. 5a and 5b, after two immunizations with the B4-T4-MAP compound according to the invention, IgM antibodies specific for the Tn antigen were induced in BALB/c mice, unlike compounds B-T, B4-MAP or T4-MAP which were unable to induce anti-Tn antibodies. The amount of anti-Tn IgM induced with B4-T4-MAP remained unchanged after a third and a fourth immunization. With BALB/c mice it appeared that the antibody response to Tn induced by B4-T4-MAP was characterized by the presence of IgM antibodies and the absence of IgG antibodies.

2.3 A further study of induction of anti-Tn antibodies under the same conditions was conducted on another strain of mice of $H2^5$ haplotype (responding to tho T epitope) namely SLJ/J mice, and resulted in the induction of both class IgM and IgG antibodies to Tn (FIG. 5b). Thus, the B4-T4-MAP (Tn-MAG) compound of the present invention was capable of inducing antibodies to Tn belonging to different isotypes, the reason why there exist differences in the anti-Tn antibody class depending on the tested mouse strain is still under study.

The CD4$^+$ T-cell dependency of the Tn-MAG compound B immunogenicity was also studied. As stated above, BALB/c mice are responsive to the poliovirus T epitope and generate antibodies to Tn. In order to determine the T-dependency of the production of anti-Tn antibodies, we assayed for their capacity to produce antibodies to Tn another mouse strain responsive to poliovirus epitope T, namely the SLJ/J strain, and a non responsive to poliovirus epitope T strain, namely the DBA/1 strain.

Figure 5C:
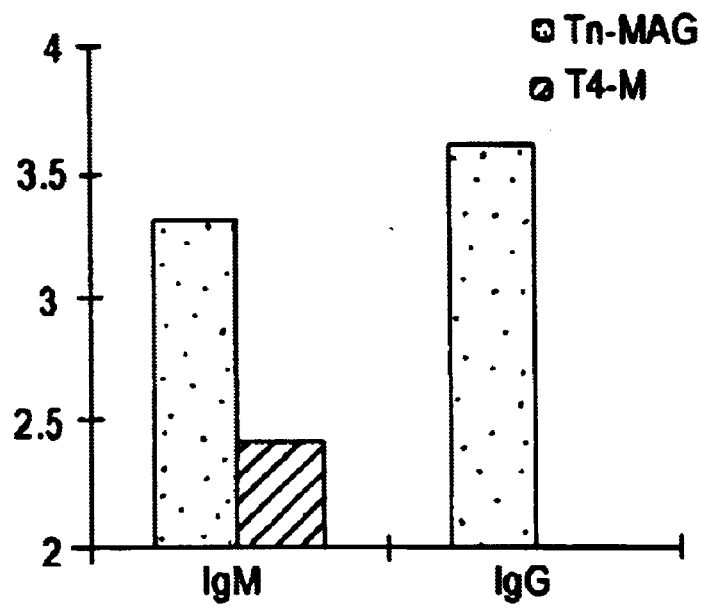
Figure 5D:
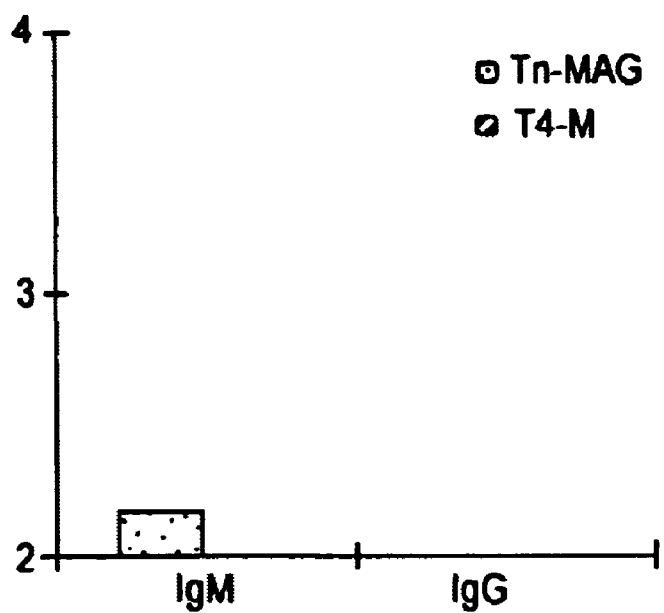

FIGS. 5b and 5c show that immunization with the Tn-MAG compound, according to the present invention, of SJL/J (5b) and DBA/1 (5c) mice resulted in the production of anti-Tn antibodies in the SLJ/J strain only, which is responsive to the poliovirus T epitope. These data demonstrate that the CD4$^+$, T epitope present in the Tn-MAG compound of the present invention is necessary to the production of antibodies to Tn.

2.4 We further studied the induction of anti-peptide antibodies using the Tn-MAG compound of the present invention.

Figure 6:
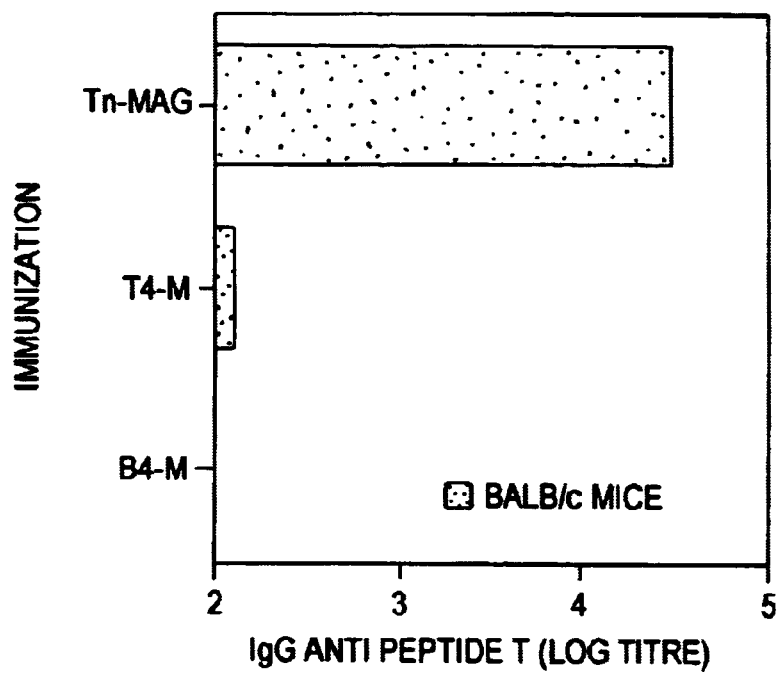
FIG. 6 illustrates the induction in BALB/c mice of antibody responses by the Tn-MAG compound containing Tn antigen and poliovirus epitope T, $CD4^+$.
Figure 7:
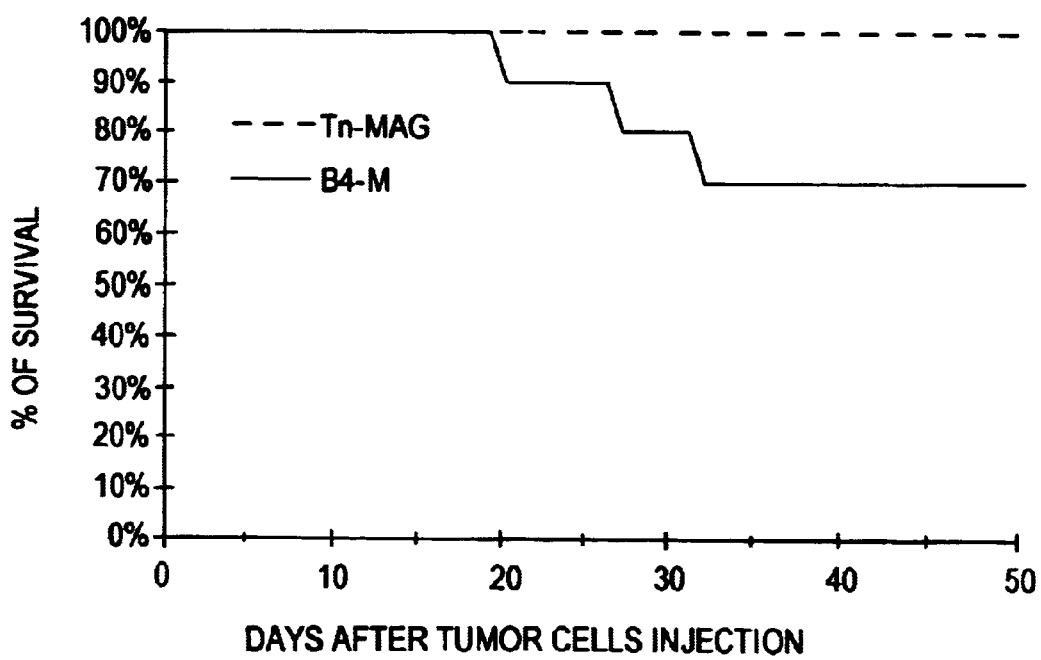
FIG. 7 illustrates the results of the protection induced with the Tn-MAG compound against murine adenocarcinoma TA3/Ha expressing Tn antigen in challenge injected BALB/c mice.

As stated above the conjugate of the present invention (Tn-MAG compound) contains four copies of the 103–115 sequence of VP1 protein of poliovirus type 1 (T peptide), linked to the carbohydrate Tn antigen. We have tested in mice the ability of the Tn-MAG compound to induce antibodies specific for the T peptide. As shown in FIG. 6, immunization of BALB/c mice with the Tn-MAG of the present invention induced a strong IgG response specific for the T peptide (103 115), whereas the T4-M compound lacking the carbohydrate Tn antigen, as well as the B4-M compound containing only the Tn antigen, were unable to elicit an anti-T peptide antibody response. Therefore, the presence of the carbohydrate moiety in the conjugate Tn-MAG of the present invention results in a strong potentiating effect on the induction of anti-peptide antibodies against the peptidic poliovirus contained in the MAG compound. These data suggest that such a carbohydrate peptide conjugate can be used to promote anti-peptide response generally in MAP synthetic compounds containing pathogen derived peptidic sequences.

Example 3

Protection Induced with the Conjugate of the Present Invention (Tn-MAG Compound) Against Murine Adenocarcinoma TA3/Ha Expressing Tn Antigen in Challenge Injected BALB/c Mice In order to test the efficiency of the anti-Tn B response induced in mice with the MAC compound, a challenge injection was carried out in vaccinated mice. 1000 cells per mouse of the murine adenocarcinoma cell, TA3/Ha (P. Y. S. Fung et al. (1990) Cancer Research, 50; 4308–4314), expressing Tn antigen, were intraperitoneally administered to BALB/c mice having received 4 injections of the B4-M or Tn-MAG compounds. The FIG. 7 is a graph illustrating the mortality versus the number of days after tumor challenge. BALB/c mice were immunized at days 0, 21, 42 and 100 with 20 $\mu$g of B4-M or Tn-MAG compound in the presence of alum. 15 days after, the mice received a challenge injection of 1000 TA3/Ha adenocarcinoma cells. The mortality was followed during a period of 50 days. As can be seen in FIG. 7, 70% only of the mice survived when these were immunized with B4-M compound which does not allow to induce an antibody to Tn. On the contrary, 100% of the mice having received four injections of the conjugate of the present invention survived at D50 after the tumor challenge. These data show that the antibodies induced with Tn compound of the present invention result in improving the mice survival after a tumor challenge causing a moderate lethality.

Example 4

Recognition of a Human Adenocarcinoma by Antibodies Originating from a Serum of a Mouse Immunized with the Conjugate of the Present Invention (Tn-MAG Compound)

In order to evaluate the possible human applications of the conjugate of the present invention, the sera of mice having received the latter were assayed for their ability to recognize a human tumor cell. For this purpose, we used the LS180 cell (ATCC CL-187) which a adenocarcinoma derived from a patient having developped a colon cancer. A flow cytometry analysis of the recognition of LS180 cell by a serum originating from a SLJ/J mouse having received three injections of the present conjugate (Tn-MAG) show that the induced anti-Tn antibodies are capable of recognizing Tn antigen at the surface of L3180 cells.

Example 5

Antigenicity of the Tn Antigen and the T-cell Epitope Included into the MAG Conjugates of the Invention Syntheses:

The Tn antigens α-GalNAc-Ser-Thr) were synthesized by classical methods (Lemieux et al. (1979), Ferrari et al. (1980)). Syntheses of the MAG:Tn-PV, MAP:PV, Tn-PV, and PV were performed by the solid phase methodology using the FMOC chem istry as described previously (Bay et al. (1997)). After attachment of the β-alanyl spacer to the Wang resin, the lysine core was assembled by coupling successively two levels of FMOC-Lys-(FMOC)OH, providing four amino groups. The lysine core was further elongated by the protected amino acid, of the T-epitope sequence of the poliovirus (KLFAVWKITYKDT), SEQ ID No: 4), to produce the MAP:PV. Ultimately, the α-GalNAc-Ser was incorporated to the four branches peptide, which gave the MAG:Tn-PV construct after deprotection and cleavage from the resin, as reported previously (Bay et al. (1997)). All of the final constructs were purified by reverse-phase high-performance to liquid chromatography and were characterized by amino acid analysis and electrospray mass spectrometry. The Tri$_3$-TT glycopeptide [Ser(αGaINAc)-Thr(α-GaINAc)-Thr(α-GaINAc)-QYIKANSKFIGITEL), (SEQ ID NO: 1), was prepared by incorporation, step by step, of the appropriate peracetyl-glycosylated FMOC-Ser Thr in the peptide sequence using 2-(1H-benzotriazole-1-yP)-1,1,3,3 tetramethyluronium tetrafluoroborate/N-hydroxybenzotriazole (TBTU/HOBT) as the coupling reagent. Deacetylation of the sugar residue of the glycopeptide was achieved with a catalytic amount of sodium methoxide in methanol at pH 11. The crude product was purified by high-performance liquid chromatography (Bay et al. (1997)) with a gradient from 10 to 35% and 14.74-min retention time. electrospray mass spectrometry: 2623 (calculated, 2623:56). Amino acid analysis: Ala, 1 (1); Asp, 1.04 (1); Glu, 2.16 (2); Gly, 1.08(1); Ile, 2.95 (3); Leu, 1.1 (1): Lys, 2.04 (2); Phe, 1.01(1); Ser 1.86(2); Thr, 2.76(3); and Tyr 0.97(1).

T-cell Stimulation.

The recognition of the poliovirus T-cell epitope contained in the different constructs was analyzed using a specific T-cell hybridoma and A20 cells as antigen presenting cells, as described previously (Lo-Man et al. (1996)). T-cell hybridomas ($10^5$) were cultured with $10^5$ A20 cells in the presence of the indicated construct in RPMI 1640 supplemented with 10% FCS, antibiotics, L-glutamine, and mercaptoethanol. Interleukin-2 synthesis following recognition by the T cell receptor of hybridoma T cells was assessed by the proliferation of the interleukin 2-dependent CTLL cell line using [$^3$H]thymidine.

Mice and Reagents.

Six to 8 week-old BALB/c SJL/J, and DBA/2 mice were from Iffa Credo. DBA/1 mice were from the animal colony of the Pasteur Institute. The anti-Tn mAb MLS128 (Numata et al. (1990)) was provided by Dr. H. Nakada (Kyoto Sangyo University, Japan). Tn was conjugated to chicken OVA (Tn-OVA) at an initial molar ratio of 4000:1 using glutaraldehyde, as described previously (Bay et al. (1997)).

ELISA and Flow Cytometry.

Mouse sera were tested for anti-Tn antibodies by ELISA using the synthetic glycopeptide Tn$_3$-TT or the parent peptide TT(YIKANSKIGITEL). Ninety-six-well microtiter plates (Nunc, Roskilde, Denmark) were coated with 0.1 μg of antigen per well in 50 mM carbonate buffer (pH 9.6) and incubated for 1 h at 37° C. After washing with PBS containing 0.1% Tween 20, the serially diluted sera in buffer (PBS plus 0.1% Tween 20–1% BSA) were added to the wells for 1 h at 37° C. Following three washes, wells were treated 1 h at 37° C. using goat antimouse IgG or IgM peroxidase conjugate (Sigma Chemical Co., St. Louis, Mo.) and O-phenylenediamine-H$_2$O$_2$ was then added as substrate. Plates were read photometrically at A$_{492\ nm}$ in an ELISA auto-reader (Dynatech, Marnes la Coquette, France). The negative control consisted of naive mouse sera diluted 100-fold. ELISA antibody titers were determined by linear regression analysis plotting dilution versus A$_{492\ nm}$. The titers were calculated to be the log$_{10}$ highest dilution, which gave twice the absorbance of normal mouse sera diluted 1:100. Titers were given as the arithmetic mean±SD of the log$_{10}$ titers.

Mouse sera were also tested at a 1:250 dilution by flow cymetry on Tn-expressing human tumor cell lines, Jurkat and LS180 and on the TA3/Ha murine cell line. Cells were first incubated for 30 min with sera at 4° C. in PBS containing 5% FCS and 0.1% sodium acid and then with an antimouse IgM/IgG goat antibody conjugated to FITC (Sigma). One % paraformaldehyde fixed cells were analyzed on a FACS can flow cytometer (Becton Dickinson, San Jose, Calif.).

Results:

The Tn Antigen and the T-cell epitope included into the MAG retain their antigenicity.

Figure 8:
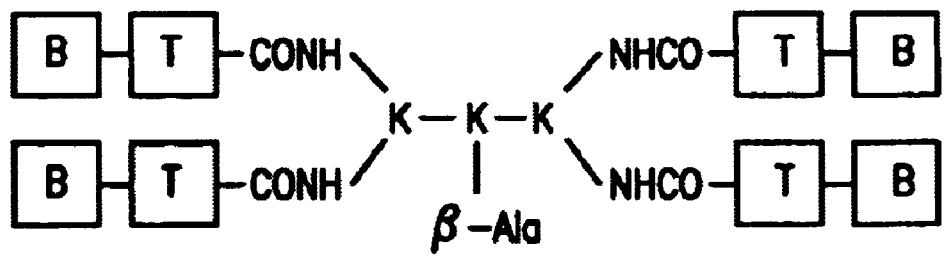
FIG. 8 schematic representation of the MAG:Tn-PV molecule.
Figure 8:
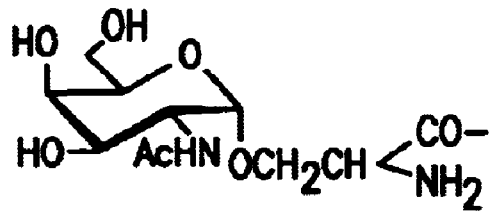

As shown in FIG. 8 the MAG synthesized is composed of a dendrimeric lysine core structure with four arms. Each arm is linked to a CD4$^+$ T cell epitope (PV peptide: KLFAVW-KITYKDT (SEQ ID NO: 4) sequence from the poliovirus type 1; (Lo-Man et al. (1996)) with a single α-N-acetylgalactosamine-serine residue (Tn) at the NH$_2$ terminus [MAG:Tn-PV: (Ser(α-GalNAc)]$_4$-K$_2$-K-βAla; Bay et al. (1997))].

The B-cell antigenicity of the Tn antigen included in the MAG:Tn-PV construct was analyzed using the MLS128 anti-Tn mAb, which was generated after immunization with the LS180 adenocarcinoma cell line derived from a colon cancer patient (Numata et al. (1990)).

Figure 9A:
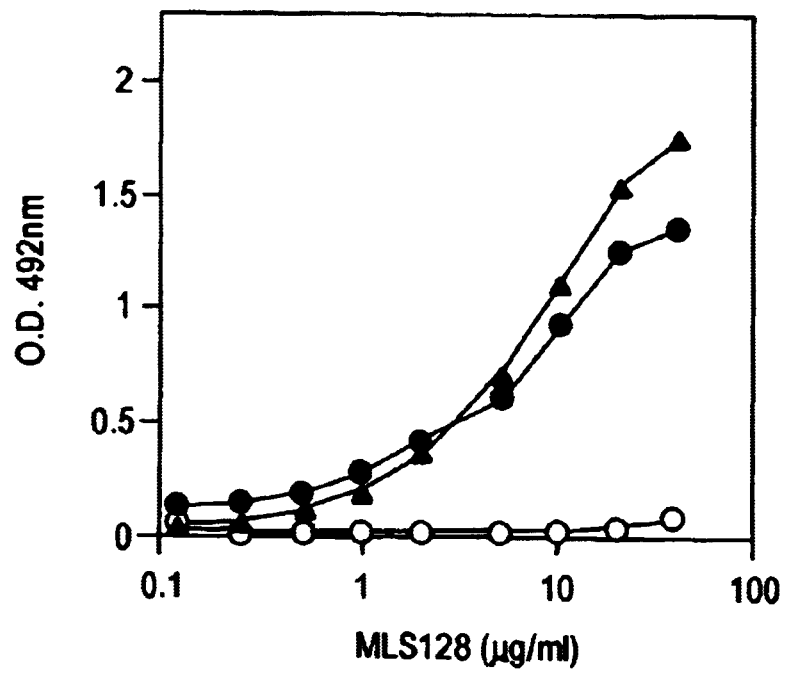
FIG. 9B and T-cell antigenicity of the MAG Tn-PV, a, the MLS28 mAb specific for Tn was tested by ELISA for reactivity to Tn-OVA conjugate (▲), control MAP:PV (○), and MAG:Tn-PV (●) coated at 1 μg/ml, b, stimulation of a PV-specific T-cell hybridoma by the PV (□), Tn-PV (■), MAP:PV (○), and MAG:Tn-PV (●) constructs in the presence of A20 cells.

FIG. 9a shows that the MLS128 mAb recognized the MAG:Tn-PV construct but not the parent construct devoid of the Tn antigen, MAP:PV [(PV)]$_4$-K$_2$-K-βAla] This recognition was in the same range as that observed not only with Tn conjugated to the chicken OVA protein (FIG. 9a) but also with the a-OSM (Bay et al. (1997)).

Figure 9B:
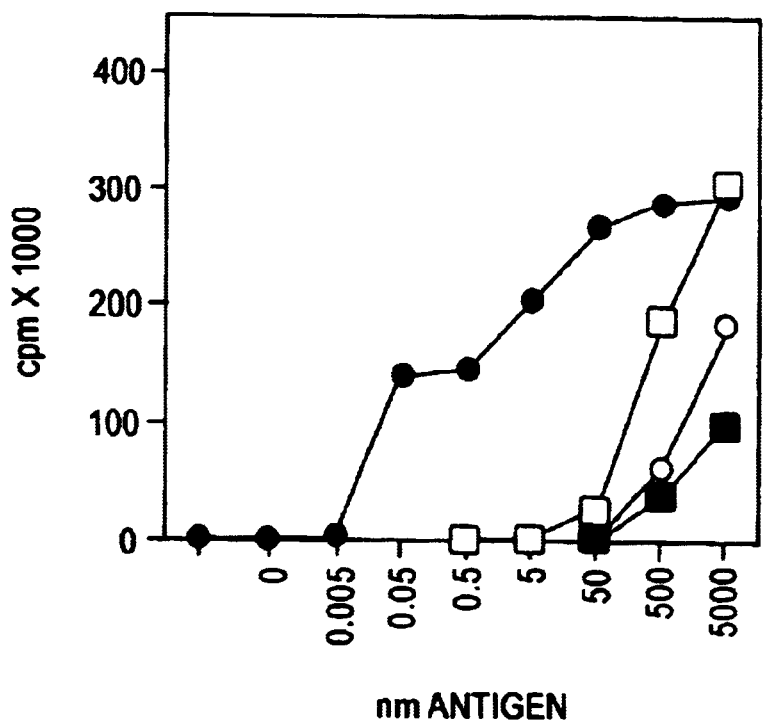

The poliovirus-derived PV peptide was included in the MAG:Tn PV to elicit a T cell-dependent antibody response. However, linkage of carbohydrates to peptides can interfere with peptide binding to MHC-encoded molecules with T-cell recognition (Deck et al. (1995)). For instance, Jensen et al. (1997)) showed that a T-cell hybridoma specific for a hemoglobin-derived peptide, glycosylated with α-GalNAc at a Thr residue, did not recognize the unglycosylated peptide in vitro. However, in this particular case, the glycosylation was introduced into the T-cell core sequence, whereas in our case, the Tn antigen was attached at the NH$_2$ terminus of the PV peptide (KLFAVWKITYKDT), (SEQ ID No: 4), clearly distant from the core sequence, which was characterized as FAVWKITYKD, (SEQ ID No: 15), (Lo-Man) et al. (1996)). As seen in FIG. 9b, a PV-specific T-cell hybridoma recognize the unglycosylated PV peptide as well as the glycosylated Tn-PV peptide showing that the Tn saccharidic epitope did not alter the T-cell recognition of the PV peptide sequence. To analyse the T-cell antigenicity of the MAG:Tn-PV, A20 antigen-presenting cells were incubated with the MAG:TN6PV or the control constructs in the presence of a PV-specific T-cell hybridoma (FIG. 9b). It is noteworthy, that the presence of the Tn antigen dramatically increased the presentation of the PV peptide by MHC molecules because I-cell stimulation was achieved with a 10,000-fold less MAG:Tn-PV dose compared to the MAP:PV construct and to the PV free peptide (FIG. 9b). This effect was only observed with the dendrimeric MAG structure because the stimulation induced by the Tn-PV glycopeptide [Ser(α-GalNAc)-PV] or the PV peptide was similar. The mechanisms underlying this enhancing effect remain unclear. However, because the formation of stable peptide/MHC complexes requires intracellular peptide loading on MHC molecules, the enhanced PV peptide presentation observed with the MAG:Tn-PV may stem from the intracellular processing of this construct. This result could also suggest that the MAG:Tn-PV endocytosis by antigen presenting cells is mediated by the cross-linking of a GalNAc-specific receptor. After immunization of mice with the MAG:Tn-PV, T-cell responses specific for the PV epitope were stimulated in vivo (data not shown). Altogether, these results demonstrate that the Tn antigen on the MAG:Tn-PV construct is available for antibody binding and strongly enhances MHC presentation of the T-cell epitope, illustrating the potency of the MAG:Tn-PV construct to induce T cell-dependent anti-Tn antibodies.

Example 6

Induction of High Titers of Anti-Tn Antibodies that Recognize Tn-positive Tumor Cell Lines Material and methods are described in example 5.
Results:

The MAG:Tn-PV induces high titers of anti-Tn antibodies that recognize Tn-positive tumor cell lines.

The PV peptide contains a promiscuous MHC binding sequence, which enables its presentation to T cells by I-E$^d$ and I-A$^B$ MHC molecules (Lo-Man et al. (1996)). Therefore, the immunogenicity of the MAG:Tn-PV was tested in different mouse strains expressing one of these MHC molecules, BALB/c (I-E$^d$), DBA/2 (I-E$^d$), and SJL/J (I-A$^B$) mice were immunized with the MAG: Tn-PV or with the control MAP:PV in alum, and sera were tested for anti-Tn antibodies (table 1). The MLS128 mAb was shown to recognize three consecutive Tn antigens ([α-GalNAc]-Thr [α-GalNAc]) on a -OSM and glycophorin (Nakada et al. (1991)). We, therefore, synthesized a glycopeptide, Tn$_3$-TT, irrelevant to the MAG-Tn-PV aminoacid sequence containing these three Tn antigens at the NH$_2$ terminus of a linear peptide (TT) to evaluate by ELISA the level of anti-Tn antibodies. Immunization with the MAG:Tn-PV hut not with the control MAP:PV induced anti-Tn IgG antibodies (mainly IgG1) in all three mouse strains tested. After three immunizations, Tn-specific IgM antibodies were still detected in BALB/c and SJL/J mice (table 1). The Tn specificity of the antibodies using the Tn$_3$ TT glycopeptide was assessed by the lack of recognition by all mouse sera of the parent TT peptide devoid of the Tn antigen. DBA/1 (I-A$^q$) mice, which do not respond to the PV peptide (14), did not develop any anti-Tn antibodies following MAG:Tn-PV immunization, showing the T-cell dependency of the anti-Tn antibody response.

Figure 10A:
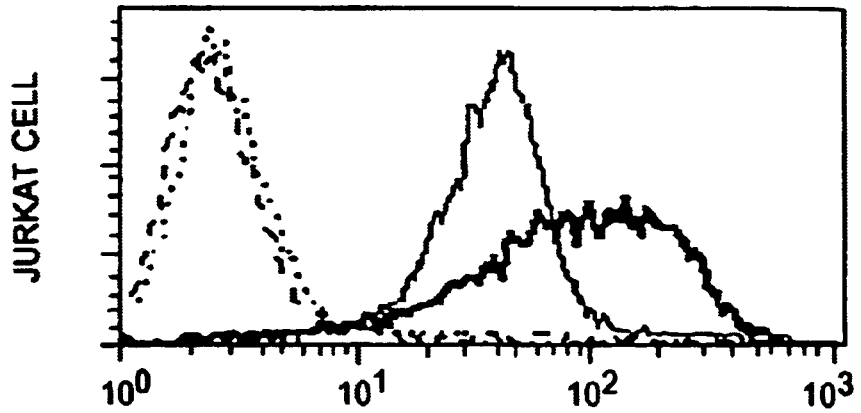
FIG. 10 recognition of tumor cell lines bearing the Tn antigen by sera from MAG:Tn-PV primed mice. Flow cytometry analysis was carried out on human Jurkat (a) and LS180 (b) cells and (c) murine TA3/Ha cells incubated with sera (diluted at 1:250) collected from BALB/c naive mice (point line), MAP-PV primed mice (short dashes), MAG:Tn-PV primed mice (bold line) or the MLS128 mAb (long dashes). Binding was detected using FITC labeled antibodies specific for mouse immunoglobulin. The positive staining observed with the serum from the MAG:Tn-pv primed mouse is representative of five individually tested sera.
Figure 10B:
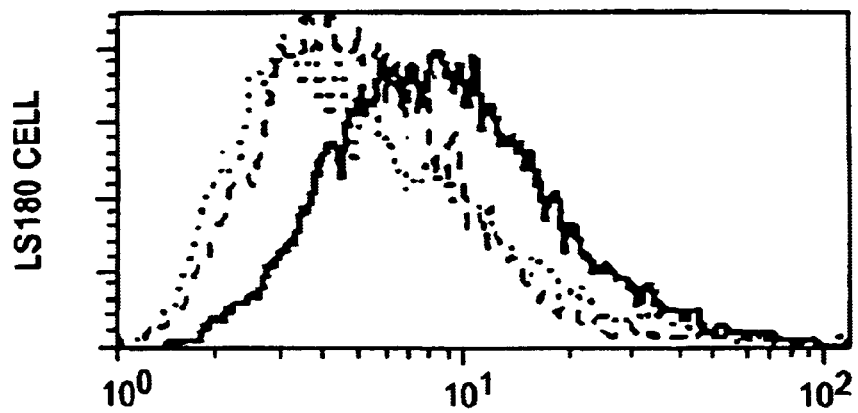
Figure 10C:
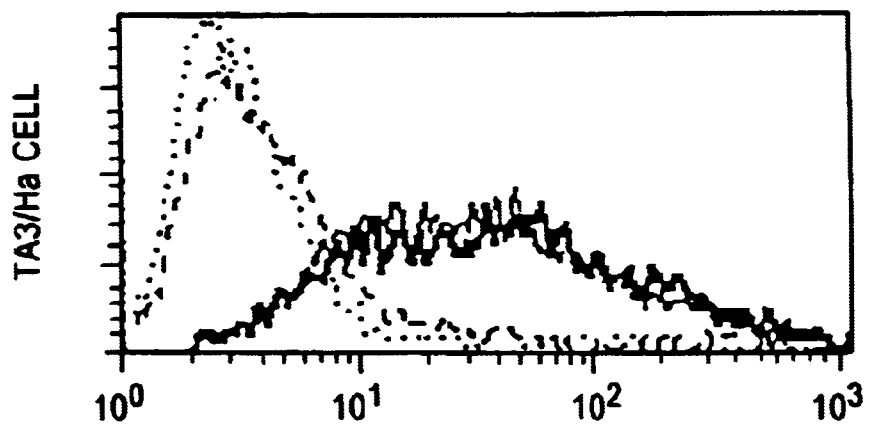

To ensure that mouse sere were able to recognize the native Tn antigen, we analyzed the binding of these sera to tumor cell lines expressing Tn. α-GalNAc-Ser/Thr is present on glycoproteins expressed by the human Jurkat T-lymphoma cell line (Nakada et al. (1991)) and LS180 adenocarcinoma cell line (Numata et al. (1990)). FIG. 10, a and b, shows that anti-Tn positive sera from BALB/c mice primed with the MAG:Tn-PV bound both human cell lines as efficiently as the MLS128 mAb, whereas sera from naive mice or MAP:PV immunized mice did not recognize these cell lines. These results demonstrate that anti-Tn antibodies induced by the MAG:Tn-PV recognize the native form of Tn on human tumor cells.

TABLE 1

The MAG:Tn-PV Induced anti-Tn specific antibodies[a]

| Mouse strain | Antigen | Tn$_3$ TT | | TT peptide | |
|---|---|---|---|---|---|
| | | IgM | IgG | IgM | IgG |
| BALB/c | MAP:PV | <250 | <250 | <250 | <250 |
| | MAG:Tn-PV | 6,660 ± 3,760 | 81.120 + 18.000 | <250 | <250 |
| DBA/2 | MAP:PV | <250 | <250 | <250 | <250 |
| | MAG:Tn-PV | <250 | 6,020 ± 2,400 | <250 | <250 |
| SJL/J | MAP:PV | <250 | <250 | <250 | <250 |
| | MAG:Tn-PV | 800 ± 570 | 108,060 ± 34,600 | <250 | <250 |
| DBA/1 | MAP:PV | <250 | <250 | <250 | <250 |
| | MAG:Tn-PV | <250 | <250 | <250 | <250 |

[a]Mice (five per group) received three injections (days 0, 21 and 42) of 20 μg of MAP:PV or MAG:Tn-PV mixed with 1 mg of alum, except for DBA/2 mice, which only received two injections (days 0 and 21). Sera were collected 10 days after the last boost, and antibody titers specific for Tn were determined by ELISA using the Tn$_3$-TT glycopeptide or the parent TT peptide devoid of the Tn motifs. Results are expressed as the mean ± SE of individual antibody titers.

Example 7

Anti-tumor Activity of MAG:Tn-PV

Antitumor Immunotherapy:

The murine mammary adenocarcinoma cell line, TA3/Ha was grown by passage on BALB/c mice. After i.p. administration of 1000 TA3/Ha cells, 6-week-old BALB/c mice were injected s.c. with 50 μg of MAG:Tn-PV or control MAP:PV construct with 1 mg of alum. Survival of treated and untreated mice was followed for 50 days. Statistical analysis of survival curves was performed with the Statview software (Abacus Concepts) using the log-rank rest.

Results:

Immunotherapeutic treatments with the MAG:Tn-PV increase mouse survival and resistance to tumor challenge.

A murine model has been developed to test active specific immunization against mucin-type carbohydrates using the TA3/Ha adenocarcinoma cell line (Fung et al. (1990)) In this model, treatment with bovine- or ovine-desialylated mucin prior and after the tumor challenge afforded partial protection (Singhal et al. (1991)). Likewise, active immunotherapy in TA3/Ha-bearing mice using the T antigen β-Gal(1–3)α-GalNAc conjugated to the KLH protein together with cyclophosphamide was also able to strongly enhance mice survival (Fung et al. (1990)) FACS analysis of the TA3/Ha cell line (which expresses the Tn antigen on mucin epiglycanin; (Vn den Eijnden et al. (1979)) indicated that this cell line was recognized by MAG: Tn-PV induced antibodies (FIG.

Figure 11:
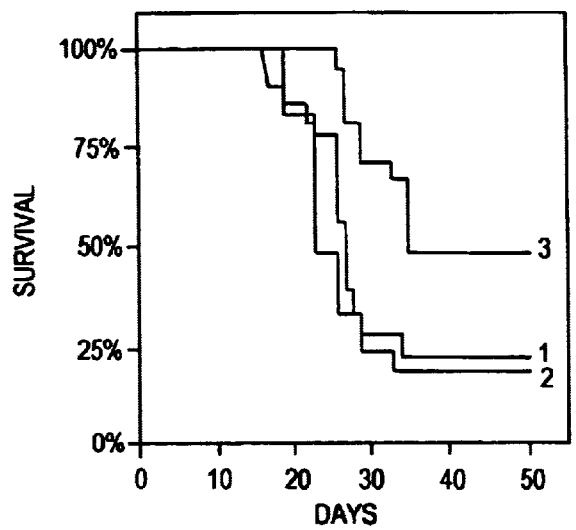
FIG. 11 Active specific immunotherapy in tumor bearing mice, After i.p. administration of 1000 TA3/Ha adenocarcinoma cells (day 0), 6 weeks old BALB/c mice were left untreated (group 1) or received on days 2, 5, 10 and 17; a 50 μg dose of the MAP:PV (group 2) or the MAG:Tn-PV (group 3) mixed with 1 mg of alum, and then mice were monitored for survival. Cumulative results of three independent experiments are presented corresponding to 18 mice in group 1 and 21 mice in groups 2 and 3. Differences are statistically significant between groups 1 and 3 ($P<0.02$) and between groups 2 and 3 ($P<0.01$).

10c). Therefore, we grafted 1000 TA3/Ha cells into BALB/c mice and followed their survival after active anti-Tn specific immunotherapy using the MAG:Tn-PV (FIG. 11). Following TA3/Ha graft, control groups of mice that were either left untreated (group 1) or treated with MAP:PV (group 2) displayed average survival times of 25 and 24 days, respectively, whereas after treatment with MAG:Tn-PV (group 3), the average survival time was delayed to 30 days for mice that did not reject the tumor. The TA3/Ha cell is originated from A mouse strain and was shown to grow on many allogeneic mouse strains, but its malignancy slightly varies from one mouse strain to another, depending on the genetic background (Hauschka et al. (1971)).

Untreated BALB/c mice displayed a 10–20% rejection rate of the TA3/Ha after inoculation of $10^3$ cells showing that the graft of TA3/Ha was a little less efficient in BALB/c than in other mouse strains used in studies performed with the same tumor model (Fung et al. (1990), Singhal et al. (1991)). However, statistically significant differences were observed in resistance or survival of mice following TA3/Ha implantation between group 3 (48%) and the control groups 1 (22%) and 2 (19%; P<0.02). These data show that the anti-Tn immune response induced by the MAG:Tn-PV increases the survival of tumor-bearing mice by rejecting the tumor graft exposing the Tn carbohydrate antigen.

Example 8

Synthesis of a Linear Glycopeptide Containing a CD4+ T Cell Epitope Associated with a Saccharidic Antigen to Induce Anti-saccharidic Antibodies The basic compound to induce anti-saccharidic antibodies is a linear peptidic sequence containing a CD4+T cell epitope linked to a saccharidic chain. The BT compound is composed by the KLFAVWKITYKDT), SEQ ID No: 4), sequence derived from poliovirus type 1 (CD4+T cell epitope) linked at the N-terminus to three GalNac-Ser/Thr residues (tumor associated saccharidic Tn antigen). The BT compound or the control PV peptide, KLFAVWKITYKDT sequence (SEQ ID No: 4), was injected to BALB/c mice mixed with complete Freund's adjuvantor with Alum as follows.

BALB/c mice (5 per group) were immunized in CFA or Alum with either the B-T-PV or the control peptide PV on days 0, 21, 42, 63. Sera were collected 10 days after the last injection and tested in ELISA for antibody titer against the B-T-PV glycopeptide or the PV peptide. Results are expressed in FIG. 12 as the mean titer obtained for five mice in each group.

Figure 12A:
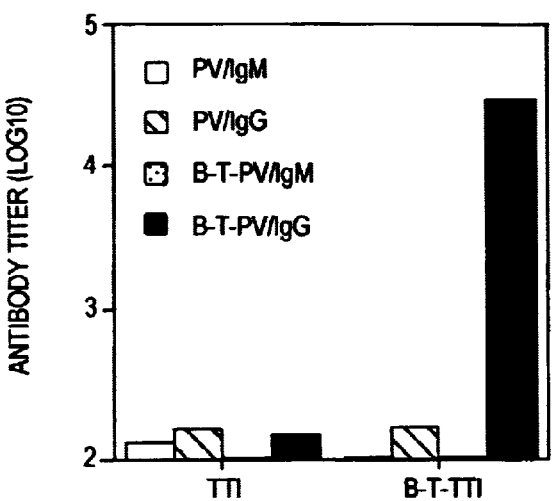
FIGS. 12A and 12B illustrate the results of immunization of Balb/C; mice with the PV peptide or B-T-$PV_1$ glycopeptide, respectively primed with CFA (FIG. 12A) and with alum (FIG. 12B).
Figure 12B:
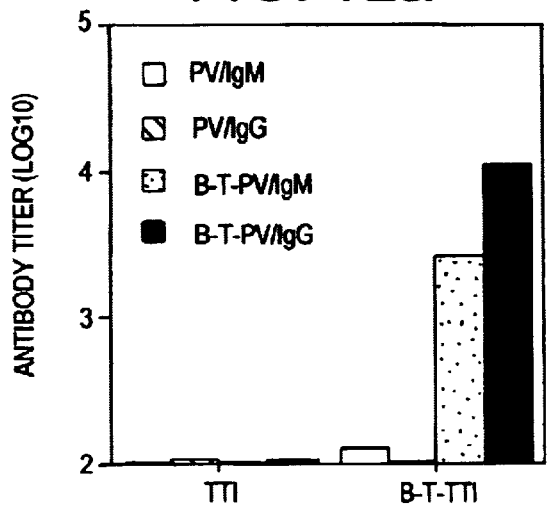

To detect by ELISA anti-saccharidic antibodies (anti-Tn), an irrelevant peptide sequence QYIKANSKFFIGITEL, (SEQ ID No: 1), linked at the N-terminus to three GalNac-Ser/Thr residues (BT-TT1) was used, or the non-glycosylated YIKANSKFIGITEL (IT 1 peptide) as a negative control. As shown in FIG. 12, the B-T-PV glycopeptide induce anti-Tn antibodies, but not the PV peptide showing the specificity of the antibody repsonse.

These results demonstrate that a synthetic linear glycopeptide containing a saccharidic B cell epitope and a CD4+ T cell epitope is able to induce anti-saccharidic antibodies.

TABLE 2

Synthetic compounds and glycoproteins

| Antigen designation | Copy number per molecule | |
|---|---|---|
| | αGalNac-Ser (Tn antigen) | peptide 103–115 (T epitope) |
| T | 0 | 1 |
| B | 1 | 0 |
| B-T | 1 | 1 |
| M or MAP | 0 | 0 |
| B4-M | 4 | 0 |
| T4-M | 0 | 4 |
| B4-T4-M or Tn-MAG | 4 | 4 |
| Ovalbumin | 0 | 0 |
| Ovalbumin-Tn | ++* | 0 |
| d-OSM | ++* | 0 |

*several copies but copy number not determined.

Example 9

Synthesis of Linear Glycopeptides of the Invention

Material and Methods

The synthesis of the Tn antigens, appropriately protected, FmocSer(α-GalNAc)-OH and FmocThr(α GalNAc) OH was performed by classical methods (Paulsen et al. (1982). Paulsen et al. (1989)) starting from tri-O-acetyl-D-galactal (Shafizadeh et al. (1963)), N-(Fluorenylmethoxycarbonyl)-L-serine/threonine tert-butyl ester (Schultz et al. (1993), Vowinkel et al. (1967)) were used for the Koenigs-Knorr reaction with 3,4,6-tri-O-acetyl-2-azido-2-deoxy-α-D-galactopyranosyl chloride (Lemieux et al. (1979), Ferrari et al. (1980)). The catalyst use for the glycosylation was AgOTf for the L-aminoacid (Ser, Thr) and $Ag_2CO_3/AgClO_4$ for the D-serine. The final deprotection of the acetyls (Paulsen et al. (1985)) and of the t-butyl ester afforded Tn antigens appropriately protected for the peptide synthesis.

All the glycopeptides were assembled by the conventional solid-phase peptide methodology (Wang resin, Novabiochem) using the Fmoc chemistry. The appropriately protected aminoacids were incorporated manually in the peptide sequence by using TBTU/HOBT/DIEA as the coupling reagent (Fields et al. (1991)). Fmoc protection was removed with 20% piperidine in DMF. The glycosylated aminoacids FmocSer/Thr(α GalNAc) OH were incorporated as their pfp esters (Elofsson et al. (1993)) The peptides were cleaved from the resin with aqueous trifluoroacetic acid TFA (95%).

All the derivatives were purified by HPLC using a Perkin-Elmer pump system with a UV detector at 230 nm; the column was a Nucleosil $C_{18}$ (5 μm, 300 A", 250×10 mm) and the gradient was performed with water (0.1%/TFA)/acetonitrile in 20 min. The peptides and glycopeptides (table 3) were all characterized by amino acid analysis and mass spectrometry.

PV: HPLC gradient from 0% to 65%, retention time 12.6 min; FABMS: $[M+H]^+$ 1613 (Calcd. 1611.9). Amino acid analysis: Ala 1.16 (1), Asp 1.03 (1), Ile 0.96 (1), Leu 1.01 (1), Lys 2.92 (3), Phe 1 (1), Thr 1.84 (2), Tyr 0.99 (1), Val 0.94 (1).

Tn-PV; HPLC gradient from 10% to 60%, retention time 11.2 min; ESMS: 1903 (Calcd. 1903.22). Amino acid analysis: Ala 1 (1), Asp 1.05 (1), Ile 1.0 (1), Leu 1.05 (1), Lys 3.12 (3), Phe 1.05 (1), Ser 0.94 (1), Thr 1.97 (2), Tyr 1.06 (1), Val 1.0 (1).

$Tn_3PV$: HPLC: gradient from 10% to 60%, retention time 10.3 min. ESMS: 2512 (Calcd 2511.8); Amino acid analysis Ala 1 (1), Asp 1.05 (1), Ile 1.0 (1), Leu 1.05 (1), Lys 3.12 (3), Phe 1.05 (1), Ser 0.95 (1), Thr 3.74 (4), Tyr 1.00 (1), Val 1.0 (1).

D-(Tn$_3$)-PV: HPLC: gradient from 15% to 30%, retention time 16.9 min. ESMS: 2484 (Calcd 2483.74): Amino acid analysis Ala 1 (1), Asp 1.01 (1), Ile 0.96 (1), Leu 1.01 (1), Lys 3.06 (3), Phe 0.97 (1), Ser 2.7 (3), Thr 1.85 (2), Tyr 1.03 (1), Val 0.99 (1).

Tn$_3$-TT: HPLC: gradient from 10% to 35%, retention time 14.74 min: ESMS: 2623 (Calcd 2623.56). Amino acid analysis: Ala 1 (1), Asn 1.04 (1), Glu 2.16 (2), Gly 1.08 (1), Ile 2.95 (3), Leu 1.1 (1), Lys 2.04 (2), Phe 1.01 (1), Ser 1.86 (2), Thr 2.76 (3), Tyr 0.97 (1).

Tn$_6$-PV: HPLC: gradient from 10% to 60%, retention time 12.7 min; ESMS: 3525.0 (Calcd 3524.7). Amino acid analysis: Ala 1 (1), Asp 0.98 (1), Ile 0.97 (1), Leu 1.0 (1), Lys 2.91 (3), Phe 1.02 (1), Ser 2.09 (2), Thr 5.92 (6), Tyr 1.13 (1), Val 1.0 (1)

STTG$_6$KG. HPLC gradient from 0% to 17%, retention time 8.2 min. ESMS 834.3 (Calcd 834.4). Amino acid analysis: Ser 0.93 (1), Thr 2 (2), Gly 7.95 (7), Lys 1.21 (1)

STTG$_6$K(Biot)G: HPLC gradient from 0% to 20%, retention time 14.6 min. ESMS 1060.8 (Calcd 1061.1). Amino acid analysis: Ser 0.93 (1), Thr 1.89 (2), Gly 7 (7), Lys 1.09 (1)

Tn$_3$G$_6$K(Biot)G: HPLC gradient from 5% to 20%, retention time 11.4 min. ESMS 1669.7 (Calcd 1670.0). Amino acid analysis: Ser 1.09 (1), Thr 2 (2), Gly 6.48 (7), Lys 0.99 (1)

Tn$_3$G$_6$KG. HPLC gradient from 0% to 17%; retention time 7.6 min. ESMS. 1443.9 (Calcd 1443.6). Amino acid analysis: Ser 0.93 (1), Thr 1.70 (2), Gly 7 (7), Lys 1.0 (1)

KG$_4$Tn$_3$G$_3$: HPLC: gradient from 0% to 14%, retention time 9.6 min. ESMS: 1444.4 (Calcd 1443.6). Amino acid analysis: Ser 0.88 (1), Thr 2 (2), Gly 7.07 (7), Lys 1.03 (1)

Results of the Synthesis

The glycopeptides were assembled by the conventional solid-phase peptide methodology using the Fmoc chemistry which is compatible with the glycopeptide synthesis. The appropriately protected aminoacids were incorporated in the peptide sequence by using TBTU/HOBT/DIEA as the coupling reagent (Fields et al. (1991)). Of interest was the incorporation of three successive Tn residues which could be achieved with the fully deprotected sugar. Several groups described the coupling of a single N-terminal glycosyl aminoacid with unprotected carbohydrate hydroxyl groups (Bay et al. (1997), Anisfeld at al (1990), Filira et al. (1990)) (Reimer et al (1993)). However to our knowledge, only few examples of synthesis with subsequent coupling steps have been described and they only concern N-linked glycosyl-asparagin (Urge et l. (1992), Otvos et al. (1990)). In our case the O-glycosylated Fmoc-aminoacids FmocSer/Thr($\alpha$-GalNAc)-OH could be incorporated efficiently as their pfp esters (Elofsson et al. (1993)). This is very advantageous since it avoids the eventual side reactions (racemization and/or $\beta$-elimination) associated with the final deacetylation of the sugar residue. Furthermore the deprotection of the acetyl groups of three sugar units is difficult to follow by HPLC when the structure is multimeric as in the case of the MAG constructs.

For the synthesis of the Tn$_6$-PV glycopeptide, a glycine residue was introduced as a spacer on the two amino groups of the N-terminal lysine residue to reduce steric hindrance (see Table 3 for the identification of the glycopeptides).

TABLEAU 3

| | STRUCTURE OF THE DIFFERENT GLYCOPEPTIDES |
|---|---|
| STTTG$_6$KG | STTGGGGGGKG (SEQ ID NO:17) |
| Tn$_3$G$_6$KG | S*T*T*GGGGGGKG (SEQ ID NO:18) |
| Tn$_3$G$_6$K(Biot)G | S*T*T*GGGGGGK(Biotine)G (SEQ ID NO:19) |
| KG$_4$Tn$_3$G$_3$ | KGGGGS*T*T*GGG (SEQ ID NO:20) |
| PV | KLFAVWKITYKDT (SEQ ID NO:4) |
| Tn-PV | S*KLFAVWKITYKDT (SEQ ID NO:21) |
| Tn$_3$-PV | S*T*T*KLFAVWKITYKDT (SEQ ID NO:22) |
| D-(Tn$_3$)-PV | D-(S*)D-(S*)D-(S*)KLFAVWKITYKDT (SEQ ID NO:23) |
| Tn$_6$-PV | (S*T*T*G)$_2$KLFAVWKITYKDT (SEQ ID NO:24) |
| Tn$_3$-TT | S*T*T*QYIKANSKIGITEL (SEQ ID NO:25) |

*$\alpha$-GalNAc: PV: poliovirus p 103–116; TT: tetanus toxin p 830–844; L-amino acids in single letters code are designated by upper case letters. D-aminoacids are specified by the letter D.

Example 10

Antigenicity and Immunogenicity of the Linear Glycopeptides

Material and Methods

Mice and Immunization 6-to 8-week-old female BALB/c mice were from Janvier (Le Genest Saint-Isle, France). Mice were injected intraperitoneally with peptides or glycopeptides in CFA (Sigma), then boost injection were performed in IFA (Sigma). Sera were collected and tested to detect the presence of anti-Tn antibodies by ELISA or FACS.

ELISA (for Antigenicity)

The PV- and TT-glycopeptides were coated in 50 mM carbonate buffer pH 9.6 by overnight incubation at 37° C. on microtiter plates; then, several dilutions of MLS128 (a mouse IgG3 specific for the Tn antigen (Numata et al. (1990)) were added for 1 hr at 37° C. After washing, the MLS128 mAb bound to the coated compound was revealed using goat anti mouse IgG peroxidase conjugate (Sigma) and O-phenyldiamine/$H_2O_2$ substrates. The reaction was stopped by $H_2SO_4$ and the optical density (O.D.) read at 492 nm with an ELISA autoreader (Dynatech, Marnes la Coquette, France).

For the inhibition studies, streptavidin coated microtiter plates (Sigma, St. Louis, Mo.) were used and incubation with the biotinylated glycopeptide $Tn_3G_6K(Biot)G$ was performed for 1 h at 37° C. MLS128 mAb, at 1 μg/ml. was then added on the streptavidin coated plates with serial dilutions of the synthetic competitors (peptide or glycopeptide) for 30 minutes.

Results are expressed as the percentage of inhibition calculated from the values obtained without any competitor (O. D. max) or in the presence of a competitor peptide (O. D. comp.). % inhibition=100×[1−(O. D comp./O. D. max)].

ELISA (Antibody Titer)

Mouse sera were tested for anti-Tn antibodies by enzyme-linked immunosorbent assay (ELISA) using the synthetic glycopeptide $Tn_3G_6K(Biot)C$ or the unglycosylated analogue $STTG_6K(Biot)G$ as control. The biotinylated peptides at 1 μg/ml were incubated for 1 h at 27° C. on streptavidin coated microtiter plates. Then, serial dilutions of sera were added to the plates; bound antibodies were revealed using goat anti-mouse IgG or IgM peroxidase conjugate (Sigma). The titers were calculated to be the Log 10 highest dilution that gave twice the signal obtained with naive mice sera tested at 1/100 dilution.

Flow Cytometry (FACS)

Mouse sera were tested at serial dilutions by flow cytometry on the human Jurkat tumor cell line expressing In. Cells were first incubated for 30 min. with sera at 4° C. in PBS containing 6% FCS and 0.05% sodium azide and further incubated 30 min. with anti-mouse IgM goat antibodies conjugated to HIC (Pharmigen, San Diego, Calif.) and with a mixture of biotinylated anti-mouse IgG1, IgG2a, IgG2b and IgG3 antibodies from goat (Amersham, Les Ulis, France). IgG binding was next revealed using streptavidin-PE (Sera-lab). PFA fixed cells were analyzed on a FACScan flow cytometer (Becton Dickinson, Mountain View, Calif.) and analysis performed with CellQuest software (Becton Dickinson). The titers on Jurkat cells were calculated to be the log10 highest dilution that gave twice the geometric mean of fluorescence obtained with unstained cells.

1) Antigenicity

Figure 13A:
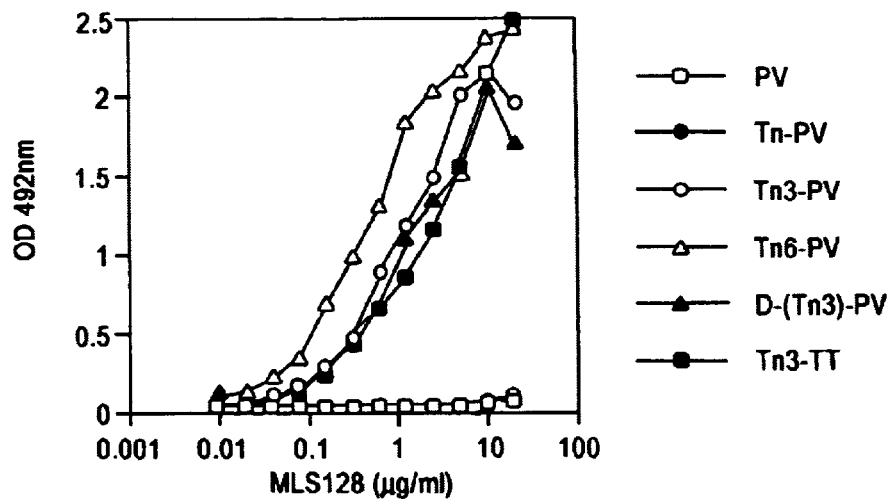
FIG. 13. Antigenicity of Tn-glycopeptides using the MLS128 mAb. MLS128 binding to various Tn-glycopeptides was assessed by direct ELISA (A). Inhibition of MLS128 binding to Tn3G6K(Biot)G (B and C) was performed by competitive ELISA using the indicated Tn-glycopeptides as described in material and methods section.

The antigenicity of the mono-, tri- and hexa-Tn glycopeptides containing the poliovirus sequence 103–115 (Tn-PV, $Tn_3$-PV, $Tn_6$-PV respectively) and the tri-Tn glycopeptide with the tetanus toxin sequence 830–844 ($In_3$-TT) was first evaluated by measuring the recognition of the Tn motif by the MLS 128 mAb (FIG. 13A). The tri- and hexa-Tn peptides are efficiently recognized by MLS 128, whereas the mono-Tn-PV and the PV peptides are not. On the other hand, the tri-Tn glycopeptide with three D-serine residues is also recognized by the antibody. Since the chirality of the D-($Tn_3$) motif in the PV-glycopeptide does not affect the recognition of the "Tn motif" by MLS 128, the aglycone (Ser/Thr) might not be of crucial importance.

Figure 13B:
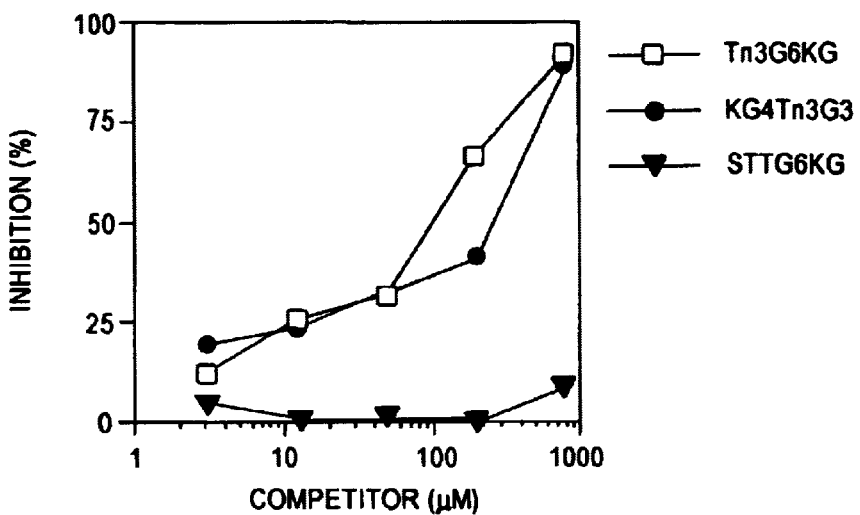

The influence, on the MLS 128 binding, of the position of the tri-Tn motif within the peptide backbone was first investigated. For this purpose, an inhibition assay was performed using $Tn_3G_6KG$ or $KG_4Tn_3G_3$ glycopeptides as competitors for the binding of MLS128 to $Tn_3G_6K(Biot)G$ coated on a streptavidin layer. The model polyglycine glycopeptide $Tn_3G_6KG$ was chosen for the competition assays because it competes efficiently with a-OSM for MLS 128 binding whereas the unglycosylated parent peptide, $STTG_6KG$, does not (data not shown). As can be seen in FIG. 13B, the inhibition is similar whether the tri-Tn cluster is at the N-terminal end of the peptide or in the middle of the peptide chain.

Figure 13C:
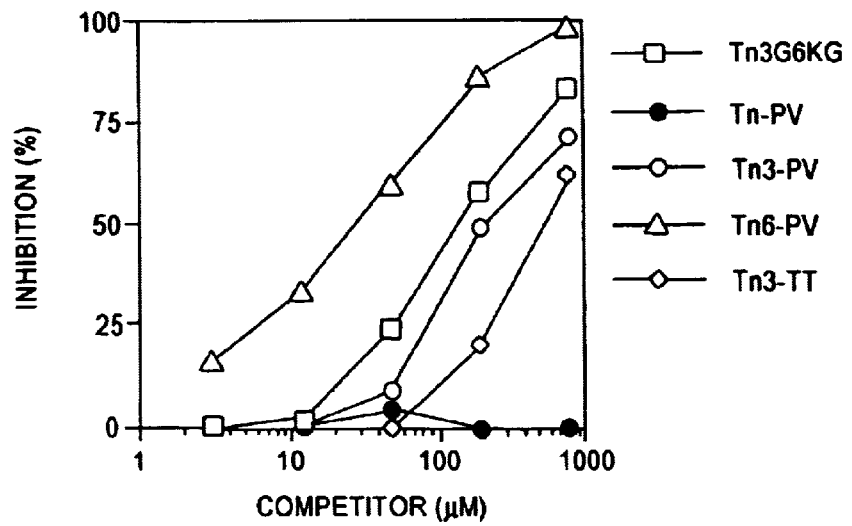

Furthermore, the recognition of the tri-Tn sequence by MLS 128 is only slightly affected by the nature of the adjacent peptide as shown in FIG. 13C, in inhibition studies with $Tn_3$-PV, $Tn_3$-TT or $Tn_3G_6KG$. These results indicate that the binding of the tri-Tn ligand to MLS 128 does not really depend on the peptide backbone. This feature is particularly important given the fact that the association of the Tn motif with a T cell peptide is required for its immunogenicity.

Strong immunoreactivity was observed with synthetic Muc2 peptides (14 Thr) containing nine or ten GalNAc residues; however the site of glycosylation in the peptide was not clearly determined (Inoue et al. (1998)). On the other hand, the MLS128 mAb was shown to recognize a tri-Tn motif on glycophorin (Nakada et al. (1993)) suggesting that the density of the Tn motif can be a critical point for antibody recognition. This point is illustrated in FIG. 13C by the incapacity of a mono-Tn glycopeptide (Tn-PV) to inhibit MLS128 binding.

In order to improve the antigenicity of the Tn-based glycopeptides, the density of the Tn motif was further increased by introducing one tri-Tn motif on each amino group of the N terminal lysine residue of the PV peptide ($Tn_6$-PV). As shown in FIG. 13C, this strategy leads to a significant enhancement of the antigenicity (measured in the competition assay) as compared to the $Tn_3$-PV peptide.

2) Immunogenicity

To analyse the ability of Tn based linear glycopeptides to induce anti-Tn antibodies, BALB/c mice received three injections of the Tn-PV. $Tn_3$-PV, D-($Tn_3$)-PV and $Tn_6$-PV glycopeptides or of the control PV peptide corresponding to the T cell epitope alone. Sera were collected after each immunization and tested for IgG and IgM anti Tn antibodies by ELISA using a glycopeptide with a tri-Tn motif associated to a polyglycine backbone, $Tn_3G_6K(Biotine)G$, which is unrelated to the PV sequence (FIG. 14). Another glycopeptide with an irrelevant sequence to PV was tested ($Tn_3$-TT) with similar results (data not shown).

Figure 14A:
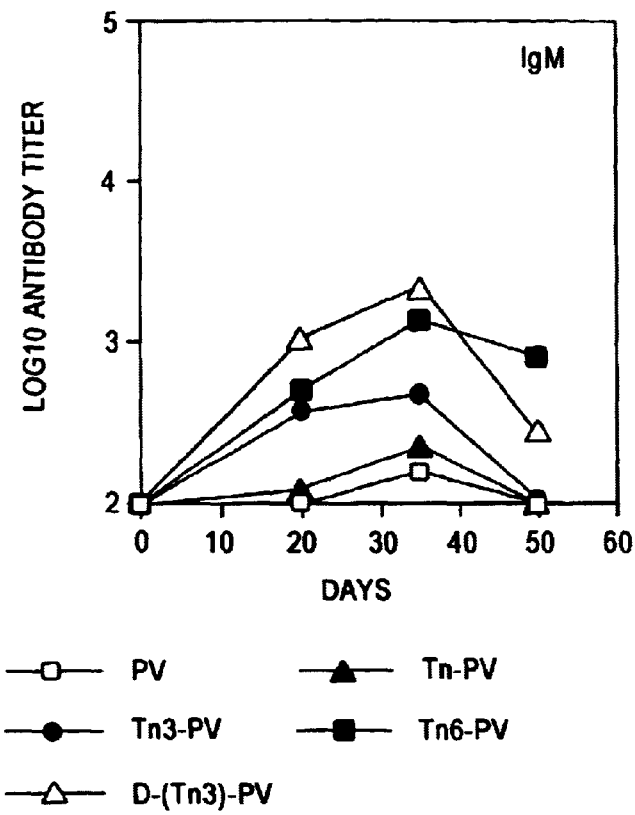
FIG. 14. Anti-Tn antibodies induced in mice immunized with Tn-glycopeptides as measured by ELISA. Mice (four per group) received three injections (days 0, 21 and 42) of 50 μg of PV, Tn-PV, Tn3-PV, Tn6-PV and D-(Tn3)-PV in CFA for the first injection and in IFA for boost injections. After each injection, sera were collected and analyzed for anti-Tn antibody response using the Tn3G6K(Biot)G glycopeptide (IgM in A and IgG in B). No sera binding was observed in ELISA using the unglycosylated STTG6K (Biot)G peptide as coating antigen (data not shown). Results are expressed as the mean of individual antibody titers. Serum titers <100 are considered negative since sera were tested at 1/100 starting dilution.
Figure 14B:
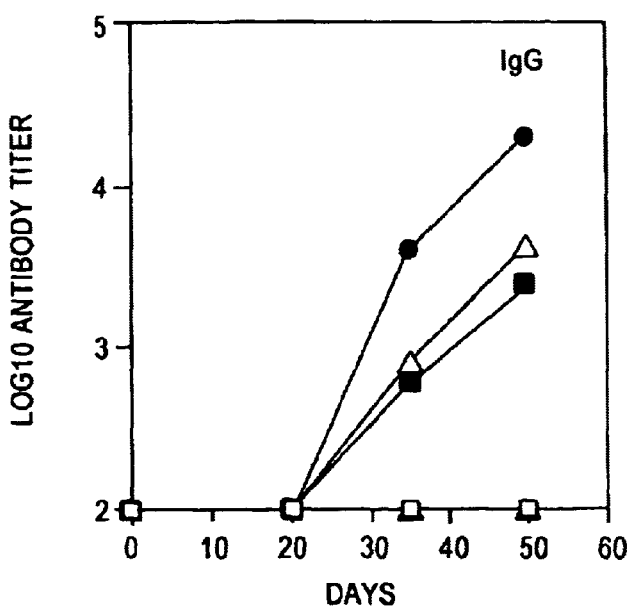

In these conditions, anti-Tn IgM antibodies were detected after immunization with the $Tn_6$-PV peptide and D-($Tn_3$)-PV (FIG. 14A). A slightly lower antibody response was obained when mice were immunized with $Tn_3$-PV. Interestingly, these three short glycopeptides also induced anti-Tn IgG antibodies; however, unexpectedly, the level was somewhat higher for the $Tn_3$-PV glycopeptide than for the D-($Tn_3$)-PV and the $Tn_6$-PV homologues (FIG. 14B). This level, obtained with a linear glycopeptide in the absence of a carrier molecule, is similar to the IgG titer obtained with the dendrimeric MAG construct described earlier (Day et al. (1997)). We checked that no Tn specific antibodies were detected after injection of the PV peptide showing the Tn specificity of the antibodies (FIG. 14B). Interestingly, the Tn-PV glycopeptide did not induce any Tn antibody. This result is in agreement with the lack of recognition of the mono-Tn glycopeptide by the MLS128 mAb (FIG. 13C), and confirm that Tn cluster structures are required for efficient antibody production.

Peptides with contiguous B and T epitopes have been reported to give a protective immune response in the absence of a carrier molecules (Del Guercio et al. (1997), Partidos et al. (1997)). Only a few examples of carbohydrate specific antibodies raised after glycopeptide immunisation have been published. A synthetic glycopeptides containing either a pentasaccharide (MELDAL (1993)) or a repeating unit of 3 α-D-ribose-(1-1)-D-ribitol-5-phosphate (PRP), have been shown to induce quite a good level of antibodies against the carbohydrate part of the proteine (Chong et al. (1997)). We show here that glycopeptides bearing a tri-Tn motif are also able to induce the production of antibodies without the help of a carrier protein.

Figure 15:
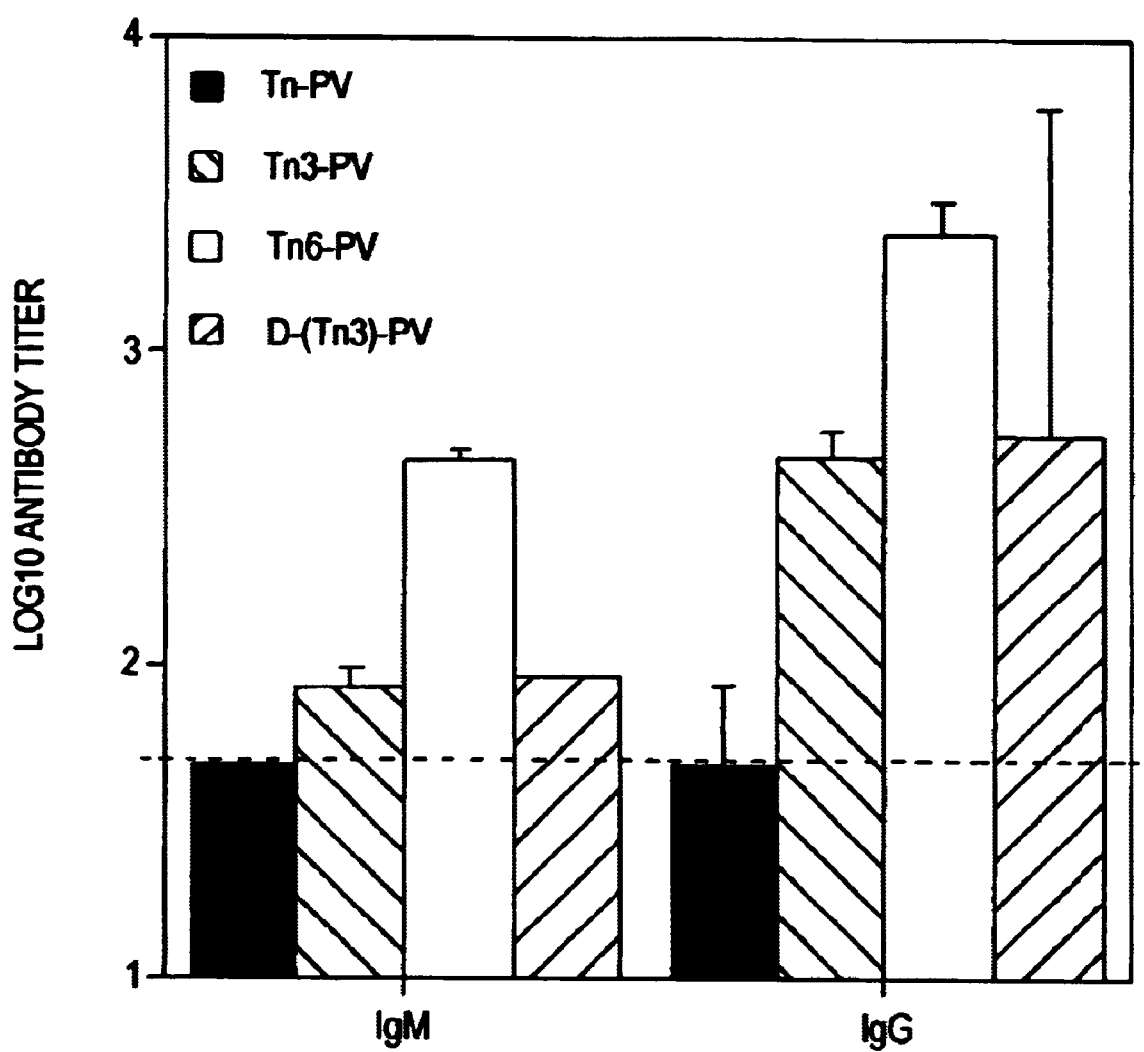
FIG. 15. Anti-Tn antibodies induced in mice immunized with Tn-glycopeptides as measured by FACS using a human tumor cell line bearing the Tn antigen. Flow cytometry analysis was carried out on human Jurkat cells incubated with serial dilutions of sera from BALB/c mice (four per group,) immunized on day 0 with 50 μg of Tn-PV, Tn3-PV, Tn6-PV and D-(Tn3)-PV in CFA, then boosted on days 21 and 42 in IFA with the same antigens. The sera are from mice bled eight days after the last injection. Binding was detected using FITC labeled antibodies specific for mouse IgM, and anti-mouse IgG biotinylated antibodies revealed with streptavidin-PE. Results are expressed as the mean of individual antibody titers calculated as indicated in material and methods section. Serum titer <50 (dashed line) are considered negative since sera were tested at 1/50 starting dilution.

To determine whether these mouse sera were able to recognize the native Tn antigen, we titrated the anti-Tn reactivity obtained after the last immunization using the human Jurkat T lymphoma cells that express the Tn antigen (Nakada et al. (1991)). FIG. 15 shows that sera from BALB/c mice immunized with $Tn_3$-PV, D-($Tn_3$)-PV and $Tn_6$-PV bound this human cell line demonstrating that Tn specific antibodies induced by these glycopeptides recognize the native form of Tn on human tumor cells. However, the pattern of antibody titers is different whether the titration is performed by ELISA using the $Tn_3G_6K$(Biotine)G glycopeptide (FIG. 14) or by FACS (FIG. 15) using the Jurkat cell line. Recognition of the Jurkat cells was better with $Tn_6$-PV than with $Tn_3$-PV induced antibodies (for both IgM and IgG). Interestingly, the antibody production obtained with the tri-D-($Tn_3$) glycopeptide (D-($Tn_3$)-PV) containing three D-serine residues is similar to that obtained with $Tn_3$-PV itself. This result could be useful for the development of the MAC-constructs since it would protect the tri-Tn antigen from hydrolysis by the proteases.

The choice of the tri-Tn motif ($Tn_3G_6KG$) for the ELISA was based on the structural motif recognized by the MLS128 mAb (Nakada et al. (1993)). Although it allows the detection of antibodies raised against the $Tn_3$- or $Tn_6$-PV glycopeptides, it only represents a Tn artificial probe. By contrast, the Tn recognition measured on Jurkat cells by FACS represents a more accurate view of the natural structure available at the cell surface for antibody recognition. In these conditions, the double tri-Tn motif ($Tn_6$-PV) provides a significant benefit over the single tri-Tn motif ($Tn_3$-PV) in the induction of anti-Tn specific IgM and IgG antibodies.

Although the Jurkat cell may not represent the cell prototype for the Tn expression level, no carcinoma cell clones can correctly mimic the natural diversity of mucinous cancer cells. Indeed, unveiling of cryptic Tn on carcinoma cells probably leads to highly variable Tn clusters on mucin-like proteins depending on Ser/Thr content in the aminoacid sequence. We may expect that if the Tn content is high in the glycopeptidic immunogen, the antibody response will be adapted for recognition of various types of natural Tn clusters.

In conclusion, we show here that the conjugation of tri- or hexa-Tn motifs to a linear $CD4^+$ T cell epitope successfully induce anti-Tn antibodies. These results are promising for the further development of dendrimeric MAG constructs bearing tri- or hexa-Tn clusters. Indeed, a stronger response can be expected for these tri-Tn-MAG since the mono-Tn-MAG construct itself, when used in immunotherapy, was already shown to give some protection in tumor bearing mice (Lo Man et al. (1999)).

Example 11

Adjuvant Effect of the Saccharidic Moiety of the Polypeptides of the Invention

The glycopeptides used herein are described in table 4 at the end of this example.

Material and Methods

Cell Lines

The following T cell hybridomas were used: 45G10 is I-$E^d$ restricted and specific for PV peptide (103–115 aa of VP1 protein from poliovirus); FBCD1 is I-$A^d$ restricted is specific for M5 peptide (100–115 aa of *E.coli* MalE protein); CRMA6 and CRMC3 are I-$A^b$ restricted is specific for M5 peptide (100–115 aa of *E.coli* MalE protein).

Different APC cell lines were used: B-cell lymphoma A20 (H-$2^d$; ATCC, Rockville, Md.).

L (I-$A^b$), L (I-$A^d$) and L (I-$L^d$) are fibroblast cell lines transfected respectively with MHC class II I-$A^b$, I-$A^d$ and I-$E^d$ genes and were kindly given by Dr M. Viguier (ICGM, Paris, France).

APC Preparation

BALB/c (H-$2^d$) and C57BL/6 (H-$2^b$) mice were used to prepare different APC.

Activated B cell blast were prepared by stimulating I cell depleted spleen cells for 48 h with LPS. Activated macrophages were prepared from mice injected with thioglycolate after 3 to 5 days by collecting peritoneal exudate cells and 1 hour plastic adherence step in plates.

Dendritic cells were prepared from bone marrow cells cultured for 5 days in the presence of GM-CSF as previously described (K. Inaba et al. (1992)). In these conditions 50 to 70% of the cells were dendritic cells as verified by the presence of the CD11c marker by flow cytometry. This preparation was used directly as APC as enriched DC or further purified at 95% using FACS sorting.

In Vitro T Cell Stimulation Assay

Antigens carrying GalNac or devoid of GalNac were serially diluted and added to APC ($5 \times 10^4$ to $10^5$/well) and to T cell hybridomas ($10^5$/well) in 96-well culture microplates in complete culture medium at 37° C. 24 h after, 100 μl-aliquot supernatants were harvested and frozen for at least 2 h at 70° C. Then $10^4$ cells/well of the IL-2-dependent CTLL cell line were cultured with the supernatant in 0.2 ml final volume. Two days later, $^3$H-thymidine (0.3 μmCi/well: AS=1 Ci/mmol, NEN Life Science, Boston, USA) was added and the cells were harvested 18 h later with an automated cell harvester (Skatron, Lier, Norway). Incorporated thymidine was detected by scintillation counting. In all experiments, each point was done at least in duplicate. Results are expressed in counts per minute (CPM).

1) Increase T Cell Antigenicity of GalNac-glycopeptides is Dependent on the Gal/NAc Ratio Per Molecule.

It has been previously demonstrated that compared to the dendrimeric MAP:PV (see Table 4) addition of a mono-GalNac moiety on a Ser or Thr (i.e. Tn motif at the N-terminus of the four arms of the dendrimeric. MAG:Tn-PV led to a 100–1000 increased stimulation of a T cell hybridoma specific for the PV $CD4^+$ T cell epitope when using the B lymphoma A20 cells as APC.

Figure 18A:
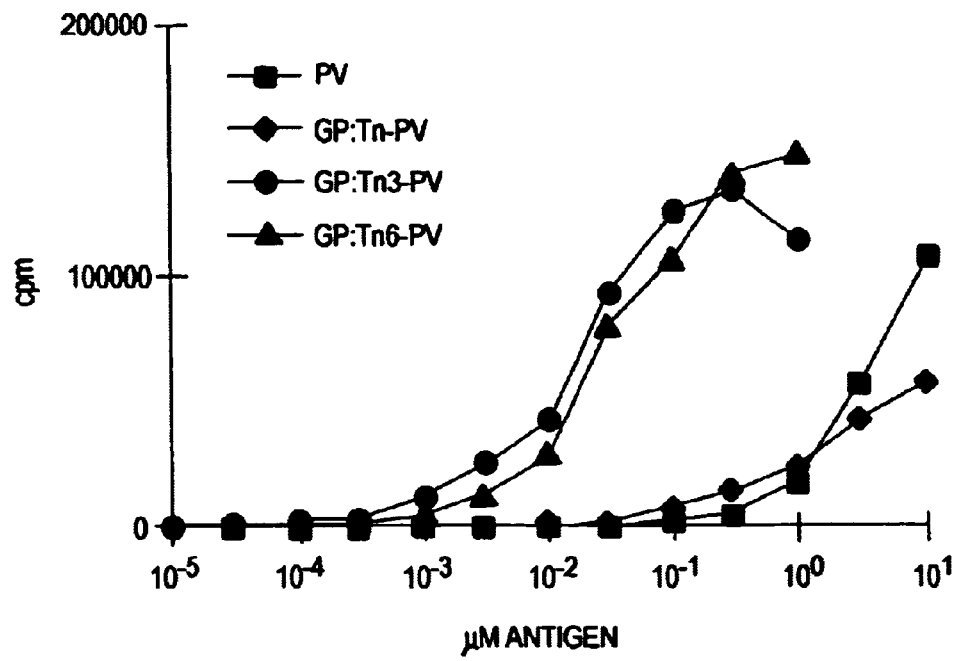
FIG. 18 $10^5$ LPS activated B cell blasts were incubated with $10^6$ T cell hybridoma 45G10 specific for PV in the presence of serial dilution of: (A) linear PV peptide or Tn-PV, Tn3-PV, Tn6-PV glycopeptides; (B) MAP:PV, MAG:Tn-PV MAG:Tn3-PV, MAG:Tn6-PV; 24 h-supernatants were tested for IL 2 content using the CTLL cell line.
Figure 18B:
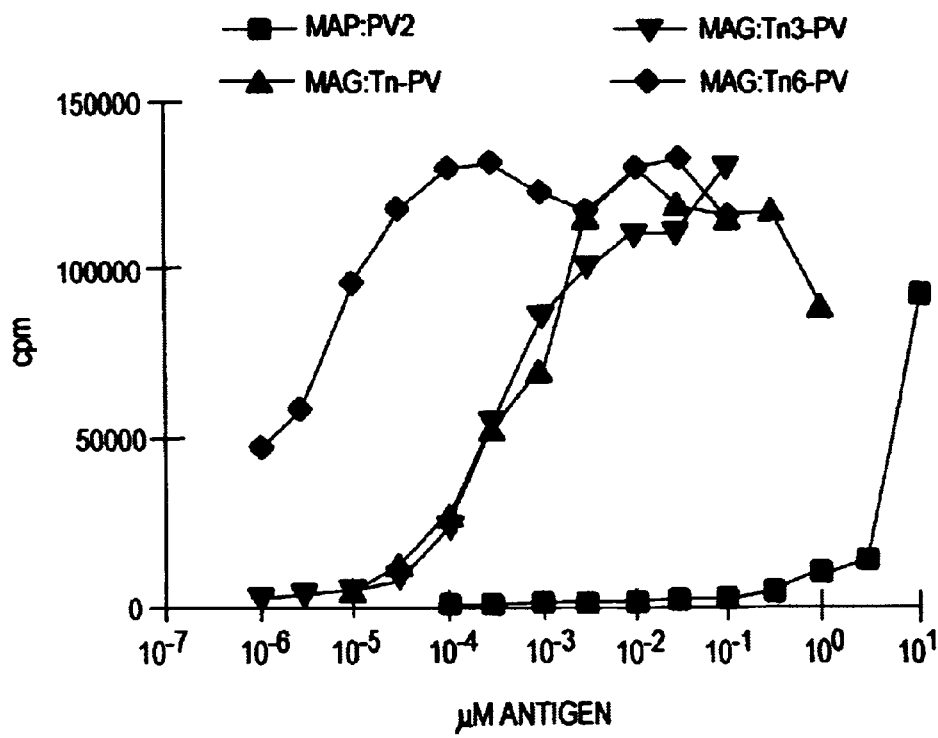
Figure 19A:
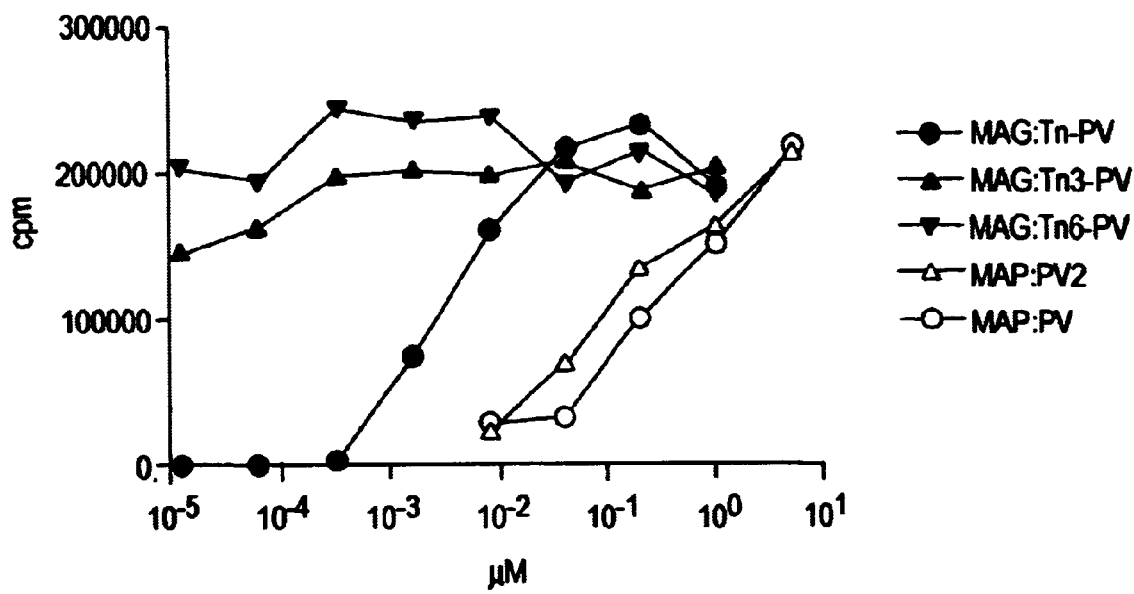
FIG. 19 $5\times10^4$ Dendritic cells (A) or $10^5$ activated macrophages (B) were incubated with serial dilution of MAP:PV, MAG:Tn-PV, MAG:Tn3-PV, MAG:Tn6-PV, together with $10^5$ T cell hybridoma 45G10 specific for PV. 24 h-supernatants were tested for IL-2 content using the CTLL coil line.
Figure 19B:
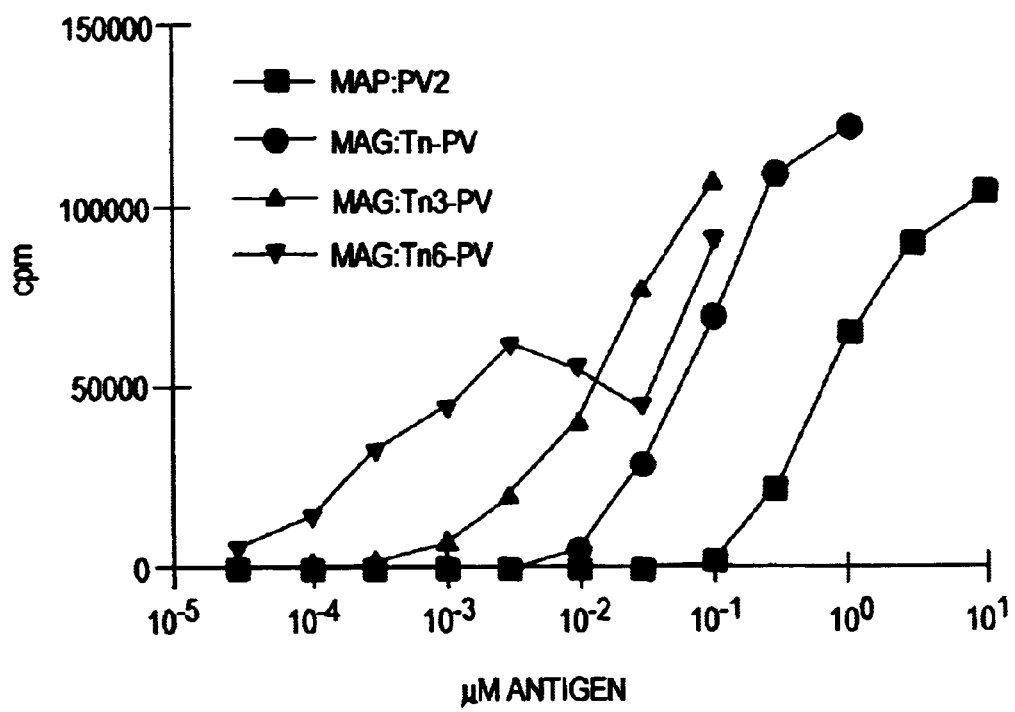
Figure 20:
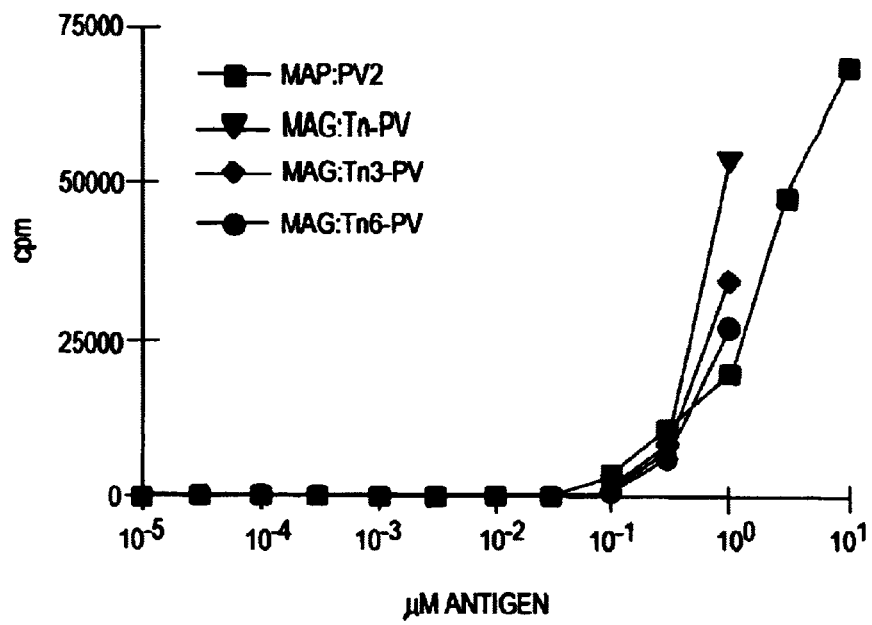
FIG. 20 $10^6$ I-E$^d$ transfected L cells were incubated with serial dilutions of MAP:PV, MAG:Tn-PV MAG:Tn3-PV, MAG:Tn6-PV, together with $10^5$ T cell hybridoma 45G10 specific for PV. 24 h-supernatants were tested for IL-2 content using the CTLL cell line.
Figure 21:
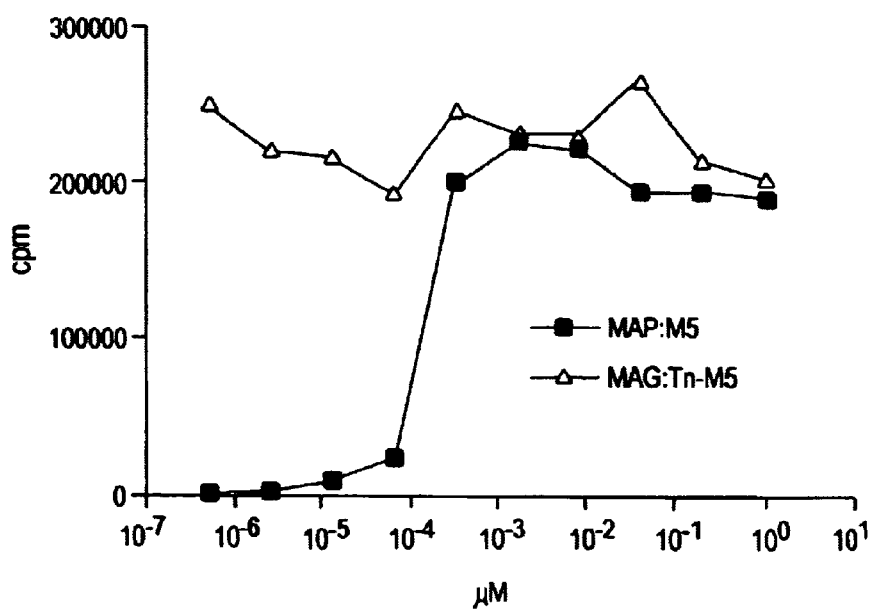
FIG. 21 Dendritic cells ($5\times10^4$) were incubated with serial dilutions of the MAG:Tn-M5, the MAP:M5 or the M5 peptide, together with $10^6$ T cell hybridoma FBCD1 (A) or CRMC3 (B) specific for M5/I-A$^d$ and M5/I-A$^b$ and incubated at 37° C. for 24 h. 24 h-supernatants were tested for IL-2 content using the CTLL cell line.
Figure 22:
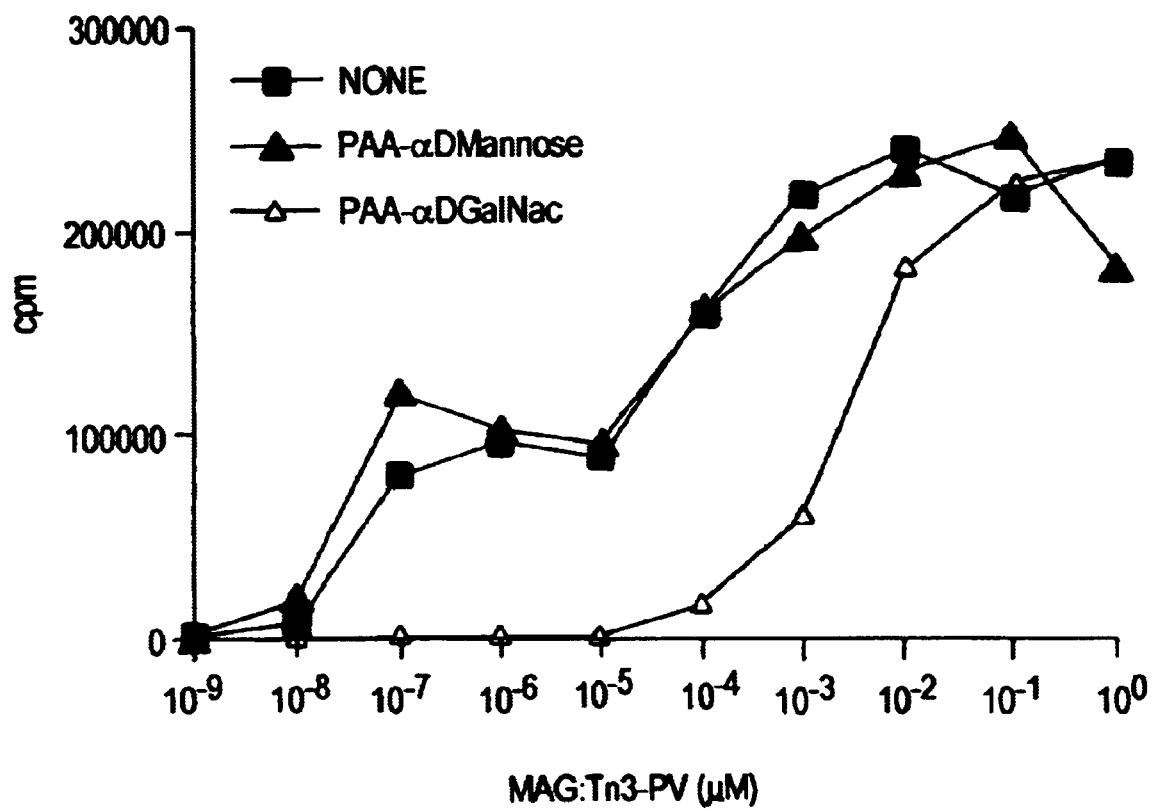
FIG. 22 Dendritic cells ($5\times10^4$) were incubated with serial dilutions of the MAG:Tn3-PV alone or in the presence of PAA-GalNac or PAA-Mannose. Then, 45G10 T cell hybridoma ($10^5$) was added and incubated at 37° C. for 24 h. 24 h-supernatants were tested for IL-2 content using the CTLL cell line.

In order, to further document this phenomenon, different linear glycopeptide and MAG based on the PV peptide $CD4^+$ T cell epitope with various ratio of GalNac residues (see Table 4) were tested using LPS activated B cell blasts as APC When LPS activated B cell blasts are incubated with various concentrations of the linear PV peptide or the parent glycopeptides carrying one, three and six consecutive copies of Tn (respectively: GP:Tn-PV. GP:Tn3-PV and GP:Tn6-PV), it can be seen that all compounds stimulate the 45G10 T cell hybrid specific for the PV peptide (FIG. 18A). However, the addition of three or six Tn per molecule increases the antigenicity of the I cell epitope about a 100-fold as compared to the minimum amount of unglycosylated PV peptide required to stimulate the PV specific T cells. To confirm these results, dendrimeric MAG:Tn PV, MAG:Tn3-PV and the MAG:Tn6-PV with respectively four, twelve and 24 GalNac moiety per molecules (see Table 4) were also tested in the same conditions. FIG. 18B illustrates that the stimulation of the PV specific T cell hybrid was increased by a 1000- to 10000 fold for MAGs as compared with the unglycosylated MAP:PV2

These results confirm and further extend the previous results obtained with A20 cells showing that the GalNac moiety is a powerful mean to increase antigen presentation and stimulation of peptide specific T cells.

2) Enhancement of Antigen Presentation for T Cell Stimulation by GalNac is Observed with All Types of Professional APC.

Different APC cells were tested to determine whether or not this phenomenon was limited to activated D cells. For this purpose, dendritic cells were prepared and were incubated with serial dilutions of unglycosylated MAP:PV2 or with glycosylated MAG:Tn PV, MAG:Tn3-PV and the MAG:Tn6-PV and further used to stimulate PV specific T cell hybrid. In these conditions, as shown in FIG. 19A, 100 to more than 10000 fold less amount of antigen was required in the case of glycosylated dendrimeric MAG to stimulate PV specific T cell cells as compared with the unglycosylated MAP:PV2. Similar results are obtained when using activated macrophages as APC (FIG. 19B), indicating no apparent APC type specificity when professional APC were used. In order to determine if the phenomenon observed could be due to an increased interaction of the PV peptide mediated by GalNac to the MHC I-$E^d$ presenting molecule, we tested non professional APC, i.e. MHC class II transfected murine L cells. As shown in FIG. 20, no modification of T cell stimulation was observed with the glycosylated MAG:Tn PV, MAG:Tn3-PV and the MAG:Tn6-PV as compared with the MAP:PV. Since the expression of MHC of class II molecules is not sufficient to induce enhanced T cell stimulation, this experiment demonstrates that this effect is not mediated by direct interaction of GalNac with MHC molecules. Moreover, this also shows that the GalNac mediated enhancing effect is not due to a direct interaction with the T cell, but is dependent on the APC. This result shows that the effect of GalNac seems limited to particular cell types, here professional APC, and particularly efficient with dendritic cells which represent the key APC for induction of T cell response in vivo. Altogether, this suggests that the GalNac effect could be mediated by an increased endocytosis of GalNac-antigen by professional APC leading to an increased antigen presentation and stimulation of specific T cells.

3) Generalization of the GalNac Mediated Enhancing Antigen Presentation and T Cell Stimulation In order to determine whether the effect observed with GalNac-PV antigen can be generalize to other T cell epitopes, a MAP compound, and its MAG derivatization carrying GalNac, carrying a $CD4^+$ T cell epitope of the MalE protein (peptide M5 corresponding to as 100–115) were synthesized. The M5 peptide stimulates the CRMA6 and FBCD1 T cell hybridomas in association with the MHC I-$A^d$ and MHC I-$A^b$ molecules, respectively. Dendritic cells were incubated with various concentrations of the M5 peptide or the dendrimeric MAP:M5 and MAG:Tn-M5 (Tn=GalNac-Ser) and used to stimulate tho specific CRMA6 and FBCD1 T cell hybridomas. As seen in FIG. 21 MAG:Tn-M5 stimulated with a 100 fold increase both T cell hybrids compared to the parent MAP:M5 or to the M5 peptide. Those results show that the enhancing effect of the GalNac derivatization of antigen is not limited to the PV peptide and can be generalized to some other MHC class II restricted T cell epitopes.

4) Specific Inhibition of MAG:Tn3-PV Increased T Cell Stimulation by a GalNac Derivative.

In order, to further investigate the particularity of the GalNac moiety, we tested whether the enhancing effect on T cell stimulation could be inhibited by competitive related compounds. For this purpose, dendritic cells were incubated with the MAG:Tn3-PV together with a polyacrylamide bearing repeated units of GalNac (PAA-GalNac). Then, these APC were used to stimulate the 45G10 T cell hybridoma. In these conditions, there is an inhibition of the enhanced antigen presentation and T cell stimulation compared to dendritic cells incubated with the MAG:Tn-PV alone (FIG. 22). This inhibition was specific to GalNac, since when control PAA-mannose were used as competitor, no inhibition was observed. This further confirms that the enhancing effect is due to the GalNac moiety (and maybe to the galactosyl family) and is not related to the mannose, that has been already reported to mediate endocytosis of mannosylated-antigen for antigen presentation to T cells.

Table 4 of compounds:
schematic representation of Tn and derivatives

| Antigen designation | Copy number per molecule: Tn antigen | Copy number per molecule: T epitope (PV or M5) |
|---|---|---|
| GP:Tn-PV | 1 | 1 PV |
| GP:$Tn_3$-PV | 3 | 1 PV |
| GP:$Tn_6$-PV | 6 | 1 PV |
| *MAP:PV2 | 0 | 4 PV |
| MAP:PV | 0 | 4 PV |
| MAG:Tn-PV | 4 | 4 PV |
| MAG:$Tn_3$-PV | 12 | 4 PV |
| MAG:$Tn_6$-PV | 24 | 4 PV |
| M5 | 0 | 1 M5 |
| MAP:M5 | 0 | 4 M5 |
| MAG-Tn-M5 | 4 | 4 M5 |

(PV = KLFAVWKITYKDT (SEQ ID NO:4), M5 - NGKLIAYPIAVEALS (SEQ ID NO:5))
*MAP:PV2 corresponds to the addition of STT unglycosylated aa added to the PV sequence (PV=KLFAVWKITYKDT (SEQ ID No: 4), M5-NGKLIAYPIAVEALS (SEQ ID NO:5))

*MAP:PV2 corresponds to the addition of STT unglycosylated aa added to the PV sequence Although only preferred embodiments are specifically illustrated and described herein it will be appreciated that many modifications and variations of the present invention are possible in the light of the above teachings and within purview of the following appended claims without departing from the spirit and intended scope of the invention.

REFERENCES

Bhavanandan, V. P. (1991) *Glycobiology* 1, 493–503; b) Hakomori, S; (1989) *Adv. Cancer Res.* 52, 257–331; c) Fukuda, M. (1996) *Cancer Res.* 56, 2237–2244.

MacLean, G. D., Reddish, M. A., Bowen-Yacyshyn, M. B., Poppema, S., Longenecker, B. M. (1994) *Cancer Invest.* 12, 46–56.

Springer, G. F. (1984) *Science* 224, 1198–1206; b) Itzkowitz, S. H., Yuan, M., Montgomery, C. K., Kjeldsen, T., Takahashi, H. K., Bigbee, W. L., Kim, Y. S. (1989) *Cancer Res.* 49, 197–204; c) Springer, G. F. (1995) *Crit. Rev. Oncogen.* 6, 57–85; (d) Yamashita, Y., Chung, Y. S., Horie, R., Kannagi, R., Sowa, M. (1995) *J. Natl. Cancer Inst.* 87, 441–446.

Springer, G. F., Desai, P. R., Tegtmeyer, H., Carlstedt, S. C., Scanlon, E. F. (1994) *Cancer Biother.* 9, 7–15.

Singhal, A., Fohn, M., Hakomori, S. (1991) *Cancer Res.* 51, 1406–1411.

O'Boyle, K. P., Zamore, R., Adluri, S., Cohen, A., Kemeny, N., Welt, S., Lloyd, K. O., Oettgen, H. F., Old, L. J., Livingston, P. O. (1992) *Cancer Res.* 62, 5663 5667.

Ratcliffe, R. M., Baker, D. A., Lemieux, R. U. (1981) *Carbohydr. Res.* 93, 35–41.

Fung, P. Y. S., Madej, M., Koganty, R. R., Longenecker, B. M. (1990) *Cancer Res.* 50, 4308–4314.

MacLean, G. D., Bowen-Yacyshyn, M. B., Samuel, J., Meikle, A., Stuart, G., Nation, J., Poppema, S., Jerry, M., Koganty, R., Wong, T., Longenecker, B. M. (1992) *J. Immunotherap.* 11, 292–305.

Longenecker, B. M., Reddish, M., Koganty, R., MacLean, G. D. (1993) in *Specific immunotherapy of cancer with vaccines* (Bystryn, J. C., Ferrone, S., Livington, P Eds.), Ann. N. Y. Acad. Sci. 690, 276–291.

Helling, F., Zhang, S., Shang, A., Adluri, S., Calves, M., Koganty, R., Longenecker, B. M. (1995) *Cancer Res.* 55, 2783–2788.

(a) Toyokuni, T., Hakomori, S., Singhal, A. K. (1994) *Bioorg. Med. Chem.* 2, 1119–1132; (b) Toyokuni, T., Dean, B., Cal, S., Bolvin, D., Hakomori, S., Singhal, A. K. (1994) *J. Am. Chem. Soc.* 116, 395–396, c) Toyokuni, T., Singhal, A. K. (1995) *Chem. Soc. Rev.,* 231–242.

(a) Posnett, D. N., McGrath, H., Iam, J. P. (1988) *J. Biol. Chem.* 263, 1719–1726; (b) Tom, J. P. (1988) *Proc. Natl. Acad. Sci. USA* 85, 5409-5413.

Tam, J. P. (1994) in *Peptide antigens: A Practical Approach* (Wisdow, G. B. Eds), Oxford University Press, 83–115 and references cited herein Leclerc, C., Deriaud, D., Mimic, V., Van der Werf, S. (1991) *J. Virol.* 65, 711–718.

Roy, R., Zanini, D., Romanowska, A., Meunier, S. J., Park, W. K. C., Gidney, M. A., Harrison, B., Bundle, D. R., Williams, R. E. Abstract of poster, XIII International Carbohydrate Symposium (Jul. 17–22, 1994).

Lett, E., Klopfenstein, C., Klein, J-P., Schöller, M., Wachsmann, D. (1995) *Infect. Immun.* 63, 2645–2651.

Tam, J. P., Clavijo, P., Lu, Y., Nussenzweig, V., Nussenzweig, R., Zavala, F. (1990) *J. Exp. Med.* 171, 299–306.

(a) Paulsen, H., Holck, J-P. (1982) *Carbohydr. Res.* 109, 89–107; (b) Paulsen, H., Schultz, M., Klamann, J-D., Waller, B., Paal, M. (1985) *Liebigs Ann. Chem.* 2028–2048.

Paulsen, H., Adermann, K. (1989) *Liebigs Ann. Chem.* 751–759.

Shafizadeh, F. (1963) *Methods Carbohydr. Chem.* 2, 409–410.

a) Vowinkel, E. (1967) *Chem. Ber.* 100, 16–22; b) Schultz, M., Kunz, H. (1993) Tetrahedron Assym. 4, 1205–1220.

(a) Lomieux. R. U., Ratcliffe, R. M. (1979) *Can. J. Chem.* 57, 1244–1251; (b) Ferrari, B., Pavia, A. A. (1980) *Carbohydr. Res.* 79, C1–C7.

(a) Filira, F., Biondi, L., Cavaggion, F., Scolaro, B., Rocchi, R. (1990) *Int. J. Peptide Protein Res.* 36, 86–96 (b) Otvos, L., Urge, L., Hollosi, M., Wroblewski, K., Graczyk, G., Fasman, G. D., Thurin, J. (1990) *Tetrahedron Lett.* 31, 5889–5892.

a) Paulsen, H., Merz, G., Weichert, U. (1988) *Angew. Chem. Int. Ed. Engl.* 27, 1305–1367; b) Jansson, A. M., Meldal, M., Bock, K. (1990) *Tetrahedron. Lett.* 31, 6991–6994; c) Peters, S., Bielfeldt, T., meldal, M., Bock, K., Paulsen, H. (1992) *Tetrahedron Lett.* 33, 6445–6448.

Pancino, G., Osinaga, E., Vorauher, W., Kakouche, A., Mistro, D., Charpin, C., Roseto, A. (1990) *Hybridoma* 9, 389–395.

Numata, Y., Nakada, H., Fukui, S., Kitagawa, H., Ozaki, K., Inoue, M., Kawasaki, T., Funakoshi, I., Yamashina, I. (1990) *Biochem. Biophys. Res. Commun.* 170, 981–985.

Nakada, H., Numata, Y., Inoue, M., Tanaka, N., Kitagawa, H., Funakoshi, I., Fukui, S., Yamashina, I. (1991) *J. Biol. Chem.* 266, 12402–12405.

Kaiser, E., Colescott, R. L., Bossinger, C. D., Cook, P. I. (1980) *Anal. Biochem.* 34, 595–598.

Walker, B. (1994) In Peptide antigens (Wisdow, G. B. Eds), Oxford University Press, The Practical Approach Series, 27–81.

Melenhofer, J., Waki, M., Hoimer, E. P., Lambros, T. J., Makofske, R. C., Chang, C. D. (1979) *Int. J. Pept. Protein Res.* 13, 36–42.

(a) Tettamanti, G., Pigman, W. (1968) *Arch. Biochem. Biophys.* 124, 41–50; (b) Osinaga, E., Rabino, A., Grosclaude, J., Cairoll, E., Batthyany, C., Bianchi, S., Signorelli, S., Varangof, M., Musé, I., Roseto, A. (1996) *Int. J. Oncol.* 8, 401–406.

Leclerc, C., Sedlik, C., Lo-Man, R., Charlot, B., Rojas, M., Deriaud, E. (1995) *Eur. J. Immunol.* 25, 2533–2538.

Itzkowitz, S. H., et al. Sialosyl-Tn. A novel mucin antigen associated with prognosis in colorectal cancer patients. *Cancer,* 66, 1960–6 (1990).

Deshpande, P. P. & Danishefsky, S. J. Total synthesis of the potential anticancer vaccine kh-1 adenocarcinoma antigen. *Nature* 387, 164–166 (1997).

Sames, D., Chen, X. T. & Danishefsky, S. J. Convergent total synthesis of a tumour-associated mucin motif. *Nature* 389, 587–591 (1997).

Herzenberg, L. A., Tokuhisa, T. & Herzenberg, L. A. Carrier-priming leads to hapten-specific suppression. *Nature* 285, 664–7 (1980).

Schutze, M. P., Leclerc, C., Jolivet, M., Audibert, F. & Chedid, L. Carrier-induced opitopic suppression, a major issue for future synthetic vaccines. *J. Immunol.* 135, 2319–22 (1985).

Kim, Y. J. & Varki, A. Perspectives on the significance of altered glycosylation of glycoproteins in cancer. *Glycoconj. J.* 14, 569–576 (1997).

Ray, S., et al. Preparation of a multiple antigen glycopeptide (MAG) carrying the Tn antigen—a possible approach to a synthetic carbohydrate vaccine. *J. Pep. Res.* 49, 620–625 (1997).

Panina-Bordignon, P., et al. Universal Immunogenic T cell epitopes: promiscuous binding to human MHC class II and promiscuous recognition by T cells. *Eur. J. Immunol.* 19, 2237–2242 (1989).

Reece, J. C., Geysen, H. M. & Rodda, S. J. Mapping the major human T helper epitopes of tetanus toxin. The emerging picture, *J. Immunol.* 151, 6175–6184 (1993).

Etlinger, H. M., et al. Use of prior vaccinations for the development of new vaccines, *Science* 249, 423–5 (1990).

Goydos. J. S., Elder, E., Whiteside, T. L., Finn, O. J. & Lotze, M. T. A phase I trial of a synthetic mucin peptide vaccine. Induction of specific immuno reactivity in patients with adenocarcinoma. *J. Surg. Res.* 63, 298–304 (1996).

Chong, P., et al. A strategy for rational design of fully synthetic glycopeptide conjugate vaccines. *Infect. Immun.* 65, 4918–4925 (1997).

Meinjohanns, E., Vorgas Berenguol, A., Meldal, M., Paulsen, H. & Bock, K. Comparison of N-Dts and N-Aloc in the solid phase syntheses of O-GlcNAc glycopeptide fragments of RNA-polymerase, II and mammalian neurofilaments. *J. Chem. Soc. Perkin Trans I*, 2165–2175 (1995).

Reimer K B, Meldal M, Kusumotos Fukase K, Bock K., J. Chem. Soc. P.I. (1993) pp 925–932.

Springer, G. F. T and Tn, general carcinoma autoantigens. Science, 224: 1198–1206, 1984.

MacLean, G. D., Reddish, M., Koganty, R. R., Wong, T., Gandhi, S., Smolenski, M., Samuel, J., Nabholtz, J. M., and Longenecker, B. M. Immunization of breast cancer patients using a synthetic sialyl-Tn glycoconjugate plus Detox adjuvant. Cancer Immunol. Immunother. 36: 215–222, 1993.

Toyokuni, T., Hakomori, S., and Singhal, A. K. Synthetic carbohydrate vaccines: synthesis and immunogenicity of Tn antigen conjugates. Bioorg. Med. Chem. 2: 1119–1132, 1994.

Deshpande, P. P. and Danishefsky, S. J. Total synthesis of the potential anticancer vaccine kh-1 adenocarcinoma antigen. Nature, 387: 164–166, 1997.

Sames, D., Chen, X. T., and Danishefsky, S. J. Convergent total synthesis of a tumour-associated mucin motif. Nature, 389: 587–591, 1997.

Kim, Y. J. and Varki, A. Perspectives on the significance of altered glycosylation of glycoproteins in cancer. Glycoconj, J. 14: 509–576, 1997.

Kitamura, K., Stockert, E., Garin-Chesa, P., Welt, S., Lloyd, K. O., Armour, K. L., Wallace, T. P., Harris, W. J., Carr, F. J., and Old, L. J. Specificity analysis of blood group Lewis-y (Le(y)) antibodies generated against synthetic and natural Le(y) determinants. Proc. Natl. Acad. Sci. USA. 91: 12957 12961, 1994.

Helling, F., Zhang, S., Shang, A., Adluri, S., Calves, M., Koganty, R., Longenecker, B. M., Yao, T. J., Oettgen, H. F., and Livingston, P. O. GMZ-KLH conjugate vaccine: increased immunogenicity in melanoma patients after administration with immunological adjuvant QS-21. Cancer Res. 55: 2783–2788, 1995.

Herzenberg, L. A., Tokuhisa, T., and Herzenberg, L. A. Carrier-priming leads to hapten-specific suppression. Nature. 285: 664–667, 1980.

Schutze, M. P., Leclerc, C., Jolivet, M., Audibert, P., and Chedid, L. Carrier-induced epitopic suppression, a major issue for future synthetic vaccines. J. Immunol. 135: 2319–2322, 1985.

Bay, S., Lo-Man, R., Osinaga, E., Nakada, H., Leclerc, C., and Cantacuzene, D. Preparation of a multiple antigen glycopeptide (MAG) carrying the Tn antigen—a possible approach to a synthetic carbohydrate vaccine. J. Pept. Res. 49: 620–625, 1997.

Lemieux, R. U. and Ratcliffe, R. M. The azidonitration of tri-O-acetyl-D-galactal. Can. J. Chem. 47: 1244–1251, 1979.

Ferrari, B. and Pavia, A. A. The synthesis or derivatives of 3-O-(2-acetamido-2-deoxy-a-D-galactopyranosyl)-L-serine and -L-threonine. Carbohydr. Res. 79: C1–C7, 1980.

Lo-Man, R., Martineau, P., Manoury-Schwartz, B., Hofnung, M., and Leclerc, C. Overcoming the crypticity of a viral T cell determinant by insertion into a bacterial chimeric protein. Int. Immunol. 8: 1245–1255, 1996.

Numata, Y., Nakada, H., Fukui, S., Kitagawa, H., Ozaki, K., Inoue, M., Kawasaki, T., Funakoshi, I., and Yamashina, I. A monoclonal antibody directed to Tn antigen. Biochem. Biophys. Res. Com. 170. 981–985, 1990.

Deck, B. Elofsson, M., Kihlberg, J., and Unanue, E. R. Specificity of glycopeptide-specific T cells. J. Immunol. 155: 1074–1078, 1995.

Jensen, T., Hansen, P., Galli-Stampino, L., Mouritsen, S., Frische, K., Meinjohanns, E., Meldal, M., and Werdelin, O. Carbohydrate and peptide specificity of MHC class II-restricted T cell hybridomas raised against an O-glycosylated self peptide. J. Immunol. 158: 3769–3778, 1997.

Nakada, H., Numata, Y., Inoue, M., Tanaka, N., Kitagawa, H., Funakoshi, I., Fukui, S., and Yamashina, I. Elucidation of an essential structure recognized by an anti-GalNAc alpha-Ser(Thr) monoclonal antibody (MLS 128). J. Biol. Chem. 266: 12402–12405. 1991

Nakada, H., Inoue, M., Numata, Y., Tanaka, N., Funakoshi, I., Fukui, S., Mellors, A., and Yamashina, I. Epitopic structure of Tn glycophorin A for an anti-Tn antibody (MLS 128). Proc. Natl. Acad. Sci. USA. 90: 2495–2499, 1993.

Nakada, H., Inoue, M., Tanaka, N., Numata, Y., Kitagawa, H., Fukui, S., and Yamashina, I. Expression of the Tn antigen on T-lymphoid cell line Jurkat. Biochem. Biophys. Res. Com. 179: 762–767, 1991.

Fung, P. Y., Madej, M., Koganty, R. R., and Longenecker, R. M. Active specific immunotherapy of a murine mammary adenocarcinoma using a synthetic tumor-associated glycoconjugate. Cancer Res. 50: 4308–4314, 1990.

Singhal, A., Fohn, M., and Hakomori, S. Induction of alpha-N-acetylgalactosamine-O-serine/threonine (Tn) antigen-mediated cellular immune response for active immunotherapy in mice. Cancer Res. 51: 1406–1411, 1991.

Van den Eijnden, D. H., Evans, N. A., Codington, J. F., Reinhold, V., Silber, C., and Jeanloz, R. W. Chemical structure of epiglycanin, the major glycoprotein of the TA3-Ha ascites cell. The carbohydrate chains. J. Biol. Chem. 264: 12153–12160, 1979.

Hauschka, T. S., Weiss, L., Holdridge, B. A., Cudney, T. L., Zumpft, M., and Planinsek, J. A. Karyotypic and surface features of murine TA3 carcinoma cells during immunoselection in mice and rats. J. Natl. Cancer Inst. 47: 343–359, 1971.

Adluri, S., Helling, F., Ogata, S., Zhang, S., Itzkowitz, S. H., Lloyd, K. O., and Livingston, P. O. Immunogenicity of synthetic TF-KLH (keyhole limpet hemocyanin) and sTn-KLH conjugates in colorectal carcinoma patients. Cancer Immunol. Immunother. 41: 185–192, 1995.

Reddish, M. A., MacLean, G. D., Poppema, S., Berg, A., and Longenecker, B. M. Pre-immunotherapy serum CA27.29 (MUC-1) mucin level and CD69+ lymphocytes correlate with effects of Theratope sialyl-Tn-KLH cancer vaccine in active specific immunotherapy. Cancer Immunol. Immunother. 42: 303–309, 1996.

Chong, P., Chan, N., Kandil, A., Tripet, B., James, O., Yang, Y. P., Shi, S. P., and Klein, M. A strategy for rational design of fully synthetic glycopeptide conjugate vaccines. Infect. Immun. 65: 4918–4925, 1997.

Haurum, J. S., Arsequell, G., Lellouch, A. C., Wong, S. Y. C., Dwek, R. A., McMichael. A. J., and Elliott, T. Recognition of carbohydrate by MHC complex class I-restricted, glycopeptide-specific T lymphocytes. J. Exp. Med. 180: 739–744, 1994.

Zhang, S., Walberg, L. A., Ogata, S., Itzkowitz, S. H., Koganty, R. R., Reddish, M., Gandhi, S. S., Longenecker, B. M., Lloyd, K. O., and Livingston, P. O. Immune sera and monoclonal antibodies define two configurations for the sialyl Tn tumor antigen. Cancer Res. 55: 3364–3368, 1995.

Kuduk, S. D., Schwarz, J. B., Chen, X. T., Glunz, P. W., Sames, D., Ragupathi, G., Livingston. P. O., and Danishefsky, S. J. Synthetic and immunological studies on clustered modes of mucin-related Tn and TF O-linked antigens: The preparation of a glycopeptide-based vaccine for clinical trials against prostate cancer. J. Am. Chem. Soc. 120: 12474–12485, 1995.

Ogata, S., Koganty, R., Reddish, M., Longenecker, B. M., Chen, A. L., Perez, C., and Itzkowitz, S. H. Different modes of sialyl-Tn expression during malignant transformation of human coloni mucosa. Glycoconjug. J. 15: 29–35, 1998.

Livingston, P. O. Augmenting the immunogenicity of carbohydrate tumor antigens. Sem. Cancer Biol. 6: 357–366, 1995.

Panina Bordignon, P., Tan, A., Termijtelen, A., Demotz, S., Corradin, G., and Lanzavecchia, A. Universal immunogenic T cell epitopes: promiscuous binding to human MHC class II and promiscuous recognition by T cells. Eur. J. Immunol. 19: 2237–2242, 1989.

Reece, J. C., Geysen, H. M., and Rodda, S. J. Mapping the major human T helper epitopes of tetanus toxin. The emerging picture. J. Immunol. 151: 6175–6184, 1993.

Etlinger, H. M., Gillessen, D., Lahm, H. W., Matile, H., Schonfeld, H. J., and Trzeciak, A. Use of prior vaccinations for the development of new vaccines. Science. 249: 423–426, 1990.

Franke, E. D., Corradin, G., and Hoffman, S. L. Induction of protective CTL responses against the P. yoelii cicumsporozoite protein by immunization with peptides. J. Immunol. 159: 3424–3433, 1997.

Goydos, J. S., Elder, E., Whiteside, T. L., Finn, O. J., and Lotze. M. T. A phase I trial of a synthetic mucin peptide vaccine. Induction of specific immune reactivity in patients with adenocarcinoma. J. Surg. Res. 63: 298 304, 1996.

Alexander, J., J. Sidney, S. Southwood, J. Ruppert, C. Oseroff, A. Maewal, K. Snoke, H. M. Serra, R. T. Kubo, A. Sette, and H. M. Grey, 1994. Development of high potency universal DR-restricted helper epitopes by modification of high affinity DR-blocking peptides. Immunity. 1:751–761.

Chaux, P., V. Vantomme, V. Stroobant, K. Thielemans, J. Corthals, R. Luiten, A. M. M. Eggermont, T. Boon, and P. J. E. M. van der Bruggen, 767–777, 1999. J. Exp. Med. 189:767–777.

Comerford, S. A., D. J. McCance, G. Dougan, and J. P. Tite. 1991. J. Virol. 65:4681.

Disis, M. L., E. Calenoff, C. McLaughlin, A. E. Murphy, W. Chen, B. Groner, M. Jesschke, N. Lydon, E. McGlynn, R. B. Livingston, R. Moe, and M. A. Cheever. 1994. Cancer Res. 54:16.

Panina-Bordignon, P., A. Tan, A. Termijtelen, S. Demotz, G. Corradin, and A. Lanzavecchia, 1989. Universal Immunogenic T cell epitopes: promiscuous binding to human MHC class II and promiscuous recognition by T cells. Eur. J. Immunol. 19:2237–2242.

Peace, D. J., W. Chen, H. Nelson, and M. A. Cheever, 1991. J. Immunol. 146:2059.

Reece, J. C., H. M. Geysen, and S. J. Rodda, 1993. Mapping the major human T helper epitopes of tetanus toxin. The emerging picture. J. Immunol. 151:6175–6184.

F. Sallusto, M. Cella, C. Danieli, A. Lanzavecchia, J. Exp. Med. 182, 389–400 (1995).

J. C. Reece, H. M. Geysen, S. J. Rodda, J. Immunol. 151, 6175–6184 (1993).

P. Panina-Bordignon, et al., EurJ.Immunol. 19, 2237–2242 (1989).

J. Alexander, et al., Immunity 1, 751–761 (1994).

S. A. Comerford, D. J. McCance, G. Dougan, J. P. Tite, J. Virol. 65, 4681 (1991).

D. J. Peace, W. Chen, H. Nelson, M. A. Cheever, J. Immunol. 146, 2059.

M. L. Disis, et al., Cancer Res. 54, 16 (1994).

P. Chaux, et al., J. Exp. Med. 189, 767–777 (1999).

I. F. McKenzie, et al., Veterinary Immunology & Immunopathology 63, 185–90 (1998).

V. Karanikas, et al., Journal of Clinical Investigation 100, 2783–92 (1997).

N. Suzuki, K. Yamamoto, S. Toyoshima, T. Osawa, T. Irimura, Journal of Immunology 156, 128–35 (1996).

T. Eto, H. Takahashi, Nature Med. 5, 577–581 (1999).

K. Kawakami, K. Yamamoto, S. Toyoshima, T. Osawa, T. Irimura, Japanese Journal of Cancer Research 85, 744–9 (1994).

K. Inaba, et al., Journal of Experimental Medicine 176, 1093–702 (1992).

Hakomori, S. (1989) Adv. Cancer Res. 52, 257–331

Bhavanandan, V. P. (1991) Glycobiology 1, 493–503

Fukuda, M. (1996) Cancer Res. 56, 2237–2244

MacLean, C. D., Reddish, M. A., Bowen-Yacyshyn, M. B., Poppema, S., and Longenecker, B. M. (1994) Cancer Invest. 12(1), 46–56

Helling, F., Zhang, S., Shang, A., Adluri, S., Calves, M., Koganty, R., Longenecker, B. M., Yao, T.-J., Oettgen, H. F., and Livingston, P. O. (1995) Cancer Res. 55, 2783–2788

Reddish, M. A., Jackson, L., Koganty, R. R., Qiu, D., Hong, W., and Longenecker, B. M. (1997) Glycoconjugate journal 14, 549–560

Fung, P. Y. S., Madej, M., Koganty, R. R., and Longenecker, B. M. (1990) Cancer Res. 50, 4308–4314

MacLean, G. D., Bowen-Yacyshyn, M. B., Samuel, J., Meikle, A., Stuart, G., Nation, J., Poppema, S., Jerry, M., Koganty, R., Wong, T., and Longenecker, B. M. (1992) J. Immunotherap. 11, 292–305

Ray, S., Lo-Man, R., Osinaga, E., Nakada, H., Leclerc, C., and Cantacuzene, D. (1997) J. Peptide Res. 49, 620–625

Lett, E., Klopfenstein, C., Klein, J.-P., Schöller, M., and Wachsmann, D. (1995) Infection and Immunity 63, 2645–2651

Tam, J. P. (1988) Proc. Natl. Acad. Sci. USA 85, 5409–5413

Posnett, D. N., McGrath, H., and Tam, J. P. (1988) J. Biol. Chem. 263(4), 1719–1725

Tam, J. P. (1994) Peptide antigens, A practical approach (Wisdow. G. B., Ed.), Oxford University Press, London Leclerc, C., Deriaud, D., Mimic, V., and Van der Werf, S. (1991) J. Virol. 65, 711–718

Lo-Man, R., Bay, S., Vichier-Guerre, S., Deriaud, E., Cantacuzene, D., and Leclerc, C. (1999) Cancer Res. 59, 1520–1524

Numata, Y., Nakada, H., Fukui, S., Kitagawa, H., Ozaki, K., Inoue, M., Kawasaki, T., Funakoshi, I., and Yamashima, I. (1990) Biochem. Biophys. Res. Commun. 170, 981–985

Nakada, H., Numata, Y., Inoue, M., Tanaka, N., Kitagawa, H., Funakoshi, I., Fukui, S., and Yamashima, I. (1991) J. Biol. Chem. 266, 12402–12405

Nakada, H., Inoue, M., Numata, Y., Tanaka, N., Kunakoshi, I., Fukui, S., Mellors, A., and Yamashina, I. (1993) Proc. Natl. Acad. Sci. USA 90, 2495–2499

Toyokuni, T., Hakomori, S., and Singhal, A. K. (1994) Bioorg. Med. Chem. 2, 1119–1132

McCool, D. J., Forstner, J. F., and Forstner, G. G. (1994) Biochem. J. 302(Pt 1), 111–118

Inoue, M., Nakada, H., Tanaka, N., and Yamashina, I. (1994) Cancer Res. 54, 85–88

Toyokuni, T., Dean, B., Cai, S., Bolvin, D., Hakomori, S., and Singhal, A. K. (1994) *J. Amer. Chem. Soc.* 116, 395–396

Paulsen, H., and Hölck, J.-P. (1982) *Carbohydr. Res.* 109, 89–107

Paulsen, H., and Adermann, K. (1989) *Liebigs Ann. Chem.*, 751–759

Shafizadeh, F. (1903) *Meth. Carbohydr. Chem.* 2, 409–410

Schultz, M., and Kunz, H. (1993) *Tetrahedron Assym.* 4(6), 1205–1220

Vowinkel, F. (1967) *Chem. Ber.* 100, 16–22

Lemieux, R. U., and Ratcliffe, R. M. (1979) *Can. J. Chem.* 57, 1244–1251

Ferrari, B. P., A. (1980) *Carbohydr. Res.* 79, C1–C7

Paulsen, H., Schultz, M., Klamann, J.-D., Waller, B., and Paal, M. (1985) *Liebigs Ann. Chem.*, 2028–2048

Fields, C. G., Llyod, D. H., Macdonald, R. L., Otteson, K. M., and Noble, R M (1991) *Peptide Res.* 4, 95–101

Elofsson, M., Roy, S., Walse, B., and Kihlberg, I. (1993) *Carbohydr. Res.* 246, 89–103

Anisfeld, S. T., and Lansbury, P. T (1990) *J. Org Chem* 55, 5580–5562

Kates, S. A., De la Tore, B. G., Eritia, R., and Albericio, F. (1994) *Tetrahedron Lett.* 35, 1033–1034

Filira, F., Biondi, L., Cavaggion, F., Scolaro, B., and Rocchi, R. (1990) *Int. J. Peptide Protein Res.* 36, 86–96

Urge, L., Gorbics, L., and Otvos, L. (1992) *Biochem. Biophys. Res. Commun.* 184(2), 1125–1132

Otvos, L., Urge, L., Hollosi, M., Wroblewski, K., Graczyk, G., Fasman, G. D., and Thurin, J. (1990) *Tetrahedron Lett.* 31, 5889–5892

Inoue, M., Yamashina, I., and Nakada, H. (1995) *Biochem. Biophys. Res. Commun.* 245, 23–27

Del Guercio, M. E., Alexander, J., Kubo, R. T., Arrhenius, T., Maewal, A., Appella, E., Hoffman, S. I., Jones, T., Valmori, D., Sakaguchi, K., Grey, H. M., and Sette, A. (1997) *Vaccine* 16(4), 441–448

Brumeanu, T. D., Casares, S., Bot, A., Bot, S., and Bona, C. A. (1997) *J. of Virology* 71, 5473–5480

Obeid, O. E., Partidos, C. D., Howard, C. R., and Steward, M. W. (1995) *J. of Virology* 69, 1420–1428

Partidos, C. D., Ripley, J., Delmas, A., Obeid, O. E., Denbury, A., and Steward, M. W. (1997) *J. of General Virology* 78, 3227–3232

Chong, P., Chan, N., Kandil, A., Tripet, B., James, O., Yang, Y.-P., Shi, S.-P., and Klein, M. (1997) *Infection and Immunity* 65, 4918–4925

What is claimed is:

1. A carbohydrate peptide conjugate selected from the group consisting of the conjugates of the following formulae (a) to (f):

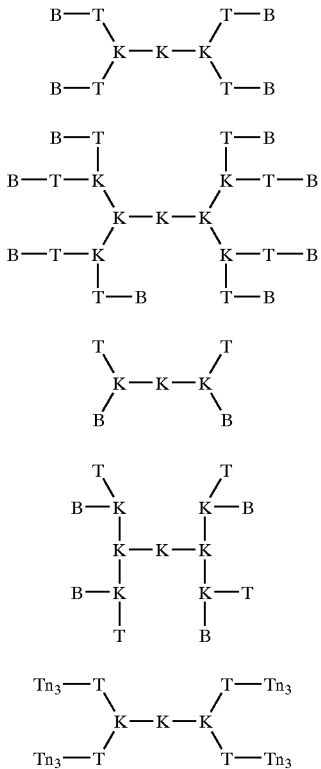

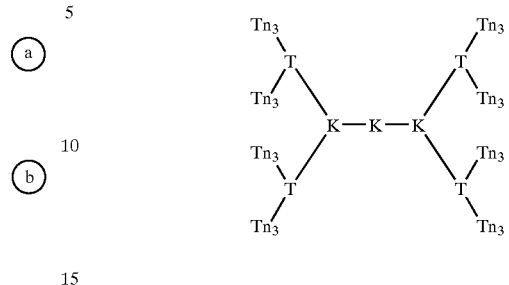

wherein:

K is a lysyl residue,

T is a CD4 T$^+$ cell peptide epitope;

B and Tn is a Tn antigen selected from the group consiting of α-Gal-Nac, α-Gal-Nac-Ser, α-Gal-Nac-Thr, β-Gal-Nac, β-Gal-Nac-Ser, β-Gal-Nac-Thr, β-Gal-(1–3)-α-Gal-Nac-Ser, β-Gal(1–3)α-Gal-Nac-Thr(α-Gal-Nac-Ser/Thr)$_2$, (α-Gal-Nac-Ser/Thr)$_3$ and (α-Gal-Nac-Ser/Thr)$_6$.

2. A immunogenic composition comprising the conjugate of claim 1 and a suitable carrier.

3. A immunogenic composition the conjugate of claim 1 and a suitable carrier and adjuvant.

* * * * *